US007418981B2

(12) United States Patent  
Baker et al.

(10) Patent No.: US 7,418,981 B2  
(45) Date of Patent: Sep. 2, 2008

(54) SYSTEM FOR DISPENSING BIOLOGICAL FLUIDS

(76) Inventors: James W. Baker, 1055 SW. Englewood Dr., Lake Oswego, OR (US) 97034; Gary A. Kirian, 5134 SW. Tree St., Lake Oswego, OR (US) 97035

(*) Notice: Subject to any disclaimer, the term of this patent is extended or adjusted under 35 U.S.C. 154(b) by 0 days.

(21) Appl. No.: 11/678,005

(22) Filed: Feb. 22, 2007

(65) Prior Publication Data

US 2007/0151984 A1    Jul. 5, 2007

Related U.S. Application Data

(63) Continuation of application No. PCT/US2005/031385, filed on Sep. 2, 2005, which is a continuation of application No. 10/933,849, filed on Sep. 2, 2004.

(51) Int. Cl.  
*B65B 1/04* (2006.01)  
*A61B 19/00* (2006.01)

(52) U.S. Cl. .............. 141/9; 141/27; 141/82; 141/104; 141/320; 141/329; 604/415

(58) Field of Classification Search .......... 141/2, 141/23–27, 82, 144, 319–323, 329, 330, 141/9, 100; 422/100–104; 604/403–416  
See application file for complete search history.

(56) References Cited

U.S. PATENT DOCUMENTS

| | | | | |
|---|---|---|---|---|
| 3,728,227 A | * | 4/1973 | Elson et al. | 435/287.3 |
| 4,407,133 A | * | 10/1983 | Edmonson | 62/3.62 |
| 4,842,028 A | * | 6/1989 | Kaufman et al. | 141/114 |
| 5,067,532 A | * | 11/1991 | Lang et al. | 141/329 |
| 5,555,920 A | * | 9/1996 | Godolphin et al. | 141/329 |
| 5,661,978 A | * | 9/1997 | Holmes et al. | 62/3.6 |
| 5,865,032 A | * | 2/1999 | MacPherson et al. | 62/3.62 |
| 5,911,252 A | * | 6/1999 | Cassel | 141/234 |
| 6,070,761 A | * | 6/2000 | Bloom et al. | 222/81 |
| 6,790,674 B2 | * | 9/2004 | Wright et al. | 436/180 |
| 6,877,530 B2 | | 4/2005 | Osborne et al. | |
| 6,976,349 B2 | | 12/2005 | Baldwin et al. | |
| 7,117,901 B2 | * | 10/2006 | Martinell Gisper-Sauch et al. | 141/2 |
| 7,128,105 B2 | * | 10/2006 | Tribble et al. | 141/319 |
| 2005/0281713 A1 | * | 12/2005 | Hampsch et al. | 422/102 |

* cited by examiner

*Primary Examiner*—Timothy L Maust  
(74) *Attorney, Agent, or Firm*—Kolisch Hartwell, P.C.

(57) ABSTRACT

Systems, including methods and apparatus, for dispensing biological fluids, such as allergens.

15 Claims, 26 Drawing Sheets

Fig. 10
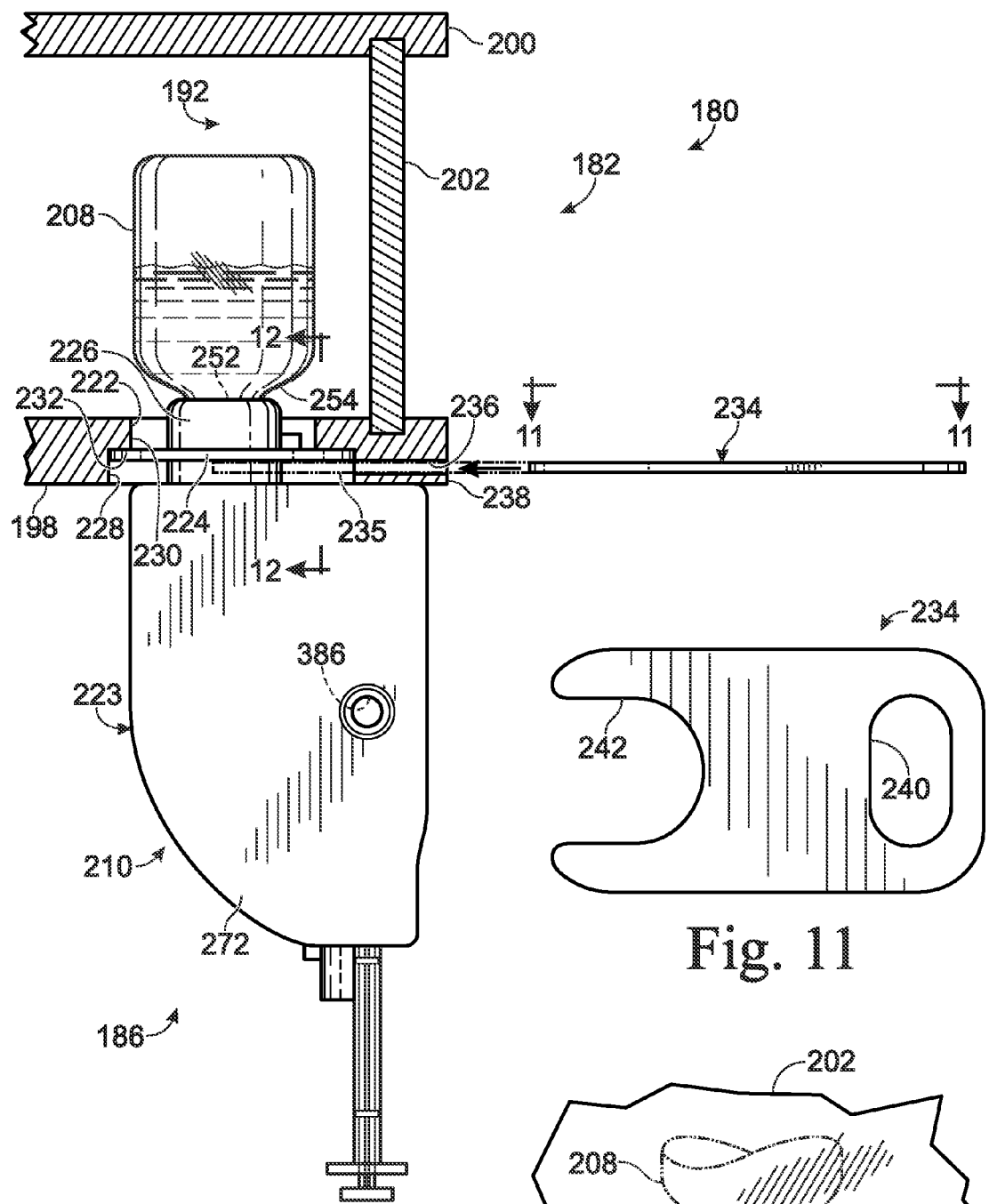
Fig. 11
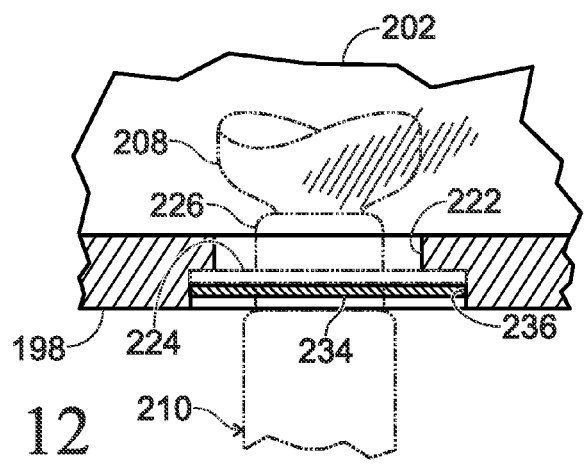
Fig. 12

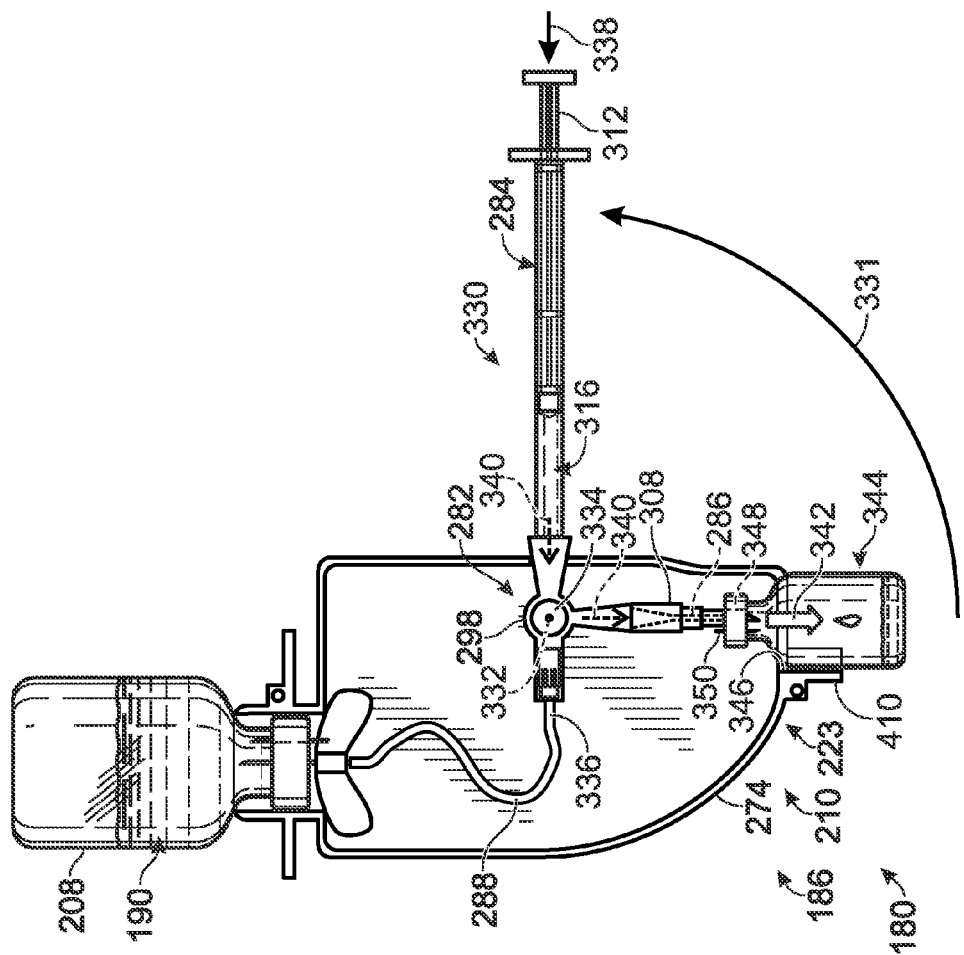
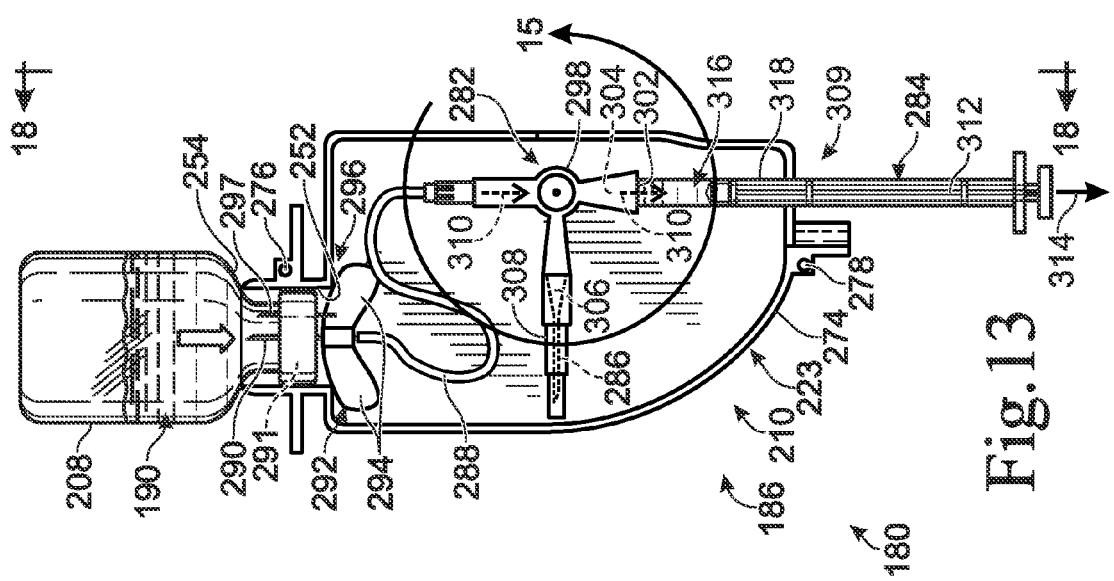
Fig. 14
Fig. 13

SYSTEM FOR DISPENSING BIOLOGICAL FLUIDS

CROSS-REFERENCE

This application is a continuation of PCT Patent Application Ser. No. PCT/US05/31385, filed Sep. 2, 2005, which in turn claims priority under U.S. and international law (including but not limited to the Paris Convention and 35 U.S.C. § 120) to U.S. patent application Ser. No. 10/933,849, filed Sep. 2, 2004. These applications are incorporated herein by reference in their entireties for all purposes.

INTRODUCTION

An allergy is an untoward reaction of the body's immune system to a foreign substance. The foreign substance may be known as an allergen (an allergy generating substance) and/or an antigen (an antibody generating substance). The immune system is made up of two parts: the antibody-mediated system and the cell-mediated system.

Allergic reactions to allergens have been classified into four major types (see Table 1). Three of these may involve the antibody-mediated system and one may involve the cell-mediated system.

TABLE 1

Exemplary Types of Allergic Reactions

| Type | Immune System Involvement | Antigens (Allergens) | Exemplary Diseases |
|---|---|---|---|
| Type 1 | Immunoglobulin E (IgE) | Pets (dander), dust, mold, pollen, medications, venoms, foods | Allergic rhinitis, asthma, eczema, anaphylaxis, |
| Type 2 | Immunoglobulin G (IgG) | Drugs, other chemicals | Hemolytic anemia |
| Type 3 | Immunoglobulin G (IgG) | Drugs, other chemicals | Glomerulonephritis |
| Type 4 | Lymphocytes | Various chemicals | Contact dermatitis (poison ivy) |

In the case of type 1 mediated allergy, allergens such as animal (pet) dander, dust mite antigen, mold, and/or pollen may combine with IgE antibodies on the surface of white blood cells known as mast cells. These cells then may secrete a number of chemicals including histamine which may cause hives, itchy watery eyes, nasal congestion, nasal discharge, throat swelling, coughing, wheezing, shortness of breath, gastrointestinal symptoms, and/or a shock-like state. A medical history and a physical from a patient with allergy symptoms may be used by a practitioner to make a presumptive diagnosis of type 1 mediated allergic disease. This diagnosis may be confirmed with skin tests and/or blood tests (RAST test) to test for the presence of antigen-specific IgE.

Management of allergic disease involves three major strategies: avoidance of the allergen, medications to block the allergic reaction, and/or immunotherapy. Of these, immunotherapy may be the most practical and effective, because it involves long-term desensitization to particular allergens by systemic exposure to controlled levels of these allergens. Immunotherapy involves making a vaccine from the various allergen extracts to which a patient is sensitive. For example, the patient might have positive skin tests to extracts from tree pollen, grass pollen, and cat dander. A vaccine may be prepared by mixing these extracts in a vial (the "patient's vial") and then diluting the mixed extracts to a level that the patient can tolerate for injection. Immunotherapy generally involves injection of increasing doses (decreasing dilutions) of the mixture over time, such as over the course of months or years, to a level that may be much higher than (in some cases several orders of magnitude greater than) the initial dose. This approach decreases the sensitivity of the patient to the injected mixture (and thus the injected allergens) and hopefully helps control the underlying allergic disease.

At present, most practitioners mix extracts using individual syringes to transfer specific amounts and concentrations of extracts from stock bottles to the patient's vial. Since the allergen mixture, or a dilution thereof, may be injected into the patient, the desired allergens/extracts generally are combined in the patient's vial under sterile conditions.

FIG. 1 shows a series of configurations produced by performance of a common method 20 for sterile transfer of a selected allergen 22. The allergen 22 may be provided as a sterile extract in liquid, contained in a stock vial 24. The stock vial may be generally transparent and may be sealed at its mouth with a closure 26, such as a resilient (elastomeric) septum 28. Septum 28 may be held in place by a retainer 30 extending around the neck of the vial 24, and particularly around a collar or flange formed on the neck of the vial. Retainer 30 also may extend partially over the exterior surface of the septum to leave an exposed region 32 of the septum for access to the interior of the vial with a hollow-bore needle (or other conduit). The needle may be used to pierce the septum, to provide fluid communication with the interior (the fluid contents) of the vial. Since the septum is elastomeric, after the needle pierces the septum, the needle and septum may be disposed in sealed engagement, circumferentially around the needle, in a configuration that prevents fluid leakage around the needle. The allergen 22 may be transferred to a patient's vial 34, which may be of generally similar construction to the stock vial, but often smaller in size. Transfer may be performed with a syringe 36 having a barrel 38 with graduations for volume measurement and a hollow-bore needle 40 for penetration of septum 28.

Configuration 42 shows stock vial 24 prepared to receive needle 40 of the syringe. Stock vial 24 may be in an upright or inverted configuration. Exposed region 32 of the septum and the exterior surface of the needle may carry microorganisms that would contaminate the transferred fluid. Accordingly, the exterior surface of the septum may be disinfected by wiping this surface with alcohol prior to penetration with the needle, and the needle may be obtained in a sterile condition, such as by treatment with heat, steam, a chemical, and/or electromagnetic radiation, among others. Furthermore, the stock vial, the syringe, and the patient's vial may be disposed in a laminar flow hood equipped with bacteriostatic illumination before, during, and/or after performance of the steps illustrated in FIG. 1.

Configuration 44 shows stock vial 24 placed in fluid communication with syringe 36 by insertion of the needle through the septum and into contact with the allergen. A plunger 46 of the syringe has been moved outward within the barrel to load a measured volume of the allergen, shown at 47, from the stock vial into barrel 38.

Configuration 48 shows syringe 36 removed from the stock vial and holding measured volume 47 of the allergen and positioned above patient's vial 34. The patient's vial also may be disinfected on the exterior surface where the syringe will penetrate a septum 50 of this vial, particularly if the patient's vial has already received other allergens in separate dispensing operations.

Configuration 52 shows syringe 36 placed in fluid communication with the patient's vial by penetration of the septum of the patient's vial with needle 40 of the syringe. Plunger 46 may be moved inward within barrel 38 of the syringe to expel the measured volume of the allergen from the syringe barrel into the patient's vial.

The method shown here may be repeated for each selected extract to introduce a desired set and ratio of allergens into the patient's vial and thus to form a custom mixture for further dilution and/or injection into a patient. However, this commonly used method for preparation of allergen mixtures may have a number of drawbacks. Generally, each stock vial may be placed at room temperature from refrigerated storage, and allowed to remain at room temperature and exposed to light before and during formation of allergen mixtures. In some cases, the stock vials may sit at room temperature, exposed to light, for many hours as various allergen mixtures are being prepared. Over time, the allergens in the stock vials thus may be physically and/or chemically damaged (such as denaturation, oxidation, and/or cleavage of allergen proteins), with unpredictable changes in allergen potency that may affect diagnosis or treatment of patients using the allergens. Furthermore, this common method of preparing allergen mixtures may be too labor intensive, wasteful of syringes, unsafe, and/or prone to contamination and/or human error, among others.

SUMMARY

The present teachings provide systems, including methods and apparatus, for dispensing biological fluids, such as allergens.

BRIEF DESCRIPTION OF THE DRAWINGS

FIG. 10 is a partially exploded, fragmentary sectional view of the system of FIG. 8, taken generally along line 10-10 of FIG. 8.

FIG. 11 is a top plan view of a dispenser retainer of the system of FIG. 8, taken generally along line 11-11 of FIG. 10.

FIG. 12 is fragmentary sectional view of selected portions of the system of FIG. 8, taken generally along line 12-12 of FIG. 10.

FIG. 13 is a side elevation view of a dispenser station of the system of FIG. 8, viewed generally as in FIG. 10, with the dispenser station in a loading configuration and with a portion of a housing of the dispenser station removed, in accordance with aspects of the present teachings.

FIG. 14 is a side elevation view of a dispenser station of the system of FIG. 8, viewed generally as in FIG. 10, with the dispenser station in a delivery configuration and with a portion of a housing of the dispenser station removed, in accordance with aspects of the present teachings.

DETAILED DESCRIPTION

The present teachings provide systems, including methods and apparatus, for dispensing biological fluids, such as allergen extracts. The systems may provide dispensers that couple supply vessels of biological fluids to receiver vessels by engagement with closures of the vessels, particularly sealed engagement with elastomeric closures. In some embodiments, the dispensers may include conduits configured to penetrate the closures of the supply and receiver vessels. For example, the conduits may be pointed, to pierce the closures, and the conduits may include an internal bore through which fluid may flow through the conduit (and closure). The supply vessels may remain coupled to the dispensers as the dispensers are operated to transfer the biological fluids to the receiver vessels. Each receiver vessel may be engaged selectively with a suitable set of dispensers to select the types and amounts of biological fluids to be dispensed to the receiver vessel, for example, to mix a custom set of allergen extracts in the receiver vessel. The dispensers may be configured to minimize exposure of the biological fluids to the ambient environment as they are dispensed, so that the chance of contamination of the fluids is minimized and the biological fluids remain at least substantially sterile. Accordingly, the biological fluids dispensed into the receiver vessels may be suitable for injection into human subjects, such as allergy patients.

Further aspects of the present teachings are included in the following sections, including, among others, (I) overview of exemplary dispensing systems; (II) vessels; (III) biological fluids; (IV) dispensers, including (A) conduit structures, (B) pumps, (C) valves, (D) dispenser housings, and (E) additional features; (V) housings; (VI) thermal control systems; (VII) controllers; (VIII) drivers; (IX) methods of operation; and (X) examples.

I. Overview of Exemplary Dispensing Systems

This section describes exemplary systems for dispensing biological fluids, in accordance with aspects of the present teachings. These systems may include a variety of components, including supply vessels, dispensers, receiver vessels, and/or controllers, among others.

Figure 1:
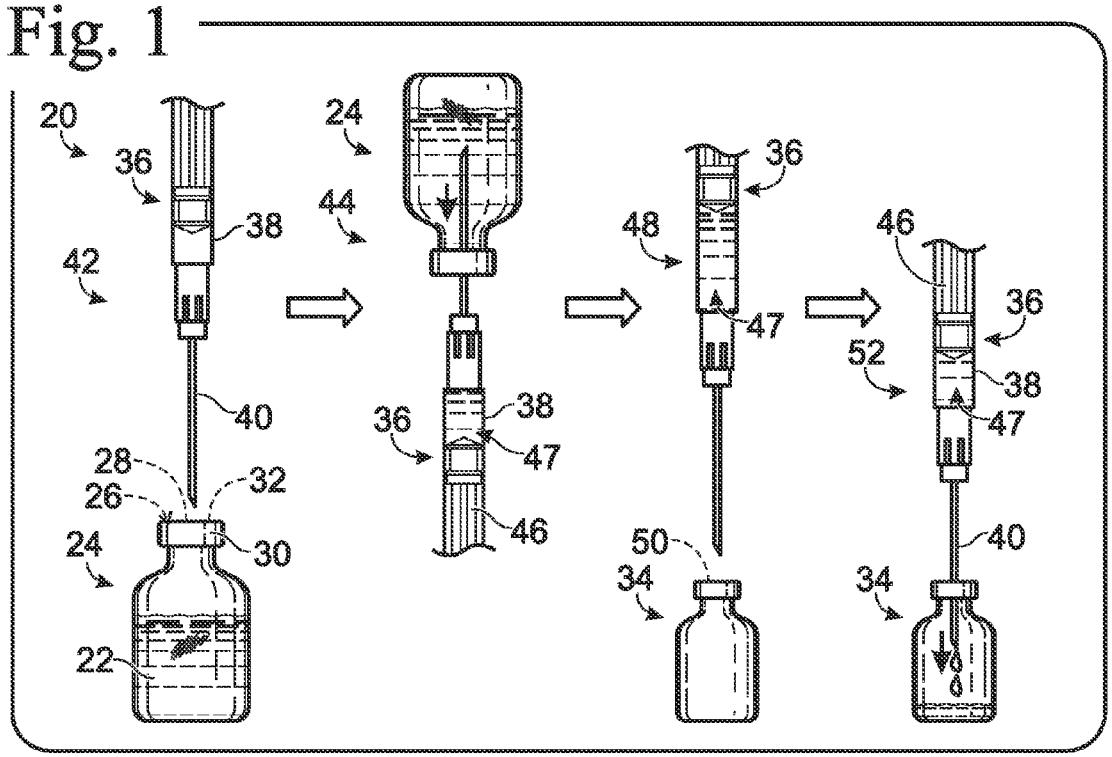
FIG. 1 is a series of configurations produced by performance of a common method for sterile transfer of an allergen extract from a stock vial to a patient's vial so that a customized mixture of allergens can be prepared for further dilution and/or injection into a patient.
Figure 2:
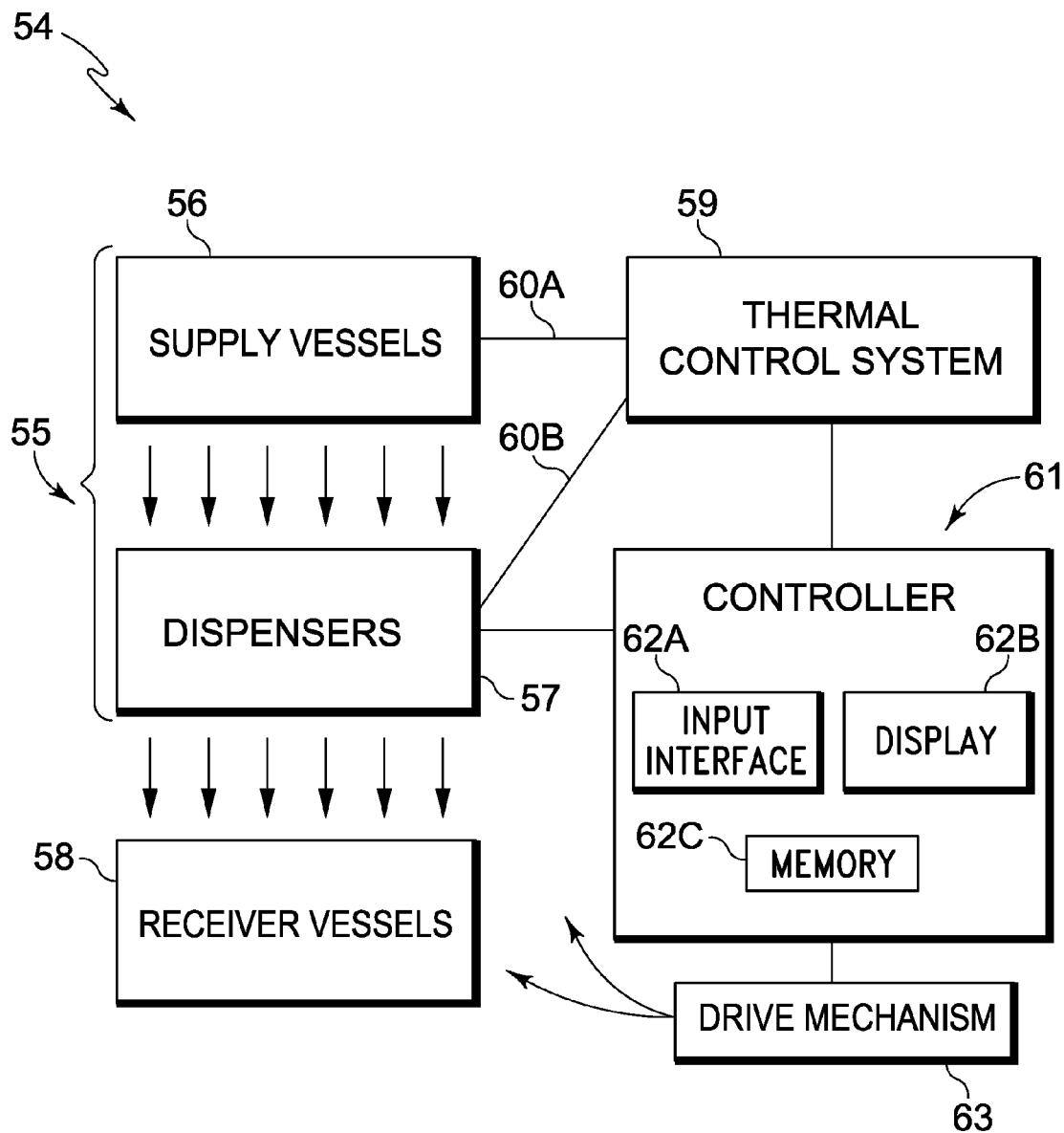
FIG. 2 is a schematic view of an exemplary system for dispensing biological fluids, in accordance with aspects of the present teachings.

FIG. 2 shows a schematic view of a first exemplary system 54 for dispensing biological fluids. System 54 may include a plurality of dispenser stations 55 at which supply (e.g., stock) vessels 56 with biological fluids are coupled to dispensers 57. Receiver vessels 58 may be coupled selectively to the dispenser stations such that operation of the corresponding dispensers results in transfer of aliquots of the biological fluids to the receiver vessels. Further aspects of vessels and biological fluids are described below, for example, in Sections II and III, respectively.

System 54 also may include a thermal control system 59 that regulates the temperature of the supply vessels and their fluid contents. For example, the thermal control system may cool (and/or heat) the supply vessels, shown at 60A, to the same and/or different temperatures. In some examples, the thermal control system may be configured to cool (refrigerate) the supply vessels and/or a compartment(s) in which the supply vessels are disposed, such that the biological fluids in the supply vessels are maintained at a temperature below the ambient temperature around the system. In some examples, the thermal control system also or alternatively may regulate, indicated at 60B, the temperature in a compartment around the dispensers.

System 54 further may include a controller 61. The controller may, for example, include an input interface 62A (e.g., to receiver user inputs or other data, such as scanned or read data, and/or temperature data from the thermal control system), a display 62B to output (or input) data related to system 54, and/or memory 62C to store instructions (e.g., software, hardware, and/or firmware) for, user preferences about, and/or data produced by, operation of the system. Further aspects of controllers are described below, for example, in Section VII.

In some embodiments, system 54 may include a drive mechanism (a driver) 63 to drive relative movement within the system. The driver may be configured, for example, to move the supply vessels, structures of the dispensers, and/or the receiver vessels, among others. For example, the driver may be configured to pivotably and/or translationally move a housing holding the supply vessels (and/or dispensers), and/or to reposition the supply vessels (and/or dispensers) relative to an operator of the system and/or a receiver vessel(s). Alternatively, or in addition, the driver may drive movement of a receiver vessel(s), such as vertical movement to engage the receiver vessel with a dispenser (to provide fluid communication between the dispenser and the receiver vessel) and/or horizontal movement to align a receiver vessel with a dispenser and/or dispenser station. Further aspects of drivers are described elsewhere in the present teachings, such as in Section VIII.

Figure 3:
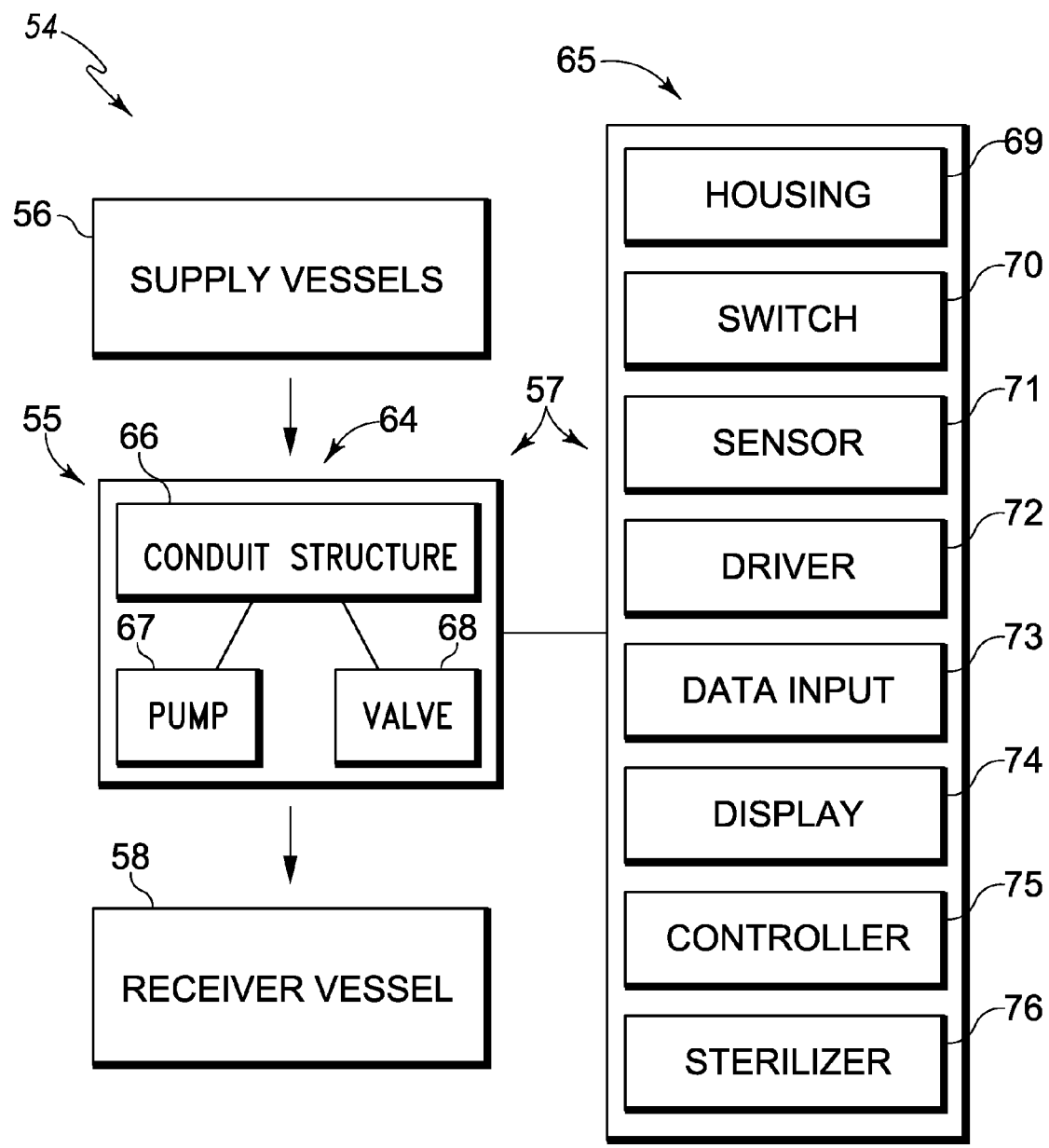
FIG. 3 is a schematic view of an exemplary dispenser station of the system of FIG. 2, including a fluidics mechanism that provides fluid transfer from a supply vial to a receiver vial, and a set of additional features that may be included in the dispenser station in any suitable combination, in accordance with aspects of the present teachings.

FIG. 3 shows an exemplary dispenser station 55 of system 54. Dispenser 57 of the dispenser station may include a fluidics mechanism 64 that provides fluid transfer from stock vessel 56 to receiver vessel 58. The dispenser optionally may include one or more additional features 65.

Fluidics mechanism 64 may include a conduit structure 66, at least one pump 67, and at least one valve 68, among others. The conduit structure may provide a fluid flow path(s) between the supply vessel and the receiver vessel. In some examples, the conduit structure may engage closures of the supply and receiver vessels tightly enough to restrict fluid flow at the site of engagement between the closures and conduit structure (sealed engagement) and/or may extend through the closures. Accordingly, the conduit structure may permit fluid to be transferred between vessels that remain substantially closed and/or that can re-seal themselves by removal of the conduit structure (uncoupling the conduit structure from the vessels). The pump (or pumps) may propel fluid through the conduit structure and may be used to control and/or measure the volume of fluid transferred from a supply vessel to a receiver vessel. The valve (or valves) may regulate flow of fluid through the conduit structure, for example, to determine the direction of fluid flow. Further aspects of fluidics mechanisms are described, for example, in Section IV and in the Examples, among others.

Features 65 of the dispenser may be involved in operation, control, protection, and/or monitoring of the dispenser, among others. These features may be included in at least one dispenser, any suitable subset, or all of the dispensers of the system (or may be absent from the system). Each feature may be present one or more times in a dispenser, in the same or different forms. In some examples, a feature may be shared among two or more dispensers (or all dispensers to provide system features). These features may include a housing 69, a switch 70, a sensor 71, a driver 72, a data input mechanism 73, a display 74, a controller 75, and/or a sterilizer 76, among others. Further aspects of these features are described elsewhere in the present teachings, such as in Section IV and in the Examples, among others.

Figure 4:
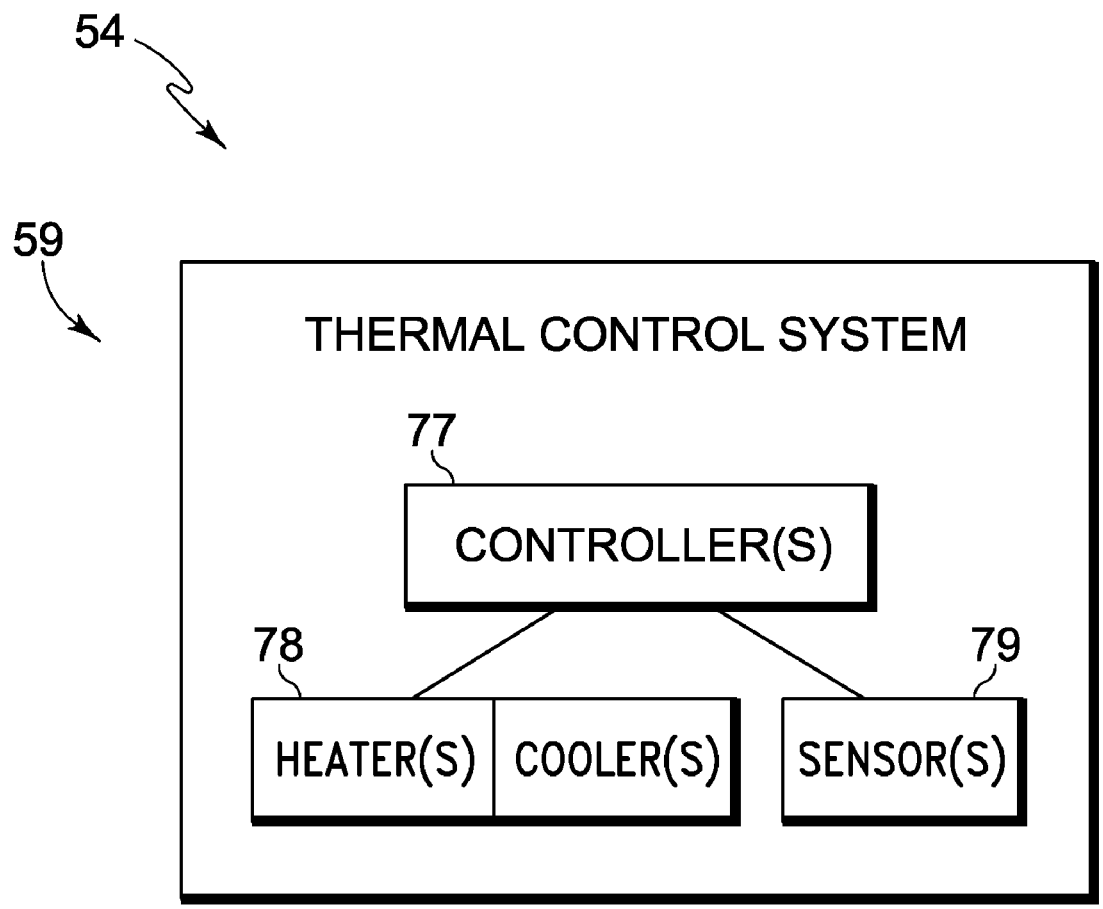
FIG. 4 is a schematic view of a thermal control system of the system of FIG. 2.

FIG. 4 shows thermal control system 59 of system 54. The thermal control system may include at least one controller 77, at least one heater and/or cooler 78, and/or at least one temperature sensor 79. In some examples, the controller may be in communication with at least one heater/cooler and sensor to provide a feedback-based regulation of temperature within the system. In particular, the controller may receive a sensed signal(s) from the sensor and then generate a control signal for the heater/cooler based on the sensed signal(s). The sensor then may sense any temperature change produced by operation of the heater/cooler, to complete the loop. Further aspects of thermal control systems are described below, for example, in Section VI.

Figure 5:
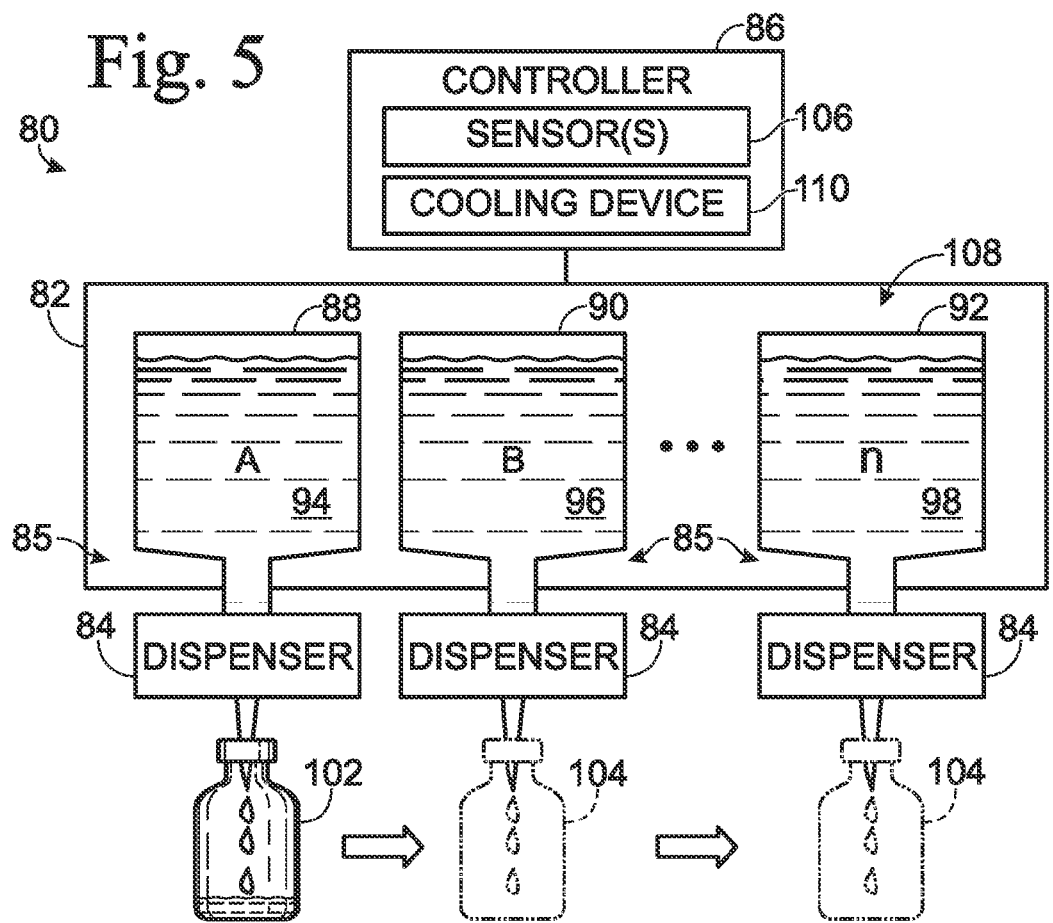
FIG. 5 is a schematic view of another exemplary system for dispensing biological fluids, in accordance with aspects of the present teachings.

FIG. 5 shows a schematic view of a second exemplary system 80 for dispensing biological fluids, such as allergens. System 80 may include a housing 82, a plurality of dispenser units 84 coupled to the housing, and a controller 86 to monitor and/or regulate any suitable aspects of the system.

Housing 82 may be configured to hold a plurality of supply (stock) vessels, such as vessels 88, 90, 92. Each stock vessel may include a biological fluid, such as fluids 94, 96, 98, generally in liquid form. The housing may be configured to protect the supply vessels and their biological fluids from ambient conditions, for example, by defining an interior compartment(s) that may be cooled, protected from light, etc. In some examples, the housing may be coupled movably to a base, so that the housing may reciprocate or turn, among others, on the base. This movement of the housing may permit a person dispensing the biological fluids to gain sequential access to, and/or to conveniently position, different dispensers/biological fluids.

Dispenser units (or dispensers) 84 each may be configured to remain coupled continuously to the housing and to the supply vessels during dispensing operations and/or when system 80 is idle, to provide a set of dispenser stations 85. Accordingly, the dispensers (and the dispenser stations) may be attached to the housing with fixed relative positions, so that the dispensers are disposed in a fixed array for more convenient and/or error-free identification of dispenser stations. The dispensers/dispenser stations also may be configured to be uncoupled from the housing (with or without their coupled supply vessels) to permit, for example, maintenance, replacement, and/or replenishment of dispensers, supply vessels, and/or biological fluids. The dispensers may be coupled to a receiver vessel 102 into which one or more of the biological fluids may be dispensed. The receiver vessel 102, shown in solid outline, may be coupled to only one dispenser, or may be coupled in parallel or sequentially to one or more additional dispensers, shown in phantom outline at 104, to mix and/or dilute various biological fluids from the supply vessels.

Controller 86 may be coupled to the housing, the supply vessels, and/or the dispensers, among others. The controller may include one or more sensors 106 to detect one or more aspects of the system, such as the temperature and/or humidity of an interior compartment 108 of the housing, information about a supply and/or receiver vessel, and/or the like. The controller also or alternatively may include one or more devices for modifying a condition of the interior compartment, such as a cooling device 110 and/or humidifier/dehumidifier, or the like. The controller further may be in communication with the dispensers to monitor and/or regulate aspects of dispenser operation, such as pump operation (e.g., volume of fluid dispensed from a dispenser).

Figure 6:
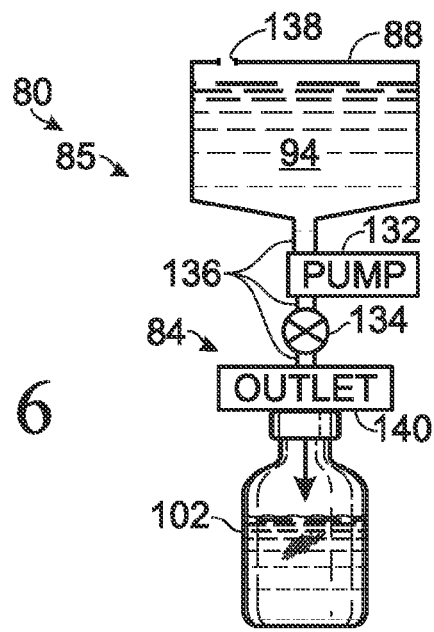
FIG. 6 is a somewhat schematic view of a dispenser station from the system of FIG. 5.
Figure 7:
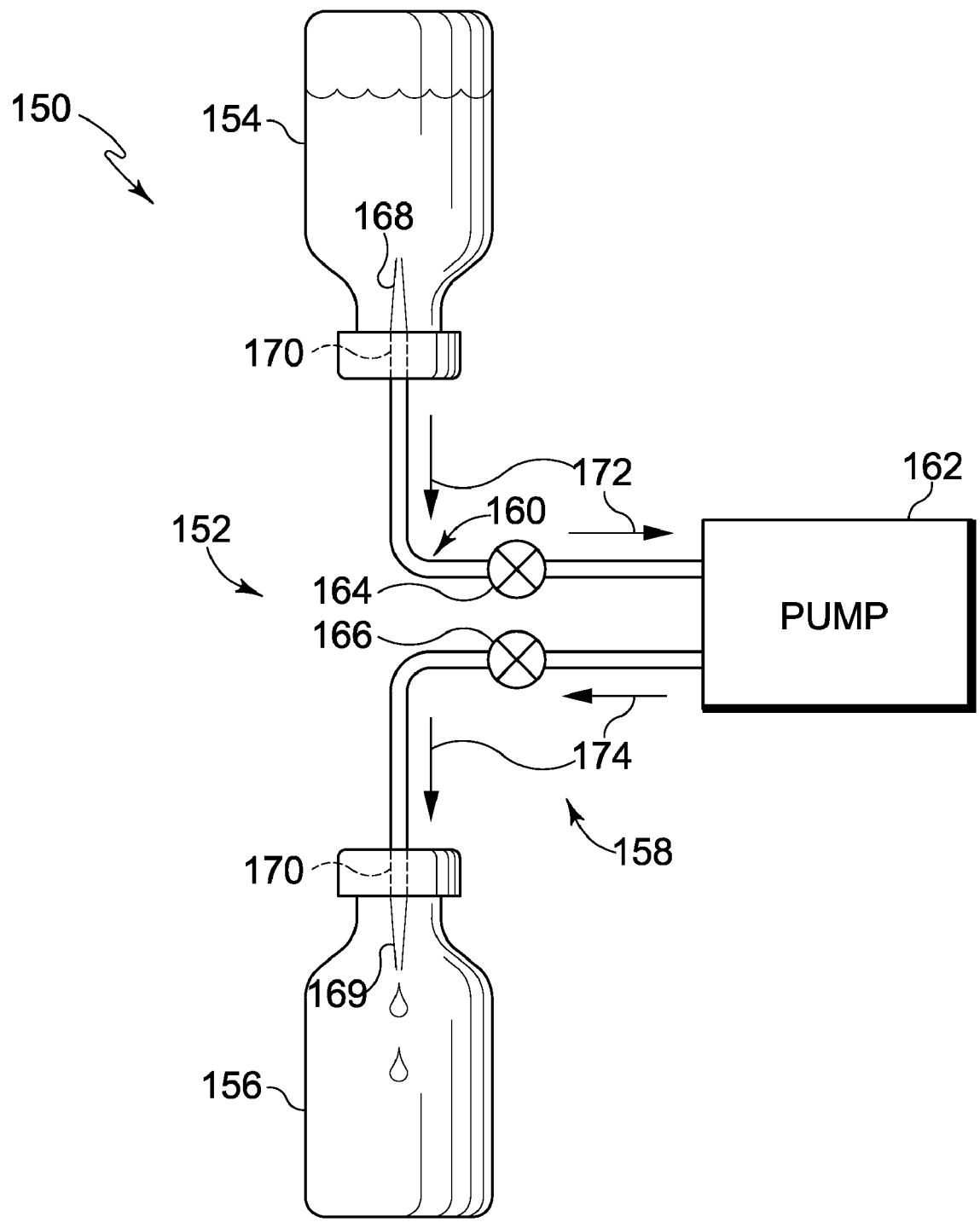
FIG. 7 is a somewhat schematic view of another exemplary dispenser station that may be included in the systems of the present teachings.

FIG. 6 shows a somewhat schematic view of a dispenser station 85 from system 80. The dispenser station, and particularly the dispenser unit 84 of the station, may include a pump 132 to move fluid, and a valve 134 operable to direct and/or restrict fluid flow through a conduit structure 136 of the dispenser unit. The conduit structure may provide fluid communication between supply vessel 88, the pump, the valve, and/or receiver vessel 102.

In some examples, operation of the valve may place the dispenser unit in a loading configuration or in a delivery (or release) configuration. The loading configuration may place the pump in fluid communication with biological fluid 94 of supply vessel 88, for loading a measured volume of the biological fluid into the pump. The supply vessel also may include or be coupled to a vent 138 that restricts formation of a negative pressure in the supply vessel during loading. In some examples, the vent may be provided by part of the conduit structure itself (e.g., the Examples). The delivery configuration may place the pump in fluid communication with an outlet 140 that may be coupled to receiver vessel 102, for delivering a measured volume of fluid to the receiver vessel with the pump. (The volume loaded into the pump may be the same as, or different from, the volume delivered from the pump.) The pump and/or the valve may be operated and/or actuated manually and/or automatically. In some examples, the valve may be operated (and/or adjusted) by moving the pump between a loading configuration and a release configuration. In other examples, the valve further may be operated (and/or adjusted) by moving the pump between additional configurations, such as two or more loading configurations, two or more release configurations, holding configurations, and so on.

FIG. 7 shows another exemplary dispenser station 150 including a dispenser 152 coupling a supply vessel 154 to a receiver vessel 156. Dispenser 152 may include a fluidics mechanism 158 having a conduit structure 160, a pump 162, and one or more valves 164, 166.

Conduit structure 160 may remain coupled to the supply vessel as the receiver vessel is coupled to and uncoupled from the fluidics mechanism, such that a fluid aliquot can be transferred from the supply vessel to the receiver vessel without disengagement of the dispenser from the supply vessel. End regions or conduits 168, 169 of the conduit structure may be configured to pierce closures 170, 171 of the vessels.

Valves 164, 166 (or one valve) may be adjustable to direct fluid flow in the conduit structure. For example, the valves may be adjustable to provide selective fluid communication between the pump and the supply vessel, such that a loading pathway 172 is open and a delivery pathway 174 is closed. The valves also may be adjustable to provide selective fluid communication between the pump and the receiver vessel, such that the loading pathway is closed and the delivery pathway is open. In some examples, this adjustable fluid communication may operate to restrict reverse flow of fluid in the system, that is, to restrict flow of fluid from the receiver vessel to the supply vessel, from the receiver vessel to the pump, and/or from the pump to the supply vessel, among others. Restricting reverse flow of fluid may, for example, reduce contamination of the supply vessel and/or conduit structure and/or may provide better operation of the pump. The valves may be adjustable by any suitable mechanism, including movement of the pump (all or a portion of the pump), operation of the pump, manual actuation of a switch (directly or indirectly by an operator), automatic actuation of a switch, and/or the like.

The systems provided herein may have a number of advantages for dispensing biological fluids, particularly forming mixtures of allergens for immunotherapy. The advantages may include one or more of the following, among others: (1) reduced light-mediated degradation of biological fluids, (2) reduced temperature-mediated degradation of biological fluids, (3) increased speed of dispensing to form mixtures, (4) decreased labor costs, (5) fewer punctures of stock vessels (through their closures) and thus a reduced number of closure-derived plugs in the biological fluids, (5) improved longevity and consistency of biological fluids, (6) improved organization of stock biological fluids in an array, (7) reduced chance of needle sticks, (8) reduced repetitive finger injuries, (9) decreased chance of errors in dispensing, (10) reduced chance of replacing syringe needle in wrong stock vessel, (11) reduced repetitive sterilization of closures of stock and receiver vessels (and associated chance of sample contamination and/or degradation), (12) reduced set-up time, (13) easier replacement of stock vessels when depleted, (14) higher speed without the expense and maintenance costs of a high technology system, (15) parts may be disposable, (16) decreased syringe usage, (17) vented with reduced vacuum, less denaturation, and fewer air bubbles than would be produced typically by fast movement of fluid through needles, (18) quicker and/or more efficient addition of diluent, (19) definite procedure for loading, checking, and delivering to increase accuracy, (20) reduced need for bacteriostatic lights (which may denature allergens), (21) reduced chance of contamination, (22) less chance of undesired direct contact between fluids in stock and receiver vessels, (23) manual operation that is easy to learn, and/or (24) reduced condensation and thus fewer problems with labels coming off vessels.

II. Vessels

The dispensing systems described herein may be configured to be used with vessels for holding biological fluids. The vessels may have any suitable size, shape, composition, closure, and/or coupling structure, among others.

The size of each vessel may be selected, for example, according to the volume of biological fluid(s) to be held in the vessel, the capacity of the pump, and/or the volumes to be dispensed, among others. Accordingly, supply vessels may be large enough to hold one dispensed volume or a plurality of dispensed volumes. In some examples, the supply vessels may be large enough to hold many dispensed volumes, such as about 10, 100, or 1,000 dispensed volumes, among others. In some examples, each dispensed volume may be about 0.1 to 1.0 milliliters and a supply vessel may have a capacity of about 10 to 100 milliliters of fluid. In other examples, the supply vessel may have a capacity of about 0.1 to 10,000 milliliters. Similarly, receiver vessels may be large enough to hold at least one dispensed volume or a plurality of dispensed volumes, with or without added diluent. Receiver vessels thus may be similar in size to supply vessels, or larger or smaller than the receiver vessels. In some examples, a receiver vessel may have a capacity of about 5 to 25 milliliters. In other examples, the receiver vessel may have a capacity of about 0.1 to 1000 milliliters.

The vessels may be shaped according to their intended purposes. The vessels may be generally cylindrical, frustoconical, spherical, cubical, polyhedral, and/or the like. The vessels may have flat bottoms, to support the vessels on a flat surface. The vessels may have a varying diameter, for example, narrowing near the top of the vessels, to provide a neck that defines the mouth of the vessels.

The vessels may be formed of a material that is generally inert to the biological fluids. Exemplary materials may include glass (e.g., borosilicate glass), plastic, and/or metal, among others. The material may be at least partially transparent or may be opaque. The material may be colorless, or may be colored, for example, darkened or tinted to restrict entry of light.

The vessels may include coupling structures to permit conduits to be coupled to the vessels. The coupling structures may be included in closures, and/or may be distinct from the closures. The coupling structures may permit conduits to be placed in fluid communication with the vessels in a sealed relationship, so that fluid can pass through the conduits from and/or to vessels, but generally is restricted from passing between the exterior of the conduit and vessels.

The vessels may have elastomeric/resilient closures, such as septa, to seal the vessels and thus restrict fluid passage from/to the vessels. A closure may be any structure that at least substantially restricts passage of fluid, and particularly a liquid, into and/or out of a vessel. In some examples, the closure may hermetically seal the vessel, at least prior to coupling the vessel to a dispenser. The closures may include plugs, septa, caps, lids, and/or the like. Closures may be secured to vessels by threadable engagement, an interference fit, a clip or retainer, a resilient flange, and/or the like.

In some examples, the closures may be configured to receive a conduit. The closures may be penetrated and/or pierced by hollow conduits, such as hollow needles, to permit fluid movement from/to the vessels, for example, to remove and/or add a volume of biological fluid to/from the vessels and/or to function as a vent during and/or after this movement. A resiliency and/or elasticity of the closures may provide a seal around the conduits after the closures are penetrated by the conduits and/or may seal the closures after the conduits are removed from the closures. The seal between a conduit and a closure may substantially restrict fluid flow at the seal. However, in some examples, the seal also may permit limited movement of gas around the conduit, to relieve a pressure differential between the inside and outside of the vessel (see Example 2).

In exemplary embodiments, the vessels may be vials. A vial, as used herein, is a vessel for holding relatively small amounts of fluid. In exemplary embodiments, a vial may hold less than or equal to about 500 milliliters or 100 milliliters of fluid, among others.

III. Biological Fluids

The dispensing systems described herein may be configured to be used for transfer of biological fluids between vessels, particularly for forming predefined mixtures of the biological fluids in vessels.

The biological fluids generally include any fluid—liquid and/or gas—at least partially derived from and/or affecting living organisms. The biological fluids may include any suitable ratios of biological extracts, synthetic compounds, microorganisms, organelles, excipients, diluents, buffers, salts, and/or the like. The biological fluids also may include markers, such as dyes and/or other (preferably biologically inert) compounds, to identify the fluid and/or to indicate addition or removal of fluids during sample preparation. The biological fluids may be aqueous, or predominantly aqueous, having water as a major component. However, in some cases, the fluids may be organic, having an organic solvent (particularly a biologically compatible organic solvent such as DMSO or DMF) as a major component. Alternatively, or in addition, the biological fluids may include trace amounts of organic solvents, such as DMSO or DMF, particularly if used as a carrier for another component.

The biological fluids may be used for any suitable purpose. For example, each biological fluid may be a preparation, such as a drug, a vaccine (an antigen), or an antitoxin, used medically as a diagnostic, preventive, and/or therapeutic agent. The preparation may be at least partially synthesized by living organisms or their products, and/or may be based structurally on a material produced by a living organism. Exemplary biologically active agents in biological fluids may include proteins, peptides, nucleic acids, carbohydrates, vitamins, metal ions, lipids, hormones, etc. More specifically, exemplary biologically active agents may include allergens, such as extracts (particularly protein extracts) from food, molds, animal dander, plants, pollens, dust mites, venoms, bacteria, and/or the like. In some examples, the biological fluids may include synthetic allergens, for example, synthetic peptides. Exemplary biologically active agents also may include research, diagnostic, and/or clinical materials obtained via any suitable mechanism (e.g., excisions, aspirations, swipes, swabs, phlebotomies, etc.) from biopsies and/or necropsies of cells, tissues, and/or biological fluids (e.g., saliva, blood, urine, lymph, mucous, semen, etc.), among others.

The biologically active agents may be present at any suitable concentration. Accordingly, in some examples, the biological fluids may include different dilutions of a biologically active agent, such as serial two-fold or ten-fold dilutions, among others. Alternatively, or in addition, the biological fluids may include repetitions of the same fluid (i.e., two or more stations having the same fluid), particularly commonly used fluids.

The biologically active agents may be present in any suitable amount(s), in any suitable state(s). The amounts may be measured by concentration, for example, picomolar, nanomolar, micromolar, millimolar, and molar. Alternatively, or in addition, the amounts may be measured in effective amounts, for example, effective to induce or desensitize an immune response, effective to bring about a desired therapeutic response, effective to diagnose a condition, and so on. The suitable states may include solutions, suspensions, emulsions, dispersions (including colloidal dispersions), gels, aerosols, and so on, and/or mixtures thereof.

IV. Dispensers

The dispensing systems described herein may include one or more dispenser stations at which biological fluids may be dispensed. Each dispenser station may include a dispenser configured for manual and/or automatic operation. The dispenser may include conduit structure that provides a sealed coupling with a supply vessel, a receiver vessel, and/or between the supply and receiver vessels. The dispenser also may include at least one pump and/or at least one valve configured to move fluid through the conduit structure and/or direct and/or regulate this fluid movement.

The dispenser stations and/or their dispensers may have any suitable arrangement in a dispensing system. In some cases, the dispenser station at a given position may be missing, replaced with a nonfunctional blank, or replaced with a solid dispenser (e.g., to dispense easily soluble materials such as salts for use in preparing buffers). In the same or other cases, dispensers designated for and/or containing biological fluids related by some common characteristic (e.g., type (e.g., grass allergen, tree allergen, etc.), concentration (e.g., low concentration, high concentration, etc.), and so on) may be organized relative to one another according to some predefined criteria or rule. For example, biological fluids that commonly would be dispensed into a common receiving vessel may be positioned adjacent one another to enhance the speed and convenience of dispensing, and biological fluids that less commonly would be dispensed together, or that should not be dispensed together, may be positioned far from one another to reduce the possibility that they will be co-dispensed.

A. Conduit Structures

The dispensers each may include a conduit structure that provides fluid communication between the valve, pump, supply vessel, and/or receiver vessel. The conduit structure may include any suitable mechanism for routing fluid, such as rigid tubes, flexible tubing, pipes, channels, bores, manifolds, and/or the like.

The conduit structure may include any suitable number of conduits connected by any suitable connector mechanisms. Exemplary mechanisms for connecting conduits to each other and/or to a valve and/or a pump within a dispenser may be reversible or non-reversible, including connections that are Luer-Loc, snap-fit, interference fit, clamped, threaded, bonded, adhesive, welded, and/or the like. In some examples, one or more of the conduits or other dispenser components may be sealed adjacent an opening with a swabbable valve that remains closed until the conduit or component is connected to another conduit or component.

Coupling conduits generally include any structures at which biological fluids can be transferred from a supply vessel to a dispenser (an inlet conduit) and/or from a dispenser to a receiver vessel (an outlet conduit). The coupling conduits thus may include a conduit or conduit region having a tip into and/or from which biological fluids can enter or exit a dispenser. The tip may be blunt or sharp (such as a hollow-bore needle). Coupling conduits alternatively or in addition may include coupling structure with which these conduits may be coupled to a supply or receiver vessel, such as a plug, cap, and/or the like, attached to the coupling conduit and configured for engagement with the supply or receiver vessel. This plug or cap may be sealed circumferentially around the coupling conduit to restrict fluid leakage. Alternatively, the coupling conduit itself may engage the supply or receiver vessel so that the conduit is sealed against the vessel, such as by penetration of a closure of the supply or receiver vessel, or the coupling conduit may deliver biological fluids in a nonsealed relation with the receiver vessel (such as through an open mouth of this vessel). An outlet conduit may be configured for contact and/or noncontact dispensing, in which the outlet conduit contacts or does not contact the receiving fluid or container as part of the dispensing process, respectively. The coupling cap or attachment to the supply vessel may be designed as a one-way insertion device, clamping and/or sealing the supply vessel in place. In addition, the coupling cap or attachment to the supply vessel may be designed as a break-away connection if the supply vessel is removed before it is completely emptied to prevent unauthorized use of the dispensing system, e.g., the supply vessel is returned to storage or removed for another purpose from the coupling conduit.

B. Pumps

Pumps generally include any device for actively moving biological fluids within the dispensers. Such active movement may be effected by pushing and/or pulling and/or otherwise biasing fluid to and/or from the pumps. The active movement may be effected, for example, by directly pushing on the fluid, for example, by a piston, a vane, pressurized gas, and/or a spring, among others.

Pumps used for dispensing may be any suitable manually operated or automated pumps. A manually operated pump may be driven by direct engagement of an operator with the pump, such as engagement of a syringe piston (plunger) with a hand(s), and/or engagement with a pump coupled structure, such as a mechanical assist mechanism, among others (e.g., see Example 5). Automated pumps may include a motor, such as an electric motor, that drives the pumps. Motor-driven pumps may include a driver or motor that is controlled manually, such as by having a user manipulate a pump control (such as a switch), and/or automatically, such as with a controller (e.g., see Example 6).

The pumps may be of any suitable type including positive-displacement and/or dynamic pumps, among others. Positive-displacement pumps may move fluid by filling a cavity and then displacing a given volume of the fluid. Exemplary positive-displacement pumps may include piston, bellows, double-diaphragm, flexible impeller, gear, oscillating, progressing cavity, rotary, linear, and/or peristaltic pumps, among others. Dynamic pumps may move fluid by increasing its speed or velocity. Exemplary dynamic pumps may include centrifugal pumps.

The pumps may be configured to move measured volumes of fluid, for example, based on the number of pump strokes/cycles performed, and/or based on the size of a partial stroke/cycle of a pump, among others. Any suitable volume may be measured and moved by a pump. A volume transferred by a pump may be selected during operation of the pump, such as during manual operation of a syringe pump, and/or may be selected before pump operation, such as through input of volume data to the controller of an automated pump system. Input may be via any suitable interface such as a keyboard, touchscreen, mouse, joy stick, touch screen, dial, lever, button(s), network connection, etc. (e.g. see Example 6). The interface may be a dedicated interface for an individual dispenser or subset of dispensers (such as the dispensers on a side of the dispensing system), and/or may be an interface for inputting volume data for all of the dispensers.

Operation of the pump may be detected by one or more sensors. The sensor may sense any suitable aspect or result of pump operation, such as plunger position and/or range of motion, motion of a motor driving the pump, pressure produced, fluid flow rate, and/or the like. Accordingly, the sensor may allow a controller to monitor, verify, and/or record pump operation and/or a volume dispensed to a receiver vessel, among others. Exemplary sensors may include rotary encoders, linear encoders, piezoelectric sensors, heat conduction sensors, and/or the like. Further aspects of using sensors to measure pump operation are described elsewhere in the present teachings, such as Section VII and Examples 5 and 6, among others Exemplary pumps may include manually-driven or power-driven syringe pumps. The syringe pumps may have any suitable barrel capacity, such as a capacity of about 0.1 to 10 milliliters, among others. In some examples, a dispensing system may include syringes of different capacities coupled to different dispensers, such as smaller capacity syringes for dispensing allergens and larger capacity syringes for dispensing excipients/diluents. In exemplary embodiments, some or all of the syringe pumps may have a capacity of about one milliliter. Graduations or other indicia on the syringe pumps may be used to set and/or permit visual measurement of loaded/delivered fluid volumes.

C. Valves

Valves generally include any device for controlling the velocity (including the starting and stopping) and/or direction of flow of biological fluids within the dispensers. The valves may be controlled manually, with or without -driven assistance (such as a solenoid operated by a switch), and/or automatically (such as with an electronic controller and a solenoid). Exemplary valves may include angle, ball, butterfly, check (to restrict reverse flow), diaphragm, flipper, gate, globe, needle, pinch, slide, and/or stop cock valves, among others. Exemplary valves alternatively and/or in addition may include two-way, three-way, four-way, and/or higher-order way valves, capable of receiving and/or directing fluid from any suitable or desired directions, and/or numbers of directions.

In some embodiments, the valve(s) of a dispenser may be controlled, operated, and/or adjusted by movement of a pump. The pump movement may be driven manually (that is, by hand) and/or with a motor. The movement may be pivotal (e.g., see Examples 1 and 5) and/or translational (e.g., to operate a slide valve). Furthermore, the movement may involve the entire pump (see Examples 1 and 5) or a component of the pump (e.g., operation of check valves (see Example 2)). If a component of the pump is involved, the direction, extent, and/or rate of movement may determine how the valve(s) are controlled, operated and/or adjusted.

D. Dispenser Housings

The dispensers also may include a dispenser housing in which (and/or to which) a conduit structure, a pump, a valve, and/or an outlet may be at least partially disposed (and/or connected). The dispenser housing may include coupling structure that permits attachment of the dispenser to the dispensing system. The dispenser housing also may have a number of other functions (such as guiding/restricting operation of the pump and/or valve; protection of the conduit structure, pump, and/or valve, from contamination, damage, inadvertent uncoupling, etc.; and/or providing a site for sterilization; among others). Accordingly, the dispenser housing may include any suitable number of openings to permit access to the conduit structure (particularly the outlet and/or inlet conduits), pump, and/or valve, and/or to permit conduits and/or conduit regions to extend from the dispenser housing. The dispenser housing also may support a supply vessel, for example, by receiving the supply vessel in an opening defined by the dispenser housing.

The dispenser housing may define any suitable compartment. In some examples, the compartment may be substantially enclosed. In any case, the dispensing system may be configured to impart a positive pressure to the compartment using treated air (e.g., filtered air from a blower unit; see Example 3). Furthermore, the temperature of the air may be controlled or modified (e.g., cooled) to control or modify the temperature of the compartment.

E. Additional Features

Each dispenser may include one or more additional features such as at least one switch, sensor, driver, data input mechanism, display, controller, sterilizer, and/or indicia, among others.

The switch may include any mechanism for selecting a configuration and/or operating condition of a dispenser. The switch may be actuated manually (operated by hand or any part of the human body (such as a foot)) and/or automatically (not manually). The switch thus may be mechanical, electrical, optical, piezoelectric, and/or the like. The switch may control the operation and/or configuration of any suitable dispenser mechanism, such as a pump(s), valve(s), sensor, driver, data input mechanism, display, controller, and/or sterilizer, among others. Further aspects of switches are described elsewhere in the present teachings, such as in the Examples 1, 2, and 4-6, among others.

The sensor may include any mechanism for sensing an aspect of a dispenser. The aspect may be related to pump operation, valve position, fluid flow rate, temperature, etc. Further aspects of sensors are described elsewhere in the present teachings, such as in Section VI and in Examples 5 and 6, among others.

Drivers, data input mechanisms, displays, controllers, and sterilizers are described elsewhere in the present teachings. Drivers, data input mechanisms, and displays are described, for example, in Section VII and Example 6, among others. A controller may be a system controller or a dispenser controller dedicated to a particular dispenser, among others. Controllers are described, for example, in Section VII and Examples 5 and 6, among others. Sterilizers are described, for example, in Example 4, among others.

The dispenser housing, another portion of the dispenser station, and/or the associated system housing may include indicia that identifies the biological fluid dispensed by the dispenser station. The indicia may include one or more alphanumeric characters (such as letters, words, and/or numbers), symbols, pictures, a color code, a bar code, an electronic code (such as data on a readable electronic chip (e.g., a Radiofrequency Identification (RFID) tag), and/or the like. These indicia may be used to verify and/or track the type of material (biological material) associated with the dispenser, before and/or after dispensing. In some cases, the indicia may be removable (such as one or more preprinted or custom printed stickers) and/or scanable/readable (such as by an optical or radiofrequency reader) to facilitate compiling a record of dispensed materials.

V. Housings

The dispensing systems described herein may include one or more housings to hold dispenser stations and their supply vessels. Each housing may protect the supply vessels from ambient conditions and/or may organize and/or adjustably position the dispenser stations (and/or their supply vessels and/or dispensers), among others.

The housing may have suitable size and shape. The housing may be large enough to hold any suitable number of dispensers and supply vessels. Portions of the dispensers (such as the housings, pumps, valves, and/or outlets) may be disposed substantially outside (or substantially inside) the housing. The housing may hold the supply vessels substantially (or completely) in an interior compartment(s) defined by the housing. The interior compartment may be a chamber (or chambers) that can be substantially closed to the outside. The housing may be generally circular (or cylindrical), polygonal, and/or the like.

The housing may define a plurality of openings to receive supply vessels. At least a subset of the openings may be configured to receive supply vessels, conduits, and/or portions of the dispensers. The openings may be configured to receive the supply vessels from below, above, and/or from the side(s) of the housing. The openings may be disposed adjacent the side walls of the housing, so that the supply vessels and dispensers are positioned around a central axis of the housing. Alternatively, or in addition, the openings may be disposed in one row or in a plurality of generally parallel rows. In some examples, openings of the housing that are not in use may be covered with a plug or a cap, among others, to restrict air flow through these openings. In some examples, one or more openings of the housing may be configured to receive a cooling device, electrical or fluid conduits, and/or the like.

The housing may be connected to a support structure (a base) that supports the housing. The base may have any suitable height, such a relatively taller base to provide a floor-supported system, and/or a relatively shorter base to provide a table-top system, among others. The housing may be fixed or movable relative to the support structure. A fixed housing may be mounted fixedly on the support structure, for example, a housing with legs affixed to the housing. A movable housing may be coupled to a support structure so that the housing and its connected dispensers can be moved in relation to the support structure and in relation to an operator of the dispensers. The housing may move rotationally (e.g., turn) and/or translationally (e.g., slide). Translational movement may include linear reciprocation and/or orthogonal movement, among others. In some examples, only a portion of the housing may be movable, such as a portion connected to a subset (or all) of the dispensers.

The housing may be formed of a set of sub-housings each configured to hold a plurality of supply vessels. In some examples, the sub-housings may be removable modules that can be added to, or removed from, the system, to increase or decrease the number of supply vessels that can be received by the combined system housing. The sub-housings may be configured to be fixed or movable in relation to one another. If movable, the sub-housings may be configured to move translationally (e.g., horizontally and/or vertically) and/or pivotably in relation to one another. In some embodiments, the sub-housings may share the same pivot axis. The sub-housings may be arranged vertically (e.g., stacked) and/or horizontally relative to one another. The sub-housings may have the same size or different sizes. For examples, the sub-housings may be stacked vertically, with each sub-housing down the stack having a decreased diameter relative to the sub-housing above it. Further aspects housings with movable sub-housings are described elsewhere in the in the present teachings, such as in Example 7.

The housing may have any suitable composition. In some examples, the housing may be formed at least partially of a substantially transparent material, so that the interior compartment(s) of the housing and its contents may be examined visually from external the housing. In some examples, the side walls of the housing may be transparent. In some examples, the housing may be configured to restrict entry of light into the housing. Accordingly, the housing may include one or more transparent, colored or darkened walls, and/or one or more opaque walls. These materials may be selected according to any suitable criteria, e.g., to be biologically inert, easy to clean, difficult to break, and so on.

VI. Thermal Control Systems

The dispensing system may include a thermal control system to regulate temperature within the system. The thermal control system may regulate the temperature of any suitable components of the system including supply vessels, dispensers, receiver vessels, the housing, and/or regions thereof.

The thermal control system may include a cooling and/or heating device(s) and a heat (temperature) sensor(s), among others. The cooling/heating devices and sensors may be present at any suitable ratio. For example, the system may include the same or a different number of cooling/heating devices and sensors. In some examples, the system may include sets of one or more cooling/heating devices and one or more sensors that function together to provide individual temperature control for thermally isolated regions of the system.

The cooling and/or heating device(s) may operate by any suitable conductive, convective, and/or radiative mechanism. Exemplary cooling and/or heating devices may include peltier devices, resistive heating elements, fans, condensers, compressors, coolers based on water flow, lamps, etc.

The temperature sensor (or sensors) may have any suitable structure and may be a contact or noncontact device. Exemplary temperature sensors may include thermocouples, thermistors, resistance temperature devices, radiation thermometers (pyrometers), thermal imagers, (liquid in glass) thermometers, and/or the like.

In some examples, the dispensing system may include a thermoelectric cooling device that operates according to the Peltier effect. Such a thermoelectric cooling device may reduce condensation while refrigerating an interior compartment(s) of the housing holding one or more supply vessels, thereby minimizing damage to, and/or detachment of, labels, and/or growth of microorganisms, among others.

VII. Controllers

The dispensing systems described herein may include one or more controllers. Each controller may be configured to monitor and/or control aspects of operation of a dispensing system.

The controller may include digital instructions and processing capabilities. For example, the controller may include a processor to perform data manipulation. The controller also or alternatively may include a memory to store instructions that may be used by the processor and/or to store other data received or generated by the controller.

The controller may include any suitable input (and/or output) interface(s) for receiving (and/or outputting) data. Exemplary input (and/or output) interfaces may include a user interface, a network connection, a port for removable storage media, a sensor interface, a reader interface, a printer interface, and/or the like.

The user interface (such as a mouse, joystick, keyboard, keypad, buttons, switches, touchscreen, etc.) may permit a user to input data, such as instructions, formulas for mixtures to be created, and/or preferences for dispensing. The user interface alternatively or additionally may include a screen, one or more indicator lights, etc., to output instructions, progress indicators, and/or data, among others, to the user, such as a record of dispensing operations, status reports, warnings, etc.

The sensor interface may provide communication with any suitable sensor(s). The controller may be in communication with one or more sensors configured to sense any suitable aspects of a dispensing system. Such aspects may include temperature, light intensity, humidity, gas composition, position of the housing, fluid levels in supply vessels, pump positions, valve positions, and/or the like. Such aspects also may include the types and/or volumes of fluids dispensed, the timing and/or order of the dispensing, and so on. The controller may store, display, and/or otherwise output data about sensed aspects, for example, to maintain a record of the sample and sample preparation.

In some examples, the sensor interface may place the controller in communication with one or more temperature sensors of the system. Accordingly, the controller may be configured to receive and/or store temperature data provided by the sensor(s), so that the controller can monitor one or more temperatures within the system (e.g., regulated with distinct thermal control units (see Example 2)). The controller thus may be configured to provide a temperature control record, to document temperature stability and/or to detect any variations in the regulated temperature over time. In some examples, the biological fluids may be temperature sensitive such that temperature stability during their storage may be important. Accordingly, a temperature control record stored by the controller may provide a quality assurance for biological fluids stored in the system house, may facilitate identification of biological fluids that should be replaced due to lack of temperature stability in the system, and/or may signal a technical problem in the thermal control system, among others.

In some embodiments, the sensor interface may provide communication with a pump sensor, to monitor and/or provide feedback about pump operation (e.g., see Example 5).

The reader interface may provide communication with any suitable type of reader, such as an optical reader (e.g., a barcode scanner), a radiofrequency reader (e.g., a Radiofrequency IDentification (RFID) tag reader), and/or the like. The reader interface may be suitable, for example, to identify and track a receiver vessel (with a barcode or RFID tag) before, during, and/or after dispensing to the receiver vessel, to input data about a supply vessel, to track inventory, to record lot numbers, and/or the like.

The controller may be configured to provide any suitable information processing capabilities. For example, the controller may provide automatic computation of an immunizing dose for a human subject. The computation may be based on data about the subject's immunization history data that is accessible to the controller. Alternatively, or in addition, the controller may provide automatic computation of a suitable extract formula (e.g., types and ratios of extracts) for an immunotherapy patient based on test (e.g., skin or RAST) data from the patient. In some embodiments, the controller may be configured to provide an operator of the dispensing system with information regarding an inputted extract formula, such as incompatibilities between extracts, total glycerin concentration in the mixture, redundant antigens that could be eliminated, cost, outdate times, etc.

VIII. Drivers

The dispensing system may include one or more drive mechanisms (drivers) to guide and control movement within the system. The drive mechanism may include one or more motors and a mechanical linkage that couples operation of the motor(s) to movement of a load. The load may be the system housing, a sub-housing within the housing, one or more receiver vessels, one or more supply vessels, the dispenser and/or a component thereof, and/or the like.

Any suitable motor(s) may be used in the drive mechanism. Each motor may be an AC or DC motor, or may be air-powered, among others. Exemplary motors may be single or multiphase, induction, servo, synchronous, universal, and/or gear motors. The motor may rotary or linear. In exemplary embodiments, the motor may be a stepper motor.

The drive mechanism may employ any suitable linkage to the load. Exemplary linkages may include a belt(s), a chain(s), a gear(s), a screw(s) (e.g. a worm gear), a cable(s), a pulley(s), a rod(s), rack and pinion, and/or the like. The linkage also may include a guide structure or track that directs and/or facilitates sliding movement of the load. Accordingly, the guide structure or track may include bearings or other elements that promote sliding.

IX. Methods of Operation

The dispensing systems described herein may be suitable for performing methods of dispensing biological fluids, particularly to form mixtures of the fluids. In some examples, the biological fluids may be allergens, that is, allergen extracts or synthetic allergen compounds at any suitable dilution. The methods may include any suitable combination of the following steps, or other steps, performed any suitable number of times, in any combination, and in any suitable order. These steps may be planned and selected before and/or during dispensing. In some cases, the steps (including the types and/or amounts of fluids dispensed) may be determined by standalone and/or associated software. Such software-determined steps may be provided in any suitable format, such as a printout, a series of software prompts, and so on.

A single biological fluid or a mixture of biological fluids to be prepared may be identified or selected. In some examples, the mixture may be defined based on allergen sensitivity testing. Identification or selection of the mixture may identify or select a set of biological fluids to be included in the mixture and volumes/dilutions/concentrations for each fluid of the set (or for a single fluid). This step of identification or selection also may select a volume(s) of diluent(s) and/or excipient(s) to be included in the mixture (or to be combined with the single biological fluid). In some embodiments, the step of identification or selection may be performed by a controller of a dispensing system. For example, the controller may receive data corresponding to the types and volumes of fluids to be dispensed to create a mixture, such as through a user interface and/or other data transfer mechanism (a network, removable storage media, etc.). In some examples, the controller may determine a suitable mixture of allergens for a subject using an algorithm and test data (such as data from a skin or RAST test) from the subject.

A dispensing apparatus may be selected and readied for operation. In particular, supply vessels holding the biological fluids of the set (and, optionally, supply vessels holding other biological fluid that are not in the set) may be connected to dispensers of the dispensing apparatus. The supply vessels may be disposed in a refrigerated compartment of the dispensing apparatus and/or may be protected from light.

One of the fluids of the set may be selected. Selection may include a step of moving a dispenser (connected to a supply vessel holding the fluid selected), so that the dispenser is more conveniently positioned relative to a person operating the dispensing apparatus. The step of moving may include turning, and/or inducing translational motion of, a housing to which the dispenser is connected.

A measured volume of the selected fluid may be transferred from its supply vessel to a receiver vessel. The step of transferring may be performed by passing a portion of the selected fluid through a closure of the supply vessel and/or the receiver vessel, and may be performed with the supply vessel continuously connected to its dispenser. Accordingly, the step of transferring may be performed as the measured volume remains within a substantially closed environment, under relatively sterile conditions. Transfer of the measured volume may be monitored automatically by a controller coupled to a sensor to provide feedback to an operator or other interested parties about the accuracy of manual transfer by the operator. Accordingly, automated monitoring of manual dispensing may reduce errors, may provide verification that a mixture was prepared correctly, and/or may document the size of deviations in volumes dispensed from predefined target volumes.

The step of transferring may include a step of loading a pump with a biological fluid and a step of delivering the biological fluid from the pump to a receiver vessel. In some examples, the step of loading a pump may be performed by placing the pump in fluid communication with a supply vessel connected to the pump, and then operating the pump to draw a portion of the fluid into the pump. The pump may be used to load a predefined volume that is substantially delivered to the receiver vessel. Alternatively, the pump may be used to load a volume that is larger than the volume delivered to the receiver vessel, so that only a portion of the loaded volume is delivered. In some examples, the step of delivering the biological fluid may include a step of placing the pump in fluid communication with a receiver vessel and/or a step of operating the pump to release biological fluid to the receiver vessel. In each case, the step of placing the pump and/or the step of operating the pump may be performed manually or automatically.

Additional biological fluids of the set may also be selected and transferred. Transfer with different dispensers to the same receiver vessel may be performed at different times (generally, sequentially) or at the same time (for example, by providing two or more outlets with tubing long enough to reach the receiver vessel at the same time).

A biological fluid and/or a mixture of biological fluids dispensed to a receiver vessel may be injected, after dispensing, into a human subject, such as an allergy patient. Accordingly the fluid and/or mixture may be dispensed under conditions that minimize contamination with microorganisms. Generally, the biological fluids, the supply vessels, the receiver vessels, and the fluidic mechanism of each dispenser and/or components thereof thus may be supplied in a sterile condition, for example, supplied in a package that has been sterilized. Alternatively, the vials, the fluidics mechanism, and/or components of the fluidics mechanism may be supplied with interior compartments sterilized (and exterior surfaces nonsterile). In any case, the vials and fluidics mechanism of each dispenser station may be supplied in a sterile condition internally.

X. EXAMPLES

The following examples describe selected aspects and embodiments of the present teachings, including exemplary dispensing systems and components thereof. These examples and the various features and aspects thereof are included for illustration and are not intended to define or limit the entire scope of the present teachings.

Example 1

Dispensing System I

This example describes a first exemplary dispensing system for creating an allergen mixture for immunotherapy by transferring measured volumes of allergen stocks from stock vials to a patient's vial; see FIGS. 8-18.

Figure 8:
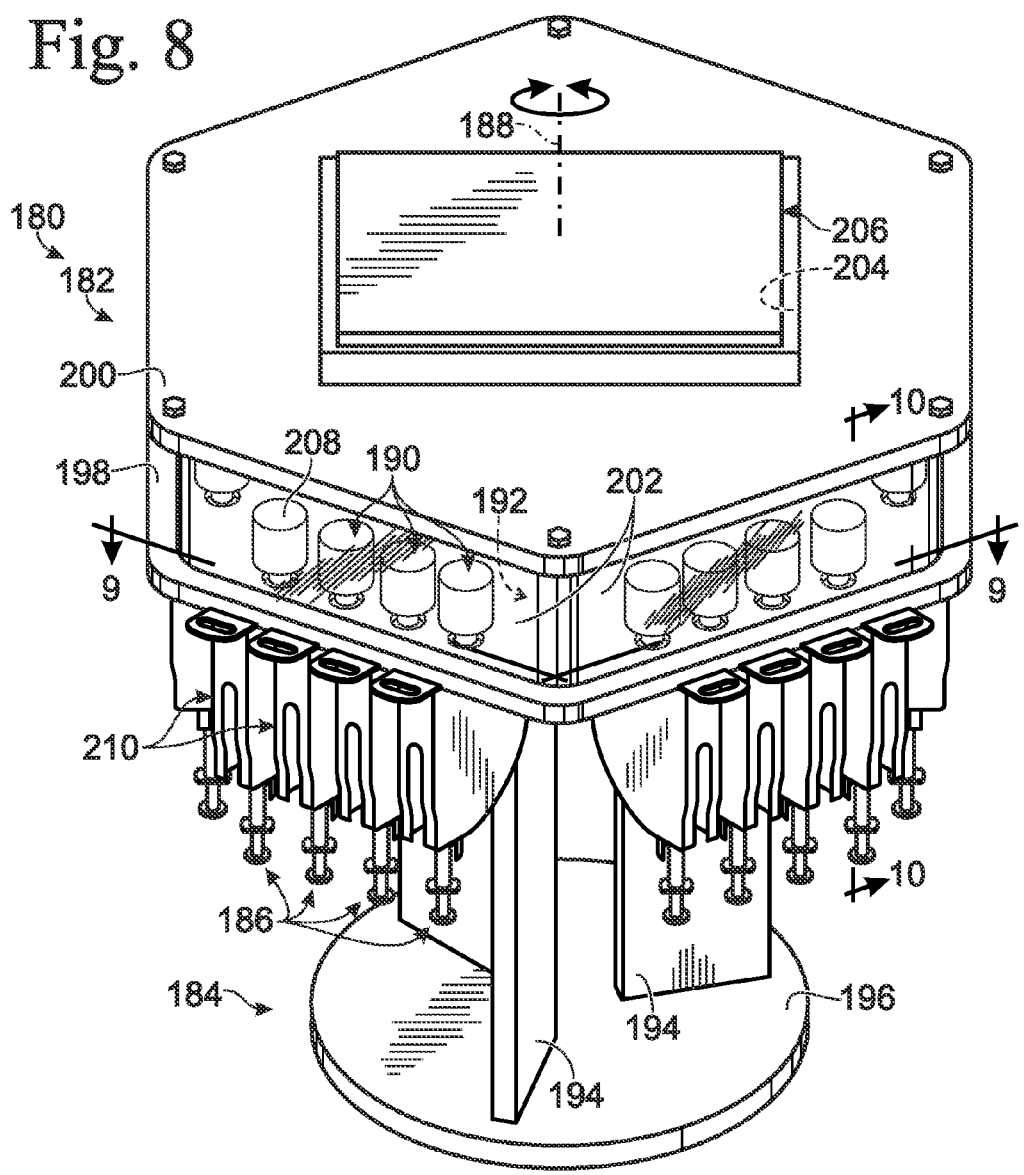
FIG. 8 is a perspective view of an example of a system for dispensing measured volumes of biological fluids between vials under relatively sterile conditions, in accordance with aspects of the present teachings.

FIG. 8 show an exemplary system 180 for preparing mixtures of allergens and/or other biological fluids. The system may include a housing 182, a base 184, and a plurality of dispenser stations 186, among others.

The housing 182 may be coupled pivotably to a base 184 so that the housing can turn around pivot axis 188. Accordingly, the housing may function as a carousel to provide adjustable access to allergen stocks 190 disposed in an interior compartment 192 defined by the walls of the housing. The base may include legs 194 mounted on, and extending upwardly from, a platform 196.

The housing may include any suitable structure. For example, the housing may include a bottom wall 198, a top wall 200, and a plurality of side walls 202 extending between the bottom and top walls. The bottom and top walls may be opaque or transparent, and the side walls may be transparent, and may be darkened to restrict access of light. Accordingly, the side walls may be formed of plastic and/or glass, and other portions of the housing may be formed of any suitable material including plastic, metal, composite, glass, and/or the like.

The housing 182 may include an opening 204 formed in top wall 200. The opening may be sized to receive a cooling device 206, such as a thermoelectric cooler operating by the Peltier effect. The cooling device may be configured to refrigerate the interior compartment 192 and the allergen stocks 190 housed in this compartment. In some examples, the cooling device may be disposed inside the housing or disposed exterior to, and/or spaced from, the housing. If exterior to the housing, the cooling device may be connected to the housing by one or more ducts.

Each dispenser station 186 may include a stock vial 208 holding an allergen stock 190 (or a vessel holding another fluid, such as a diluent, excipient, drug, etc.). The stock vial may be disposed in an upright or inverted configuration, among others, in the dispenser station. In the present illustration, the stock vials are inverted.

Each dispenser station 186 also may include a dispenser unit 210 attached to the housing and connected to a stock vial. The dispenser unit may be mounted to the bottom wall of the housing. Alternatively, or in addition, the dispenser unit may be mounted to a side wall(s) and/or the top wall.

Figure 9:
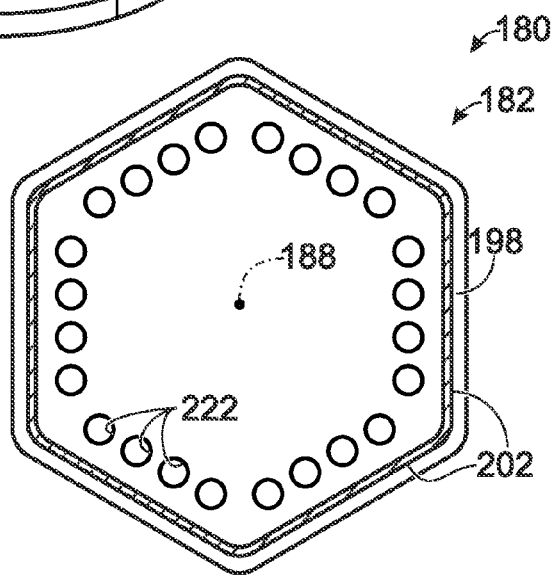
FIG. 9 is a sectional view of the system of FIG. 8, taken generally along line 9-9 of FIG. 8, in the absence of supply vials.

FIG. 9 shows a sectional view of system 180, taken generally along line 9-9 of FIG. 8, in the absence of stock vials and their allergen contents. Housing 182 may include a plurality of apertures 222 formed in the bottom wall 198 of the housing. Each aperture may be configured to receive a stock vial and/or a portion (or all) of a dispenser unit 210. In some examples, the housing may be configured to receive the stock vial and/or dispenser unit from underneath the housing. Alternatively, the stock vial (and/or the dispenser unit) may be placed into (or through) the housing from above the bottom wall, such as through the large opening 204 in the top wall or through a door and/or opening formed in a side wall.

Apertures 222 may be disposed generally around the pivot axis 188 of the housing, inward of the side walls and generally adjacent the perimeter of the bottom wall. Accordingly, the apertures may be disposed in a circular pattern, in a polygonal pattern (angularly disposed sets of rows, such as the hexagonal pattern in the present illustration), in a single row or a set of parallel rows, and/or the like.

FIG. 10 shows a partially exploded, sectional view of selected portions of the dispensing system 180, taken generally along line 10-10 of FIG. 8. An upper portion of the dispenser unit 210 may be received in an aperture 222 formed in the bottom wall 198 of the housing. Stock vial 208 thus may be disposed in the interior compartment 192 of the housing 182. In particular, the dispenser unit 222 may include a frame 223 (the dispenser housing) having a collar or flange 224 extending from a neck portion 226 of the frame. The flange may be received in a lower counterbore 228 of the aperture 222 that is widened relative to an upper bore 230 of the aperture. The flange may engage a shoulder 232 formed at the junction of the bore and counter, to restrict upward movement of the dispenser unit. In some examples, the lower counterbore may be sized and shaped so the flange 224 fits closely into the lower counterbore, so that lateral movement of the flange (and the dispenser unit) is restricted (see FIGS. 10 and 12).

The dispenser unit 210 may be secured to the housing 182 with a retainer 234. The retainer may be received, shown in phantom outline at 235, in a slot 236 formed in the bottom wall 198 of the housing and accessible from the perimeter of the bottom wall. The slot 236 may be sized and positioned so the retainer 234 may slide into the slot and under flange 224 of the dispenser unit. Downward movement of the flange (and the dispenser unit) thus may be restricted by engagement of the flange with the retainer. A lip 238 formed adjacent the slot 236 may restrict downward motion of the retainer 234.

FIG. 11 shows a top plan view of the retainer 234, taken generally along line 11-11 of FIG. 10. The retainer may be generally planar with an aperture 240 that may be engaged with a hand for insertion or removal of the retainer. The retainer also may include a distal opening 242 configured to extend around the neck portion 226 of the dispenser unit, below the flange 224 (see FIGS. 10 and 12).

FIG. 12 shows a sectional view of the dispensing system, taken generally along line 12-12 of FIG. 10, with the retainer fully inserted into the slot 236. Stock vial 208 and dispenser unit 210 are shown in phantom outline to simplify the presentation.

FIG. 10 shows the neck portion 226 of the dispenser unit may define an opening 252 in which the neck of the stock vial may be received (see FIG. 13 also). A shoulder 254 formed on the body of the stock vial may engage a rim of the neck portion 226 of the dispenser so that the stock vial may be supported by and rest on the dispenser unit, for example, in the inverted configuration shown in the present illustration. As a result, the allergen stock disposed in the stock vial may be positioned adjacent the closure of the stock vial, which may permit a greater proportion of the allergen stock to be dispensed from the stock vial.

FIG. 13 shows the dispenser station 186 of the dispenser system 180 with a portion of the frame 223 of the dispenser unit 210 removed. Frame 223 may be formed from a single piece or material, or from two or more pieces. In the present illustration, frame 223 includes left-side and right-side components 272, 274. The left-side component 272 is visible in FIG. 10, and the right-side component 274 is shown in FIG. 13. The left-side and right-side components may fit together, for example, with integral pins 276, 278 of the right-side component 274 received in corresponding sockets formed in the left-side component. The left-side and right-side components, when fitted together, may define a shell or dispenser housing that substantially encloses other components of the dispenser unit 210.

The dispenser unit 210 may include a valve 282, a syringe 284, and a delivery needle 286. Valve 282 may be configured to provide adjustable fluid communication between the stock vial 208, the syringe 284, and the delivery needle 286. The valve may be a stock cock valve, among others.

The valve may be connected to the stock vial with a flexible conduit 288 secured to a hollow needle 290. The hollow needle 290 may extend through a septum 291 of the stock vial, to place the fluid contents of the stock vial in fluid communication with the valve 282. The flexible conduit 288 and/or the hollow needle 290 may be attached to a vial retainer 292, configured, for example, with a pair of wings 294 The wings 294 may be long enough that they cannot pass easily through the opening 252 of the neck portion, shown at 296. Accordingly, the vial retainer may help to hold the stock vial in the opening 252 of the neck portion and/or to hold the flexible conduit 288 inside the frame 223 of the dispenser unit. A vent tube 297, such as a hollow needle of small diameter, also may be placed through the septum 291 of the stock vial. The vent tube may function to permit passage of gas into/out of the stock vial, but to restrict passage of liquid out of the stock vial through the vent tube 297.

The valve 282 may be coupled to the syringe 284 by any suitable mechanism. For example, the syringe may be connected to the valve by a flexible conduit. Alternatively, the valve may form a rigid connection with the valve. In the present illustration, the valve housing 298 may form a socket 302 in which a tip 304 of the syringe may be received. The socket 302 and/or the tip 304 may be tapered to facilitate forming a seal between the valve housing and the syringe tip, and/or to permit the syringe to be mated with the housing removably. Alternatively, the syringe may be connected to the housing by, for example, a threaded and/or a Luer-lock coupling.

The valve may be coupled to the delivery needle 286 by a rigid or flexible connection. For example, in the present illustration, a base 306 of the delivery needle 286 may be secured to the valve housing 298, so that the disposition of the delivery needle may be defined by the disposition of the valve housing. Delivery needle 286 may be protected by a sheath or sleeve 308 that reduces exposure of the exterior of the needle to contact with air, liquid, or solid structures, and thus to potential contamination. The sheath or sleeve may be resilient, so that the sheath can be retracted to expose the distal end of the needle. Alternatively, the sheath may be segmented so that it can telescope to expose the distal end of the needle.

Syringe 284 may be disposed in a loading configuration, shown at 309. In this loading configuration, the syringe may be disposed vertically to provide fluid communication between the stock vial and the syringe, indicated by arrows 310. In this loading configuration, the delivery needle 286 may be out of fluid communication with both the syringe and the stock vial, so that fluid from the stock vial cannot pass directly to the delivery needle. Furthermore, the delivery needle may be substantially inaccessible within the frame 223 of the dispenser unit 210. In the loading configuration, a plunger 312 of the syringe may be drawn outward, indicated at 314, to pull a measured volume 316 of the allergen stock 190 into the barrel 318 of the syringe.

FIG. 14 shows the dispenser station 186 of the dispenser system 180 in a delivery configuration, indicated at 330. To achieve this configuration, the syringe 284 may be engaged manually and pulled and/or pushed from its vertical loading configuration 309 (see FIG. 13) to a more horizontal position (or from a horizontal to vertical position, or between any other suitable dispositions). The syringe may be rigidly connected to the valve housing 298. Accordingly, turning the syringe (by orbital movement in the present illustration), indicated at 331 in FIG. 14, may produce coupled pivoting of the valve housing about an axis 332 defined by a stem or core 334 of the valve. Accordingly, the syringe, extending radially from the pivot axis 332, may act as a handle and/or lever to pivot the valve housing and thus operate the valve. In particular, pivoting of the valve housing 298 may reposition structures connected to the valve housing, such as a proximal end 336 of the flexible conduit 288 and/or the delivery needle 286 and its associated sheath 308.

Movement of the syringe 284 to the delivery position may create fluid communication between the syringe 284 and the delivery needle 286. Accordingly, the plunger 312 may be pushed into the barrel, shown at 338, to cause the measured volume 316 of fluid to flow along a path, indicated by arrows 340, from the syringe and out of the end of the delivery needle 286, shown at 342. Prior to release of the measured volume of fluid from the syringe, a patient's vial 344 may be received through an opening 346 formed in the frame 223, and into engagement with the delivery needle 286. In particular, a septum 348 of the patient's vial may be penetrated by the tip of the delivery needle, as the sheath 308 is retracted by engagement with the septum (as the vial is moved upward). Delivery of the allergen stock from the syringe to the patient's vial may be facilitated by a vent needle 350 placed through the septum 348 of the patient's vial. The vent needle may function as described above for the vent tube of the stock vial.

Figure 15:
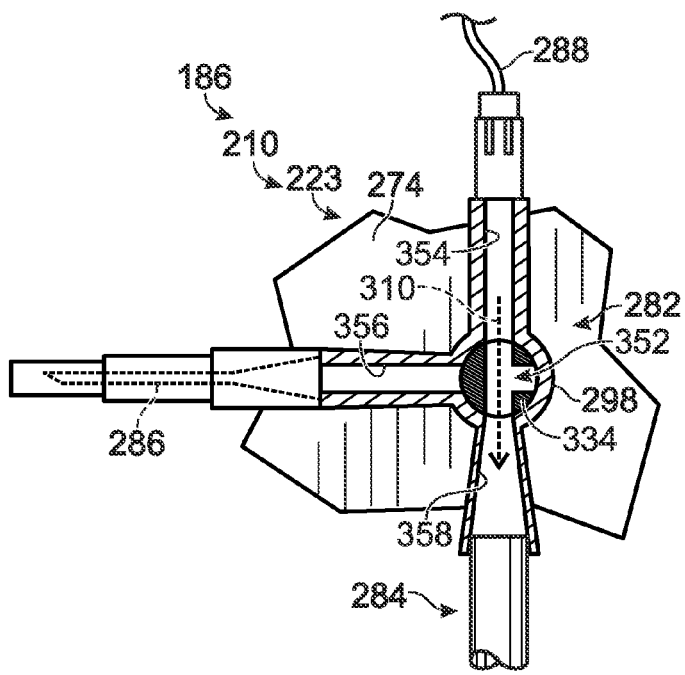
FIG. 15 is a fragmentary view of selected portions of the dispenser station of FIG. 13, particularly a valve of the dispenser station, taken generally at "15" in FIG. 13.
Figure 16:
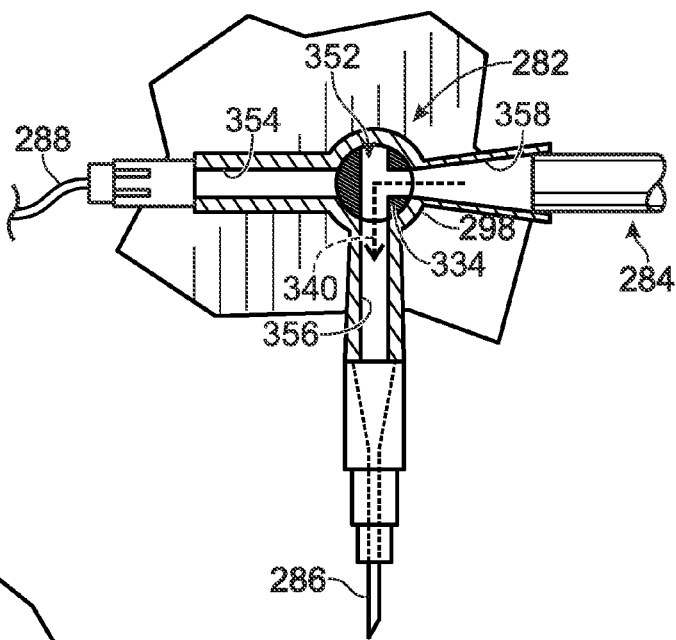
FIG. 16 is a fragmentary view of selected portions of the dispenser station of FIG. 14, particularly a valve of the dispenser station, taken generally as in FIG. 15.

FIGS. 15 and 16 shows fragmentary views of selected portions of the dispenser station 186 of FIG. 13. In particular, these figures show operation of the valve 282 of the dispenser station, viewed from a region labeled "15" in FIG. 13 for FIG. 15 (or a corresponding (unlabeled) region of FIG. 14 for the view of FIG. 16). Valve stem 334 of the valve may include a branched passage 352 (T-shaped in the present illustration) extending from a plurality of positions disposed around the perimeter of the stem. As described in more detail below in relation to FIG. 17, the passage 352 may be fixed in position, so that pairs of conduits 354, 356, 358 of the valve housing may be placed selectively in fluid communication with the passage 352 by pivoting this housing.

FIG. 15 shows the valve housing 298 in the loading configuration. Conduit 354 (connected to the stock vial via tubing 288) and conduit 358 (connected to the syringe 284) may be fluid communication with the passage 352. However, conduit 356 (connected to the delivery needle 286) may be out of fluid communication with this passage (and thus the other conduits 354, 358). Operation of the syringe 284 in this configuration may produce fluid flow along path 310 between the stock vial and the syringe 284, to load the syringe.

FIG. 16 shows the valve housing 298 in the delivery configuration. Conduits 356 and 358 may be in fluid communication with passageway 352, so that fluid can flow along path 340 from the syringe to the delivery needle 286. Conduit 354 may be out of fluid communication in this configuration, to restrict a direct flow of fluid between the stock vial and the delivery needle.

Figure 17:
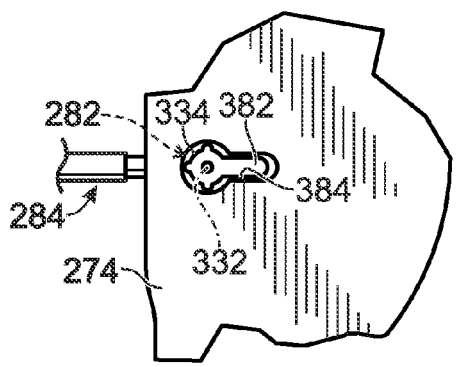
FIG. 17 is fragmentary view of selected portions of the dispenser station of FIG. 14, particularly a valve of the dispenser station, taken generally as in FIG. 16 but from an opposing (exterior) side of the housing.

FIG. 17 shows a fragmentary portion of the dispenser station, as in FIG. 16, but from an opposing side of the dispenser unit 210, with the exterior surface of right-side component 274 visible. The valve stem 334 may be substantially fixed in position (restricted from pivoting and/or translational motion) by engagement of the stem with the frame of the dispenser unit. In particular, the stem may include a projection, such as a flange or handle 382, that is received by a receiver structure or opening 384 formed in the right-side component 274 of the frame. The handle 382 may extend radially from the pivot axis 332 of the stem. Alternatively, the frame 223 may include a projection received by the stem to restrict pivoting of the stem. The left-side component of the frame also may engage the valve to prevent the valve from sliding or wobbling in the frame. For example, FIG. 12 shows an opening 386 defined by the left-side component 272 that receives an opposing side of the valve.

In some embodiments, handle 382 of the stem 334 may be operable manually. Accordingly, the dispenser station may be switchable between loading and delivery configurations by operating the handle through manual engagement of this handle. However, pivoting the valve housing through movement of the syringe, rather than pivoting the stem with direct engagement of the handle 382, may offer advantages over movement of the handle. In particular, the syringe may provide a mechanical advantage through a longer lever arm (to exert greater torque). Alternatively, or in addition, use of the syringe as a lever may provide a visual indication of individual steps of the dispensing process, based on the position of the syringe. The rate of dispensing errors thus may be reduced.

Figure 18:
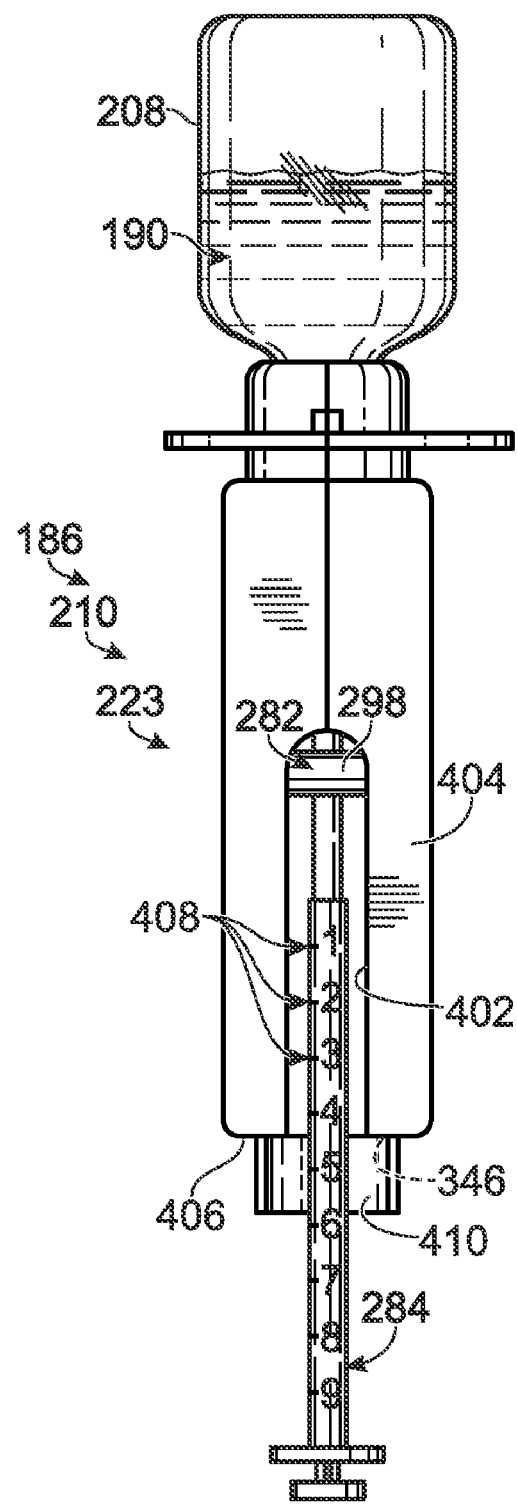
FIG. 18 is a side elevation view from the front of the dispenser station of FIG. 13, taken generally along line 18-18 of FIG. 13 with the housing assembled.

FIG. 18 shows the dispenser station 186 viewed generally along line 18-18 of FIG. 13, but with the frame 223 assembled. Frame 223 may define an elongate opening 402 extending formed vertically in a front wall 404 of the frame. The vertical opening 402 may permit the syringe to move orbitally (compare FIGS. 13 and 14), as the valve housing 298 pivots. Accordingly, the opening 402 may extend from a bottom wall 406 to a vertical position slightly above the valve 282. Opening 402 also may permit indicia 408 (such as graduations and/or numbers, among others) to be visible as fluid is loaded into the syringe. (In the present illustration, the numbers may represent tenths of milliliters.) The indicia may be configured to permit a measured volume of a biological fluid to be loaded into the syringe and/or to be released from the syringe into a receiver vial.

Vertical opening 402 may adjoin a horizontal opening 346 formed in the bottom wall 406. The horizontal or bottom opening 346 may be wider than vertical opening 402, to permit a patient's vial to be received selectively in the bottom opening (also see FIG. 14).

FIG. 18 shows the frame also may include a guide 410 disposed adjacent the bottom opening 346. Guide 410 may be configured to guide the patient's vial into the bottom opening, for engagement with the delivery needle (see also FIG. 14). Accordingly, the guide may be arcuate in shape to generally match a cylindrical contour of the patient's vial.

Example 2

Dispensing System II

This example describes a second exemplary dispensing system 510 for transferring biological fluids between closed vessels; see FIGS. 19-26.

Figure 19:
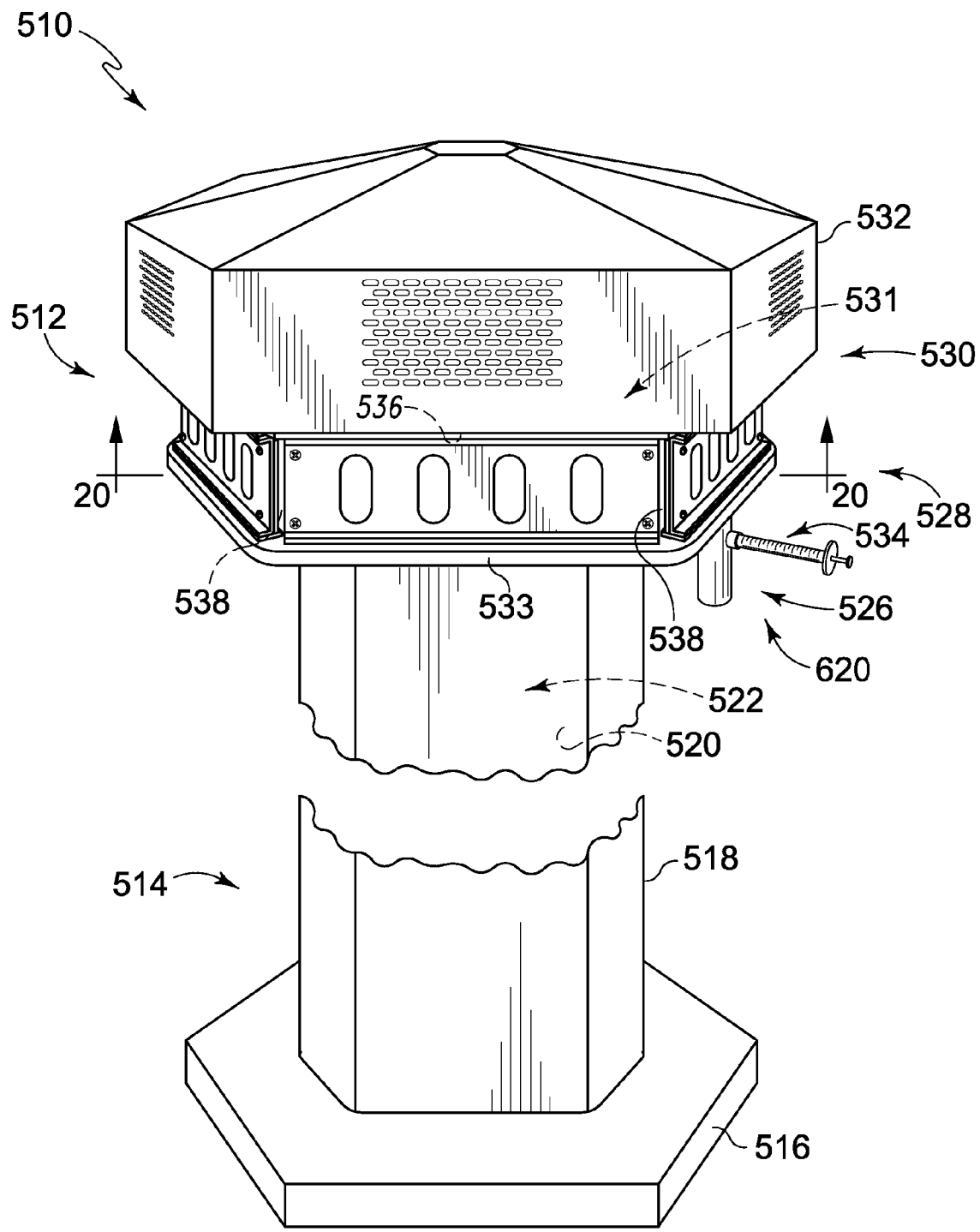
FIG. 19 is a view of another exemplary system for dispensing biological fluids, in accordance with aspects of the present teachings.

FIG. 19 shows a dispensing system 510 configured as a floor model. System 510 may be operated manually, to dispense and mix fluids, by an operator(s) standing adjacent the system and/or sitting in a chair adjacent the system, among others. The system may include a housing 512 pivotably coupled to and supported by a pedestal 514 or other support structure.

The pedestal may include a base platform 516 and a column 518 affixed to the base platform. The column may define an interior compartment 520 in which a power supply 522, electrical connectors (e.g., wires), a cooling mechanism (such as a fan), and/or other electronic and/or system components may be housed. The power supply may be configured to supply electrical power to electrically operated components disposed in housing 512. In some embodiments, the power supply may be configured to convert AC power to DC power.

Housing 512 may be structured to provide or define areas for carrying out different functions of the dispensing system. For example, proceeding from bottom to top in the present illustration, the housing may define (1) a dispensing area 526 for dispensing biological fluids to supply vessels, (2) a storage area 528 for holding and arranging the supply vessels, and (3) a thermal control area 530 including a thermal control system 531 to control the temperature of the supply vessels. Housing 512 also may include a vented cover 532 that can be removed to access components of the thermal control system.

Dispensing area 526 may be configured for mounting dispensers below supply vessels. Accordingly, the dispensing area may be a nonpartitioned, open space below the storage area that permits the dispensers to be mounted at least substantially below the housing, for example, connected to a base plate 533 of the housing. In the present illustration, only one dispenser 534 is shown mounted below the housing, to simplify the presentation. However, any suitable number of dispensers may be connected to the housing, such as four per side for a total of twenty-four in the present exemplary system. In some embodiments, the dispensing area may be partitioned by the housing, for example, with walls that extend downward from the base plate to define individual housing structures for the dispensers. Alternatively, dispenser housings may be discrete structures that are attached removably to the system housing or may not be used in the system.

Storage area 528 may be disposed generally between base plate 533 and an upper plate 536. Upper plate 536 may be mounted in a spaced relation to the base plate by column members 538 (also see FIG. 20).

Figure 20:
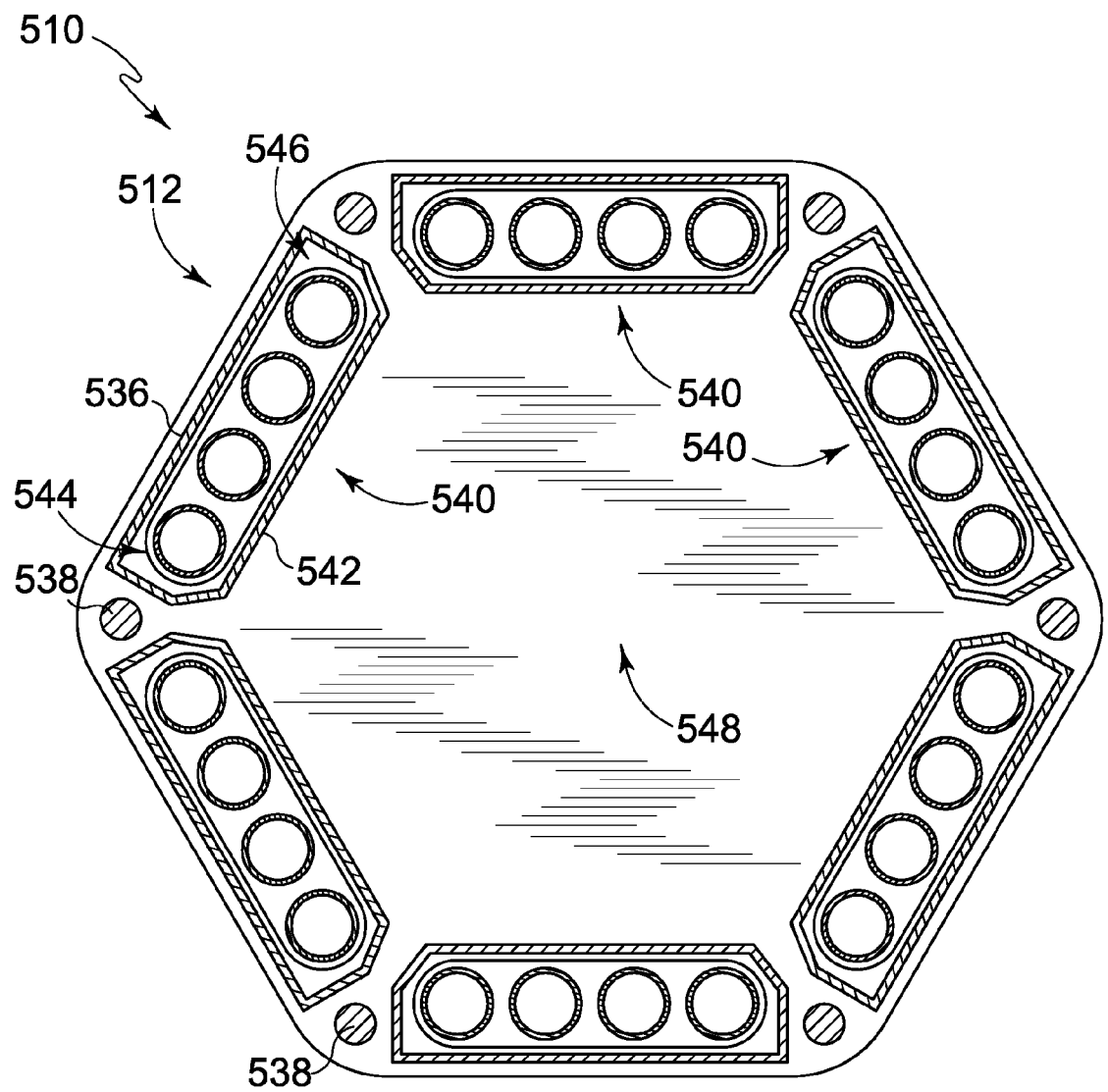
FIG. 20 is a bottom sectional view of the system of FIG. 19, taken generally along line 20-20 of FIG. 19 and showing a set of individually thermally regulated compartments each including a jacket structure for receiving supply vessels.

FIG. 20 shows a bottom sectional view of the storage area, taken generally along line 20-20 of FIG. 19. The storage area may be partitioned into a plurality of thermally isolated compartments 540 (six in the present illustration). For example, each compartment may be defined by side walls 542 that extend around a jacket structure 544 for receiving a set of supply vessels. The jacket structure may be formed of a thermally conductive material, such as metal (e.g., aluminum). A thermally insulating material may be disposed around the jacket structure in an insulator region 546 defined between the jacket structure and side walls 542. Exemplary thermally insulating materials that may be suitable include thermally insulating plastics (e.g., foam insulating plastics), nonplastics, and/or a combination thereof. Each jacket structure thus may be thermally isolated from other jacket structures disposed in the storage area, allowing individual thermal control of each jacket structure (and a set of supply vials disposed in each jacket structure). A central compartment 548 of the storage area may hold electrical conduits, electronic components of the system, and/or portions of the thermal control system, among others, and/or may remain at least substantially empty.

Figure 21:
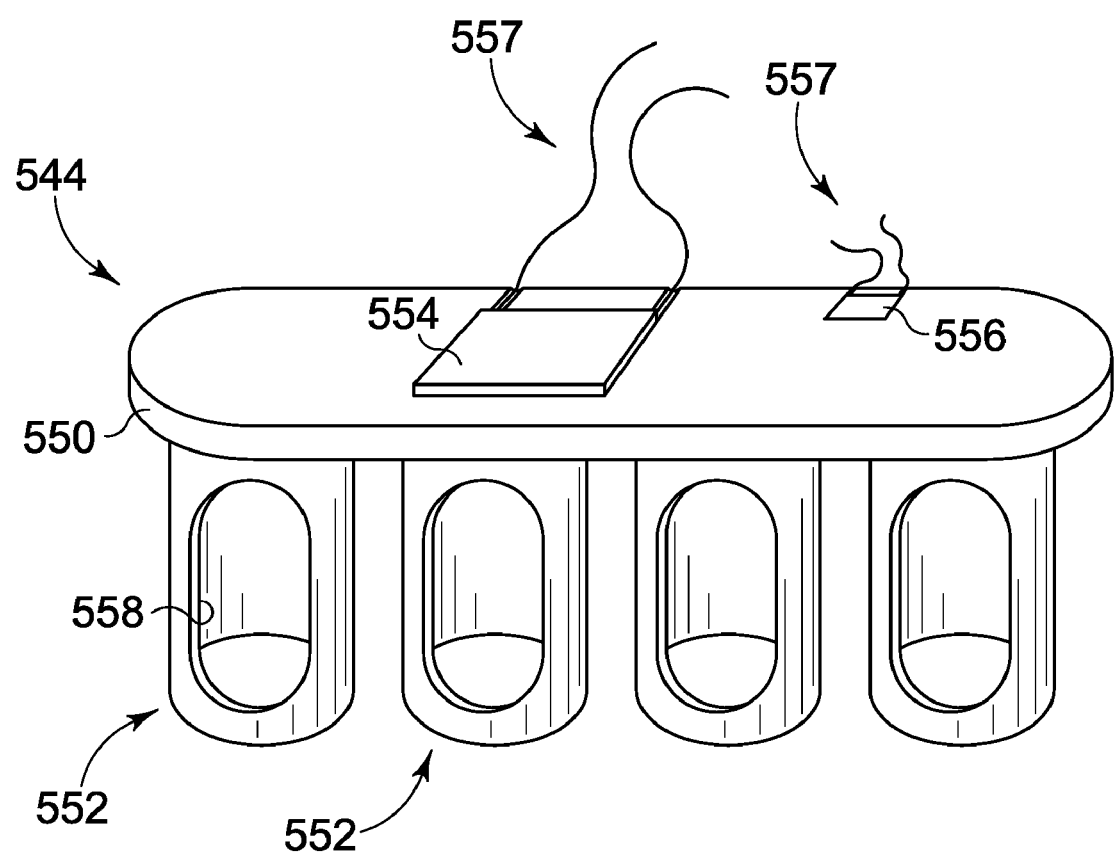
FIG. 21 is a view of the jacket structure of FIG. 20, taken generally from the side and above the jacket structure.

FIG. 21 shows jacket structure 544 generally from the side and above the jacket structure. The jacket structure may include a plate 550 and a plurality of receiver structures 552 mounted on the plate.

Plate 550 may be configured to provide heat conduction between the receiver structures. The plate also or alternatively may provide a contact (and/or attachment) site for a cooling device 554 (such as a peltier device) and a temperature sensor 556 (such as a thermistor). Each of the cooling device and sensor may include electrical conduits 557 that extend to another component(s) of the thermal control system, such as a controller (see below).

Each receiver structure may be sized and shaped for receiving an individual supply vessel. For example, the receiver structure may provide a cylindrical cavity for receipt of a cylindrical vessel. The receiver structure may be sized and shaped for a close fit between the supply vessel and the receiver structure, to promote heat conduction between the cylinder and the supply vessel. For example, the receiver structure may be sized to receive a supply vessel with a particular diameter and/or capacity, such as vessel with a capacity of about 50 mL. In some embodiments, the receiver structure also may have a length that provides contact between the bottom of the receiver vessel (inverted in the receiver structure) and plate 550. The receiver structure also may include a window 558 through which the supply vessel may be viewed, for example, so that an operator can see the fluid level and/or a label of the supply vessel from the outside of the housing. Window 558 may be an opening in the receiver structure and/or may be formed by different material, generally a transparent material, such as transparent plastic or glass. Vessels may be loaded into the receiver structures, with the vessels inverted, from below the receiver structures, such as through openings in base plate 533 (see FIG. 19)

Figure 22:
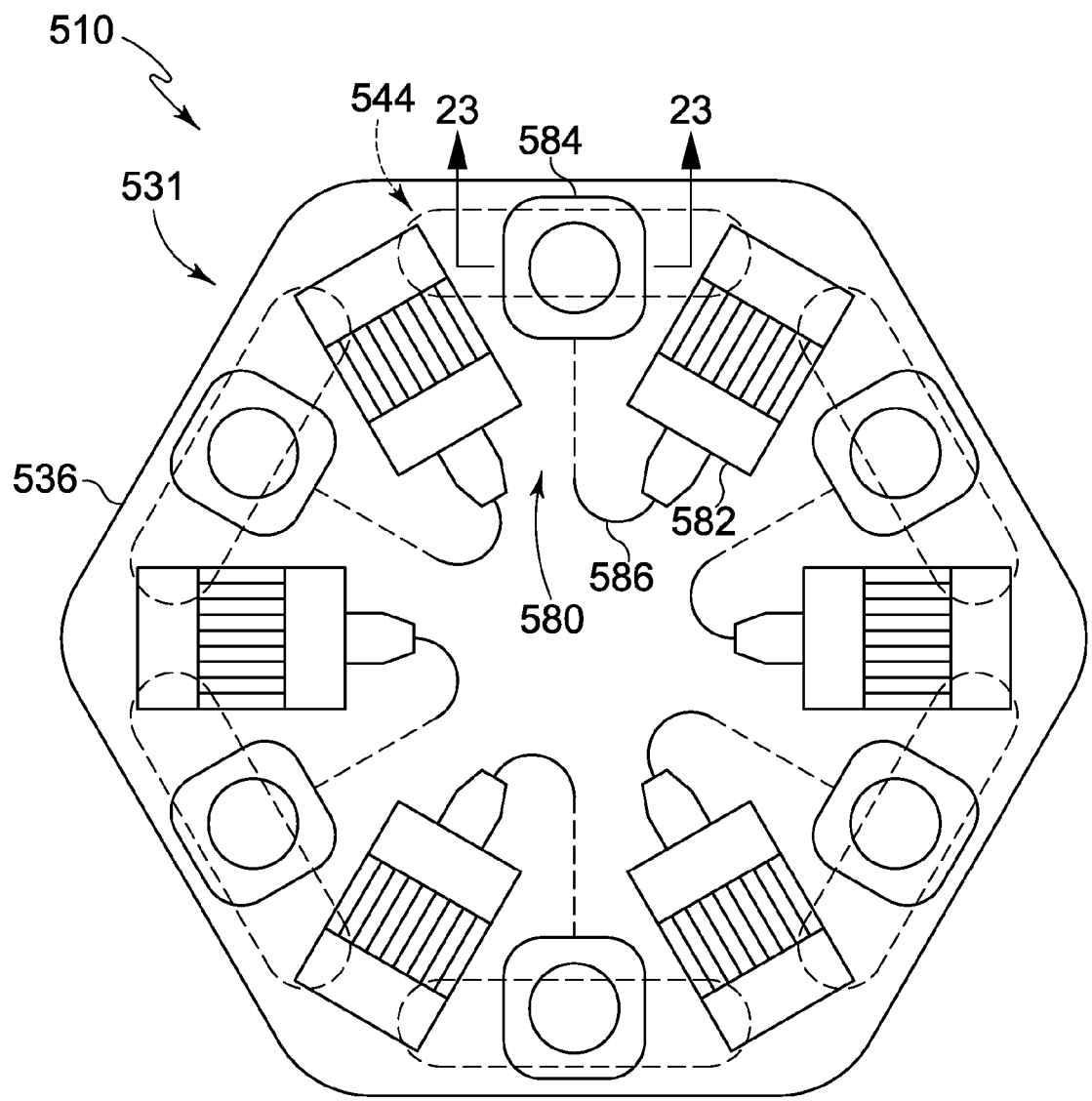
FIG. 22 is a top view of the system of FIG. 19, with the cover of the system removed such that portions of a thermal control system are visible.

FIG. 22 shows a top view of system 510 with cover 532 removed (see FIG. 19) to reveal components of thermal control system 531. The thermal control system may include a plurality of thermal control units 580 (six are shown here) that each provide temperature regulation for a distinct set of supply vessels. For example, in the present illustration, each thermal control unit is configured to control the temperature of a distinct jacket structure 544 (and thus vessels/biological fluids disposed in the jacket structure). The thermal control units thus may maintain supply vessels disposed in distinct jacket structures at the same or different temperatures.

Thermal control unit 580 may include a controller 582, a heat sink 584, a cooling device, and a temperature sensor (see FIG. 21), among others. The controller may be, for example, a PI (proportional, integral) controller, a PID (proportional, integral, derivative) controller, and/or any other suitable feedback-based controller.

The controller may be electrically coupled, shown at 586, to the cooling device, the temperature sensor, and/or heat sink 584. The heat sink may be configured to draw heat away from the cooling device and jacket structure 544.

Figure 23:
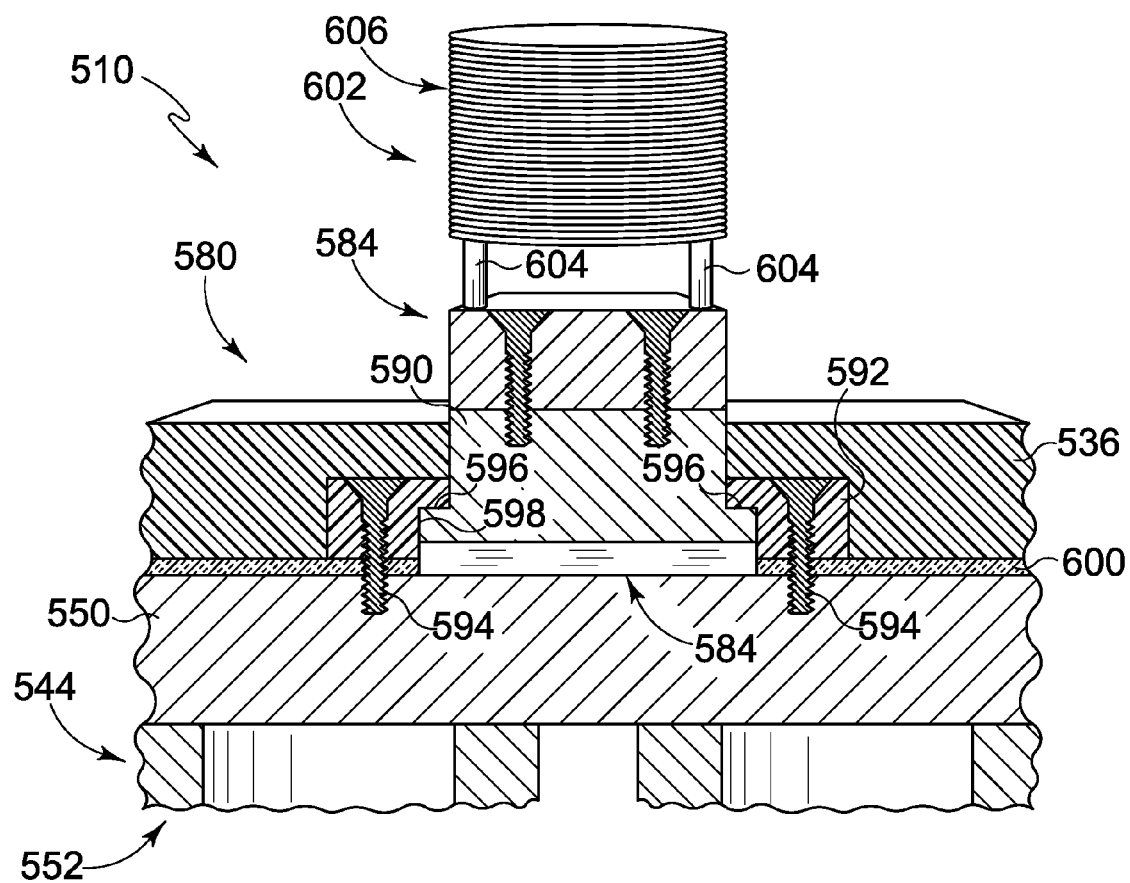
FIG. 23 is a sectional view of the system of FIG. 19, taken generally along line 23-23 of FIG. 22 and showing portions of an individual thermal control unit of the thermal control system.

FIG. 23 shows a sectional view taken through thermal control unit 580 and plate 550 (and a portion of receiver structures 552) of jacket structure 544. Peltier device 554 may be disposed between jacket structure 544 and heat sink 584. The cold side of the peltier device may engage the jacket structure and the hot side of the peltier device may engage a thermally conductive sink block 590 of the heat sink. The sink block may be formed of a thermally conductive material, such as metal (e.g., copper). The peltier device and at least a lower portion of the sink block may be surrounded laterally by a thermally insulating material, to restrict heat flow from the sink block back to the jacket structure, lateral to the peltier device. For example, an insulator member 592 may be fastened to plate 550 using fasteners 594, such that flanges 596 of the sink block engage walls of an opening 598 of the insulator member, to clamp the peltier device between the sink block and the insulator member. In some embodiments, the insulator member may be formed of a phenolic material. An insulator layer 600 also may be disposed on plate 550 to restrict lateral heat flow from the peltier device. A suitable material for layer 600 may be, for example, foamed polyvinylchloride (PVC). Further insulation may be provided by upper plate 536 (see FIGS. 19 and 20) formed of a thermally insulating material, such as polyethylene.

The heat sink may be configured to dissipate heat by conducting heat from sink block 590 to fan unit 602 via heat pipes 604. The fan unit may blow air, which has been heated by heat pipes 604, radially onto fins 606, to produce heated air, which is released from the vented cover of the housing. In some examples, the thermal control system may include one or more additional fans that promote flow of heated air out of the housing, such as a fan located centrally near the top of the housing cover. A heat sink that may be suitable for the thermal control unit is available as a P4 CPU Cooler from Gigabyte.

Figure 24:
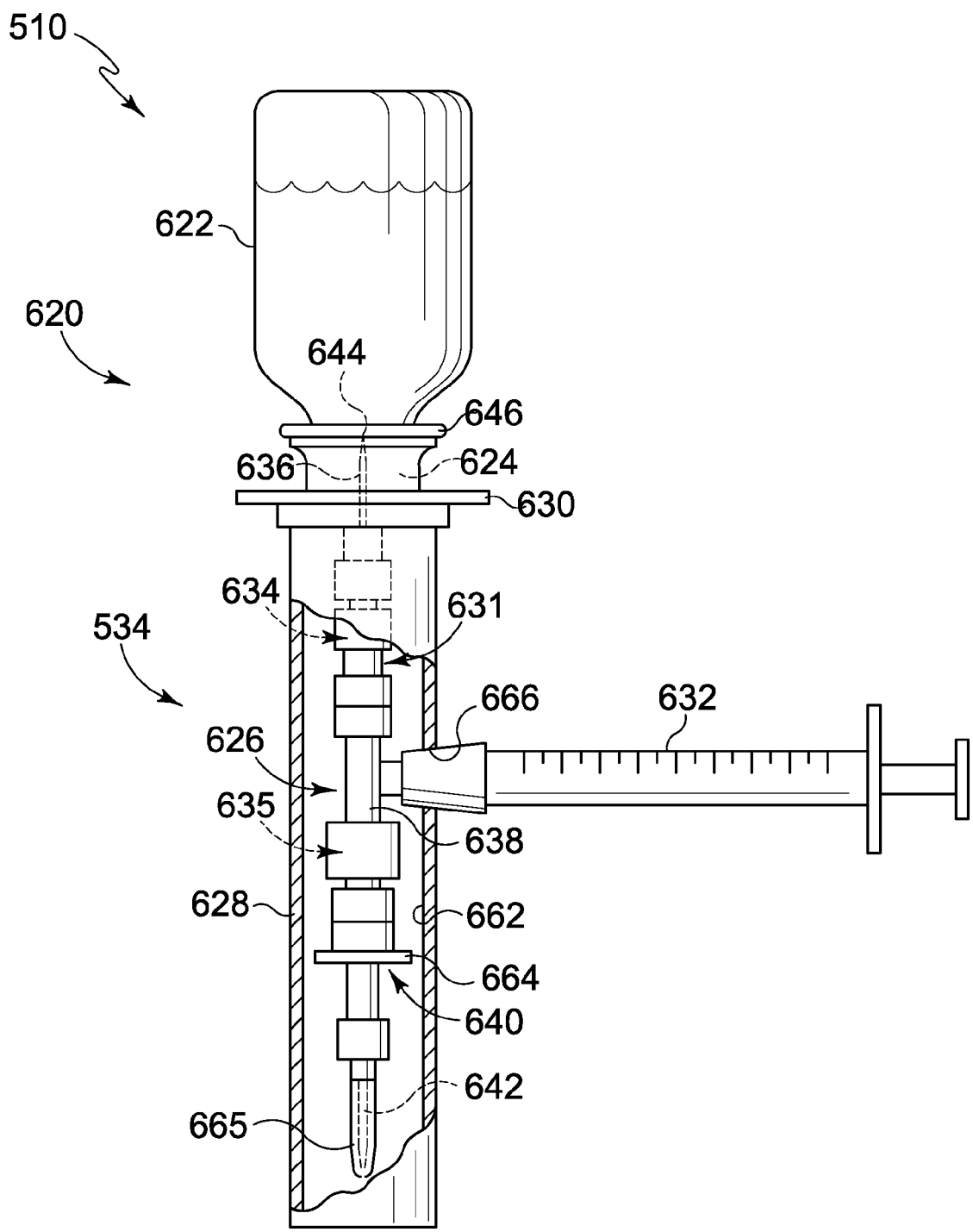
FIG. 24 is a partially sectional side view of a dispenser station from the system of FIG. 19, in accordance with aspects of the present teachings.

FIG. 24 shows a dispenser station 620 of system 510 (also see FIG. 19). Dispenser station 620 may include dispenser 534 coupled to a supply vessel 622 via sealed engagement with a closure 624 of the supply vessel. Dispenser 534 may include a fluidics mechanism 626 and a dispenser housing 628. Each of the fluidics mechanism and the dispenser housing may be attached to the system housing via a coupling member 630. The coupling member may be a plate configured to fit into the system housing from underneath the housing and may be retained in position with a retainer, generally as shown and described for collar 224 and retainer 234 of system 180 (see FIGS. 10-12).

The fluidics mechanism may include conduit structure 631, syringe pump 632, and check valves 634, 635. The conduit structure may include a plurality of discrete components or assemblies including an inlet conduit 636, a T-conduit 638, a flanged conduit 640, and an outlet conduit 642, among others. Components and/or assemblies may be connected to one another (or to the syringe pump) by any suitable connection, such as a standard or swabbable Luer-Loc coupling. A swabbable Luer-Loc coupling includes a valve that remains closed and accessible for surface treatment (such as swabbing with a disinfectant) until coupling occurs.

Inlet conduit 636 may have any suitable structure to perform any suitable functions. For example, the inlet conduit may be configured to provide a sealed coupling with closure 624. Accordingly, the inlet conduit may have a sharp tip 644 that can pierce the closure. The inlet conduit also may include a collar or ancillary cap 646 that engages, supports, and/or fits over the neck of the supply vessel.

In some embodiments, the inlet conduit may include a self-venting mechanism. The self-venting mechanism may permit air to pass through the seal between the inlet conduit and the closure, into the supply vessel, to relieve pressure differences between the supply vessel and the outside air. For example, the inlet conduit may include a widened, sloped base and projections disposed under and elevating the supply vessel. This structure may allow air flow to the sloped base, for upward movement along the sloped base and into the supply vessel. However, the inlet conduit is still in sealed engagement with the closure, to restrict the biological fluid from leaking out of the supply vessel.

The inlet conduit (or a conduit connected to it) also may be configured to engage support plate 630, for example, by extending through an opening of the support plate. The inlet conduit thus may be assembled with the support plate prior to coupling to other components of the conduit structure (and generally prior to installing the support plate in the system housing). For example, the inlet conduit may be placed through the opening of the support plate. Transverse movement of the inlet conduit relative to the support plate then may provide increased engagement between the inlet conduit and the support plate that holds the inlet conduit in position relative to the support plate.

Figure 25:
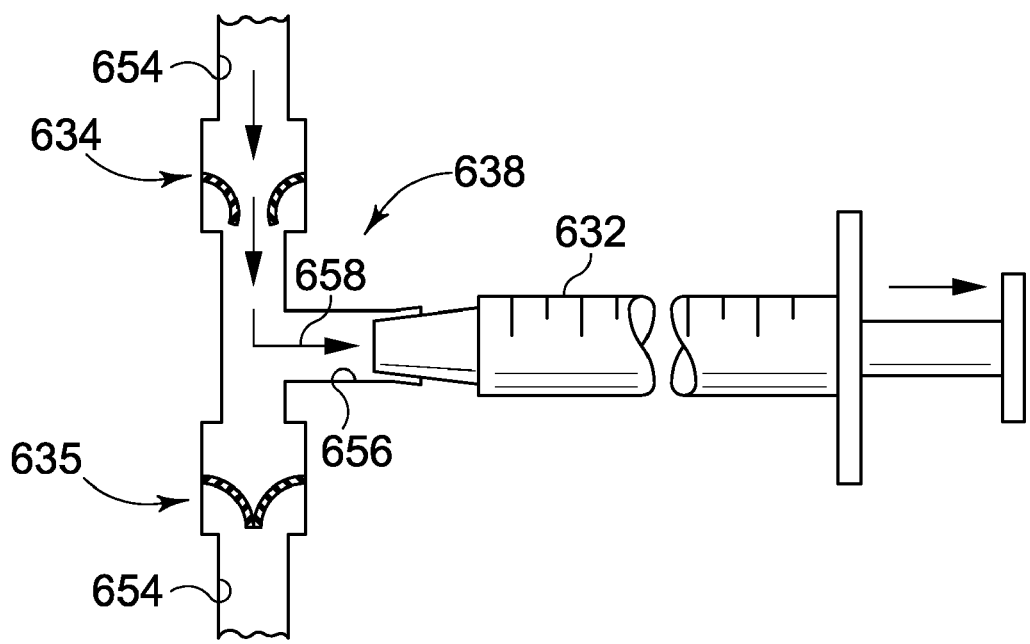
FIG. 25 is a somewhat schematic view of selected portions of the dispenser station of FIG. 24 and showing a valve configuration produced in the dispenser station as a syringe pump of the dispenser station is loading fluid, in accordance with aspects of the present teachings.
Figure 26:
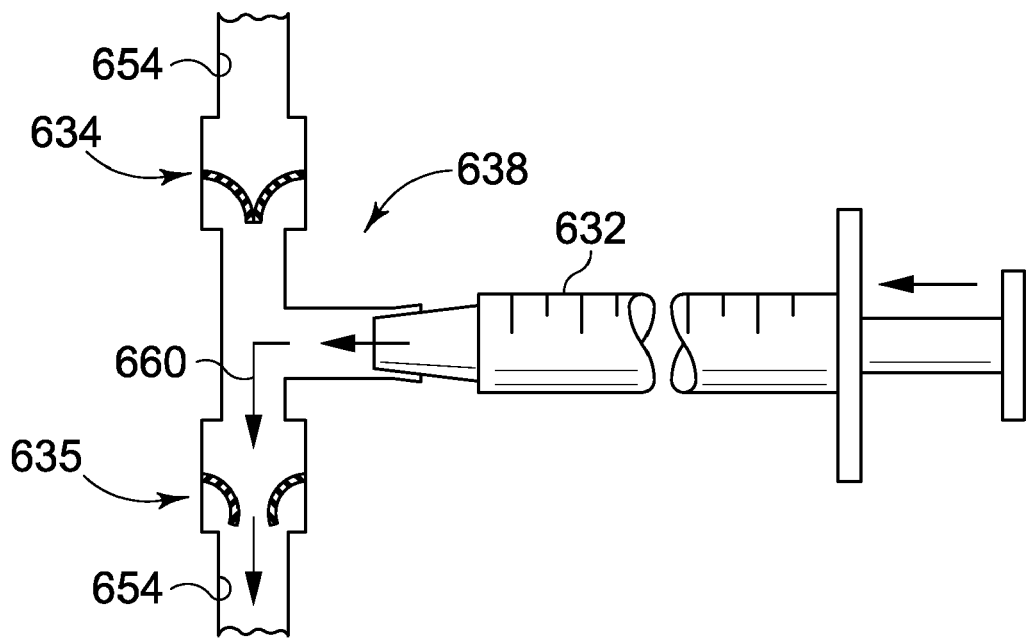
FIG. 26 is a somewhat schematic view of selected portions of the dispenser station of FIG. 24 and showing a valve configuration produced in the dispenser station as the syringe pump is delivering fluid, in accordance with aspects of the present teachings

T-conduit 638 may be configured to provide unidirectional flow of fluid along a main passage of the T-conduit. In particular, the fluid may be restricted to flow from the inlet conduit to the outlet conduit (and substantially not in reverse). In contrast, the T-conduit may permit bi-directional flow through a side passage of the T-conduit that extends to the syringe pump. FIGS. 25 and 26 illustrate schematically how check valves 634, 635 within the T-conduit restrict reverse flow in main massage 654 during loading and delivery movement of the syringe pump. Each of the check valves permits fluid flow in the same direction, from the inlet conduit to the outlet conduit, and restricts flow in the reverse direction. Outward movement of the syringe plunger produces fluid flow, indicated by arrow 658, that opens upper check valve 634 (upstream of the pump and side passage 656) and closes lower check valve 635 (downstream of the pump)(see FIG. 25), thereby loading the syringe with fluid from the supply vessel. Inward movement of the syringe plunger produces fluid flow, indicated by arrow 660, toward the outlet conduit, which closes upper check valve 634 and opens lower check valve 635 (see FIG. 26), thereby delivering fluid from the pump to the outlet conduit. Exemplary check valves that may be suitable are duckbill valves.

FIG. 24 shows additional features of the dispenser. For example, flanged conduit 640 may cooperate with dispenser housing 628 to form a substantially enclosed compartment 662 for the majority of the conduit structure. In particular, the flanged conduit may include a collar or flange 664 that extends radially from the flanged conduit towards the dispenser housing.

The outlet conduit may include an elastomeric sheath 665 that retracts as the conduit penetrates the closure of a receiver vessel. The elastomeric sheath may be, for example, a sleeve formed of silicone rubber.

The dispenser housing may have any suitable structure. For example, the dispenser housing may have a cylindrical shape with an opening 666 for receiving the syringe. The dispenser housing may mate with coupling member 630 to facilitate positioning the dispenser housing on the system housing. The dispenser housing may be formed of any suitable material, such as a transparent plastic, to facilitate viewing the fluidics mechanism, or an opaque plastic to reduce exposure of the fluidics mechanism to light, among others.

Example 3

Dispenser Station with Climate Control

Figure 27:
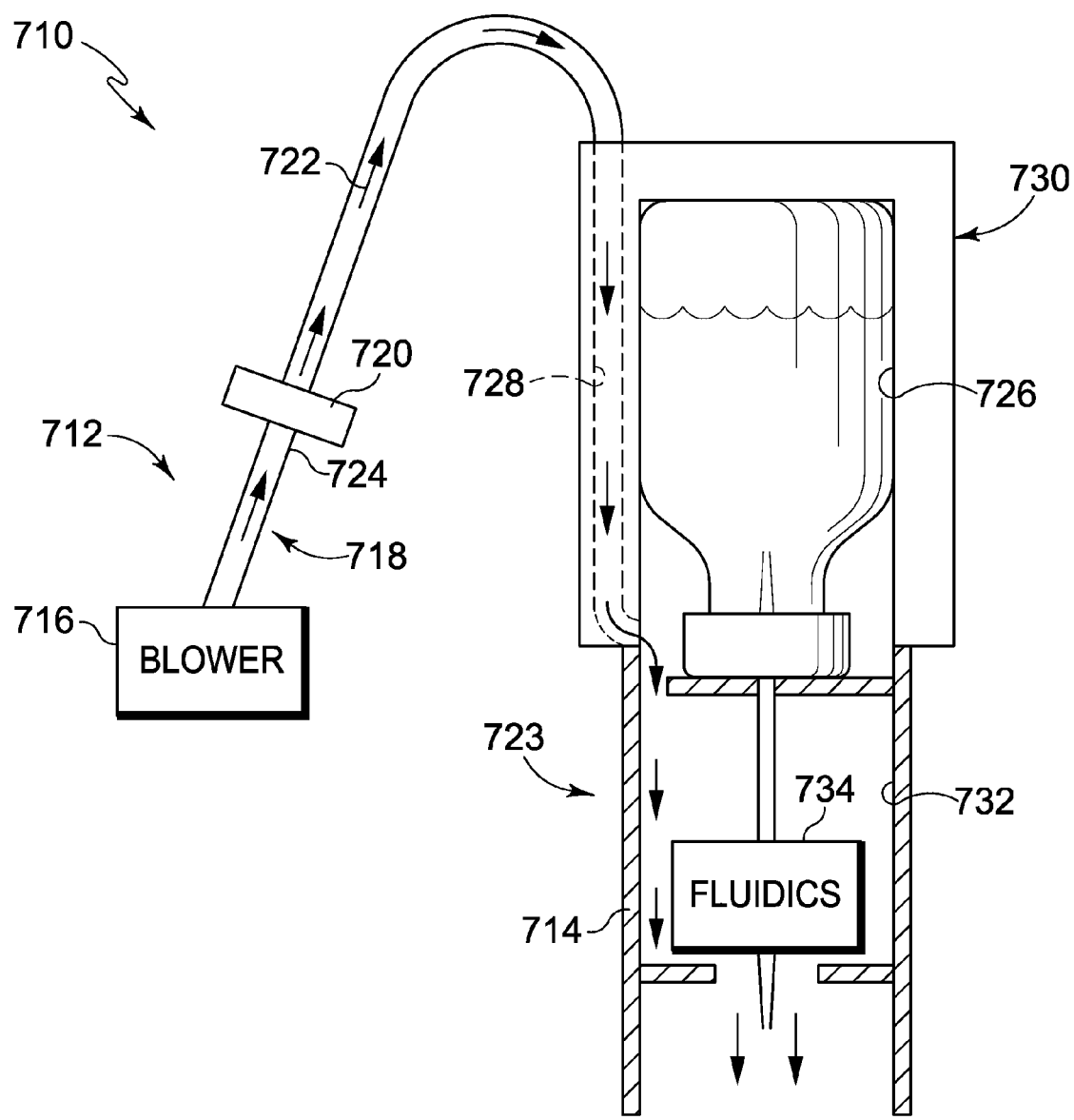
FIG. 27 is a somewhat schematic, partially sectional side view of an exemplary dispenser station including a flow system that cools and pressurizes a housing compartment of the dispenser station, in accordance with aspects of the present teachings.

This example describes an exemplary dispenser station 710 including a flow system 712 that cools and pressurizes the interior of a dispenser housing 714 of the dispenser station; see FIG. 27.

Flow system 712 may include a blower mechanism 716, a conduit structure 718, and a filter 720, among others. The blower mechanism may be configured to generate a stream of air 722 that is filtered by filter 720. The filter may be any suitable mechanism for reducing the presence of microorganisms in the air stream, such as a HEPA filter. The conduit structure may provide a flow path for the air stream that extends to dispenser 723 of the dispenser station. For example, the conduit structure may include tubing 724 that carries the air stream from the blower mechanism to the dispenser. The air stream may enter a vessel storage compartment 726 of the dispenser station. Alternatively, or in addition, the air stream may travel through a thermally conductive conduit 728 having a temperature controlled by a thermal control system. For example, the thermally conductive conduit may be created by a bore formed in a jacket structure 730 in which the supply vessel is received (see Example 2). The air stream may be cooled (or heated) as it travels along the thermally conductive conduit, according to the temperature of the jacket structure. The air stream thus may enter a compartment 732 inside the dispenser housing to cool dispenser fluidics 734. Alternatively, or in addition, the air stream may create a net positive pressure (with filtered air) inside the dispenser housing, to reduce entry of unfiltered air into the dispenser housing.

The flow system may extend to any suitable number of the dispenser stations. For example, in some embodiments, the flow system may include a manifold with conduits that extend to each of the dispenser stations, so that a filtered air stream travels to each dispenser station.

Example 4

Dispenser Station with Decontamination Mechanism

Figure 28:
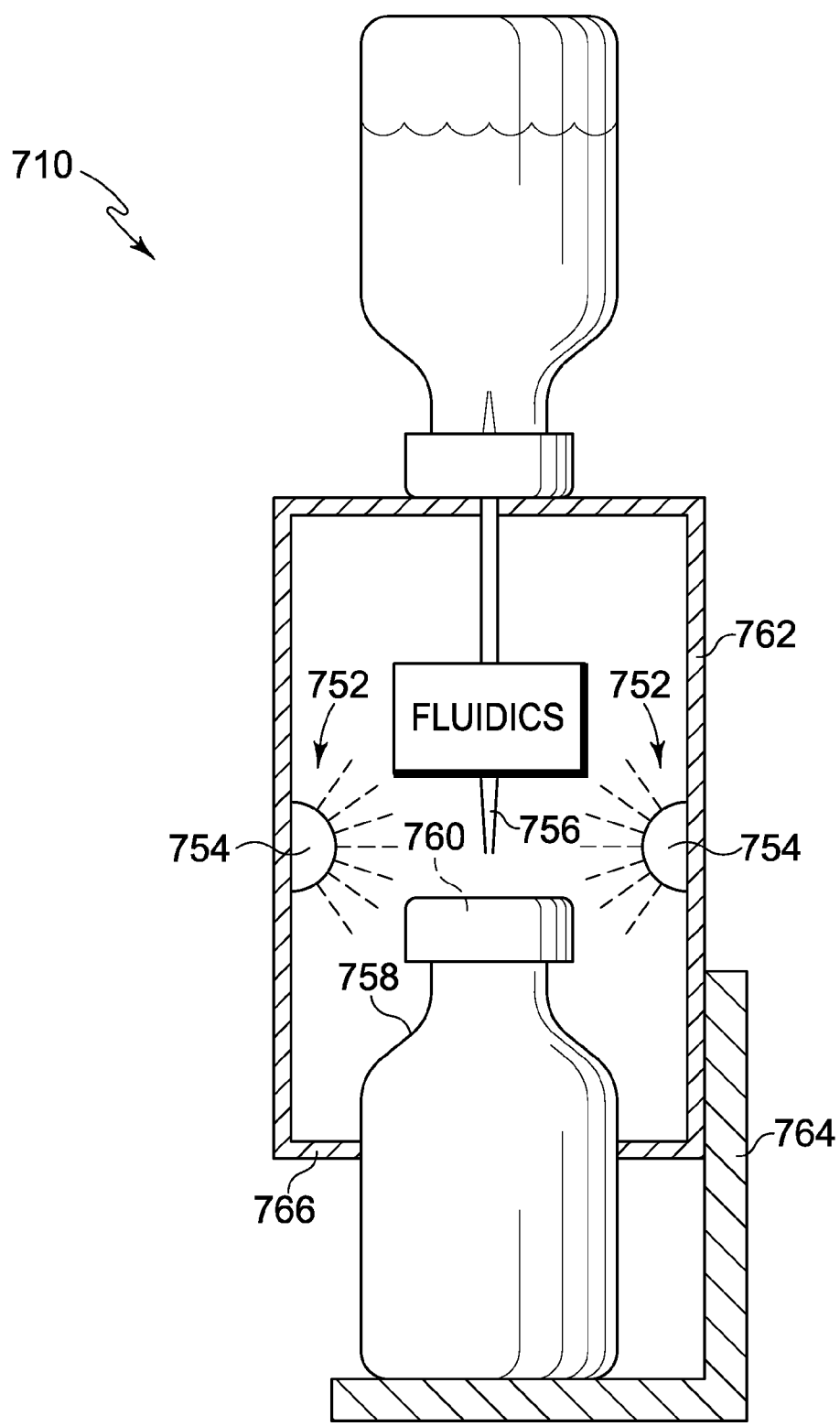
FIG. 28 is a somewhat schematic, partially sectional side view of an exemplary dispenser station including a decontamination mechanism, in accordance with aspects of the present teachings.

This example describes an exemplary dispenser station 750 including a decontamination mechanism 752; see FIG. 28.

The decontamination mechanism, also termed a sterilizer, may be configured to reduce the chance of contamination of dispensed biological fluids by killing, inactivating, and/or removing pathogens and/or other contaminants before, during, and/or after a dispensing operation. Accordingly, the decontamination mechanism may provide treatment with a chemical, electromagnetic radiation, a filter, an absorber, and/or heat, among others. Operation of a decontamination mechanism may provide any suitable calculated, statistical, and/or actual decrease in the number of viable and/or active (e.g., living, growing, dividing, infectious, and/or toxicogenic) pathogens present, within a treated field, such as a decrease to less than about a thousandth, a ten-thousandth, a one-hundred-thousandth, or a millionth of the original level (e.g., at least about a "three-log kill," a "four-log kill," a "five-log kill," or a "six-log kill"), among others. The decontamination process may be configured to take any suitable amount of time, for example, less than about a minute, less than about ten seconds, less than about one second, or less than about one-tenth of a second, among others. Exemplary pathogens may include bacteria, mold/fungi, viruses, virions, prions, and/or the like, among others.

In exemplary embodiments, the decontamination mechanism irradiates a region of the dispenser station with electromagnetic radiation, such as ultraviolet light. Accordingly, the decontamination mechanism may include one or more ultraviolet light sources 754. In addition, the decontamination mechanism optionally may include one or more optical elements, including reflective and/or refractive elements, to direct and/or intensify light, to increase the efficacy of decontamination. Each ultraviolet light source may provide a continuous or pulsed beam of light. The ultraviolet light source may produce light of a suitable wavelength(s) and intensity to kill and/or inactivate microorganisms. Killing and/or inactivation may involve any suitable mechanism(s), such as death, DNA dimer formation, denaturation, cleavage, and/or the like. In some examples, the light source may be a flash lamp or pulsed laser that delivers one or more flashes or pulses of ultraviolet light to achieve sterilization. Flash or pulsed sources may generate more light in less time, while consuming less power and producing less heat, than continuous sources. The pulses produced by a flash or pulsed source may be less than about 1 millisecond in duration, less than about 1 microsecond in duration, less than about 100 nanoseconds in duration, less than about 10 nanoseconds in duration, or less than about 1 nanosecond in duration, among others. The decontamination cycle, in turn, may involve illumination for a set period (for continuous or pulsed sources) or a set number of pulses (for pulsed sources). The light source may produce effective amounts of germicidal, ultraviolet C (UV-C) light, particularly light with wavelengths between about 100 nm and about 280 or 290 nm, more particularly between about 230 nm and about 260 nm, and yet more particularly about 245 nm, among others.

The decontamination mechanism may be configured to decontaminate (or sterilize) any suitable region(s) and/or surface(s) of the dispenser. For example, the decontamination mechanism may be configured to decontaminate an outlet conduit 756 (such as without a sheath and/or with its sheath retracted) and/or a receiver vessel 758, particularly a closure 760 of the receiver vessel. The decontamination mechanism thus may be operated at any suitable time, such as continuously, periodically, and/or a short time before delivery of a biological fluid to a receiver vessel, among others. Components of the dispenser, including supply or stock vessels, receiver or patient vessels, intervening fluid pathways, and so on, may be selected to facilitate decontamination by the selected decontamination mechanism(s). For example, vessels and/or intervening conduit may be selected to transmit ultraviolet light, for use with decontamination mechanisms based on ultraviolet light. Moreover, these components may be structured to facilitate operation of the decontamination mechanism, for example, forming a layer of fluid to increase the area available for illumination while decreasing the depth required to reach all portions of the fluid.

The decontamination mechanism may be actuated by any suitable mechanism, including mechanically, optically, acoustically (voice control), and/or automatically, among others. Mechanical actuation may be performed, for example, by a switch operated directly by a person (such as by hand or by foot (e.g., pressing a foot pedal) or indirectly by manual placement of the receiver vessel into the dispenser station. Optical actuation may be via an optical sensor that optically senses the presence of the receiver vessel. Acoustical actuation may be via a voice operated mechanism that is controlled electronically. Automatic actuation may be via a controller that actuates the decontamination mechanism at an appropriate time(s) during automated dispensing.

It may be desirable to minimize human exposure to the decontamination mechanism. Accordingly, the decontamination mechanism may be shielded by any suitable mechanism. In some examples, dispenser housing 762 may include a support structure 764 that supports the receiver vessel during operation of the decontamination mechanism (e.g., to minimize exposure to the operator's hands). In some embodiments, the support structure may function as an elevator that moves the receiver vial upward, such as into the housing and/or into engagement with the outlet conduit, before, during, and/or after actuation of the decontamination mechanism. Alternatively, or in addition, the housing may include a shield structure 766 that allows the receiver vessel to enter the dispenser housing but blocks exit of the decontamination agent (such as by blocking transmission of UV light).

A dispensing system may have any suitable number of decontamination mechanisms. For example, the system may have a decontamination mechanism for each dispenser station. Alternatively, the system may include fewer decontamination mechanisms than dispenser stations, such as a single or a few decontamination stations for use to decontaminate the tops of receiver vessels before engagement with dispensers.

Example 5

Dispenser Station with Manually Operated Pinch Valves

Figure 29:
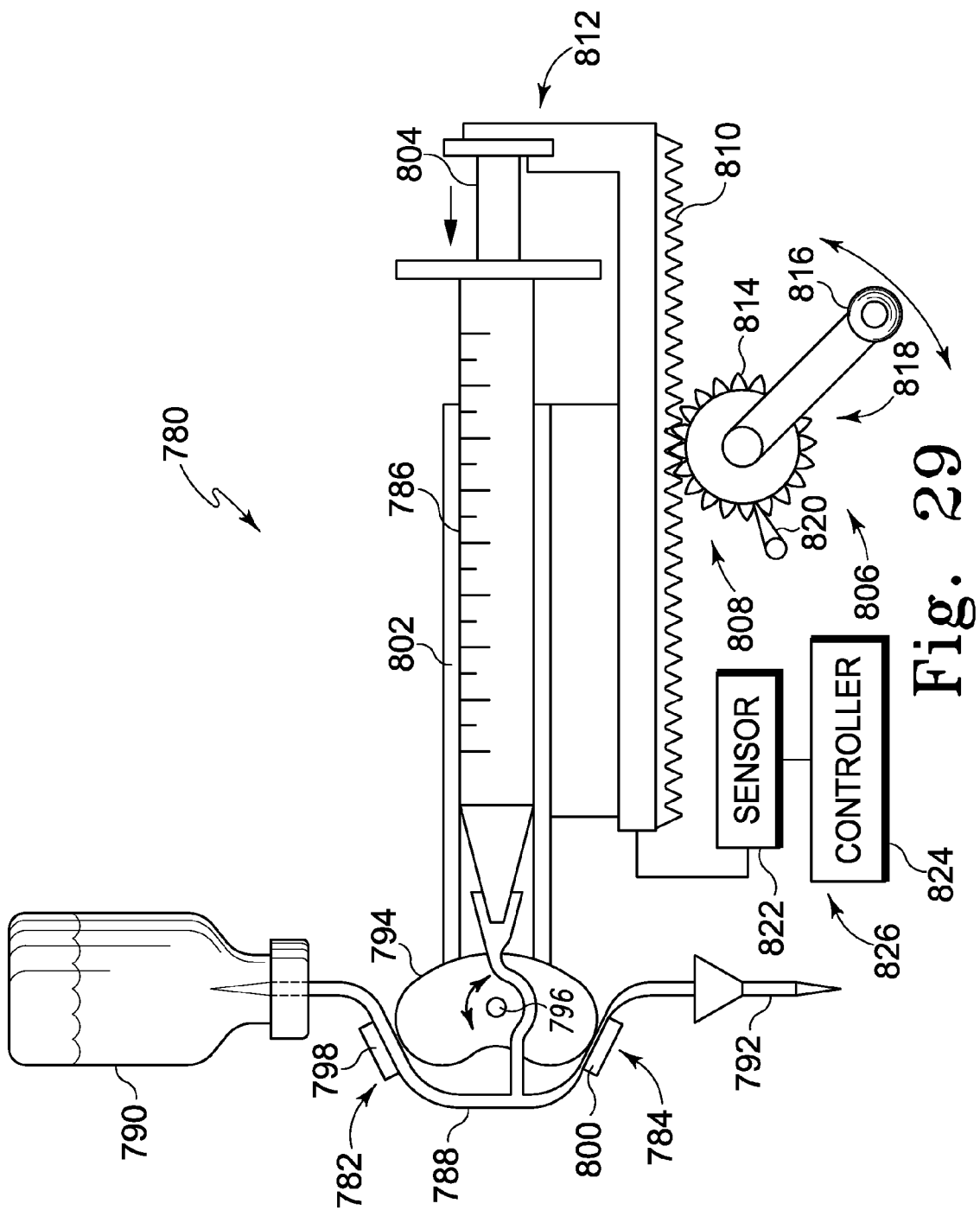
FIG. 29 is a somewhat schematic side view of an exemplary dispenser station with a pinch valve arrangement that is operated manually, in accordance with aspects of the present teachings.

This example describes an exemplary dispenser station 780 including manually operated pinch valves 782, 784; see FIG. 29.

The pinch valves may be selectively actuated by pivotal movement of syringe pump 786. Selective actuation may provide uni-directional flow of fluid along primary conduit 788, from a supply vessel 790 to an outlet conduit 792. Pinch valves 782, 784 may be formed by engagement between a pivotable cam 794 (having a pivot axis 796) and respective valve members 798, 800. Cam 794 may be affixed to a syringe receiver 802 into which the syringe pump can be mounted. Accordingly, the cam may be pivotable via pivotal movement of the syringe pump, syringe receiver, and/or associated structures. Cam 794 may be pivotable such that pivotal motion of the cam against lower valve member 800 pinches the conduit to block the delivery pathway, as shown here, thereby allowing fluid to be loaded selectively into syringe 786 from supply vessel 790. Cam also may be pivotable such that pivotal motion of the cam against upper valve member 798 (counter-clockwise in the present view) blocks the loading pathway, thereby allowing fluid to be delivered selectively through the outlet conduit.

The syringe pump may include a piston or plunger 804 operated by direct hand engagement or indirectly via a mechanical assist 806. The mechanical assist may be, for example, a rack-and-pinion mechanism 808. A rack structure 810 of mechanism 808 may be connected to the plunger handle, shown at 812, such that translational movement of the rack structure produces corresponding movement of the plunger (and vice versa). A pinion gear 814 of mechanism 808 may be connected to a handle 816 that can be engaged by hand, such that the syringe pump is operated by a hand crank 818 to move the plunger in and out. (The handle and hand crank may be omitted, so that the plunger is moved more directly by an operator.) A pawl 820 may provide a ratchet mechanism that restricts reverse movement of the hand crank, until the rack-and-pinion mechanism is pivoted away from the pawl (after loading the pump). The mechanical assist may be configured such that the plunger cannot be moved as rapidly as by direct engagement of the plunger by hand, which may, for example, reduce the formation of air bubbles in fluid lines.

Any suitable portion (or all) of dispenser station 780 may be disposable. In some examples, the syringe and its associate conduit structure may be disposable, and the remaining components (e.g., the rack-and-pinion mechanism, the ratchet mechanism, the syringe receiver, etc.) may be coupled to a dispenser housing that is reusable. Accordingly, the syringe and conduit structure may be supplied as a sterilized module or cassette that is installed in the dispenser station.

Dispenser station 780 also may use operation of the mechanical assist, and particularly operation of the rack-and-pinion mechanism, to facilitate measurement of pump operation. For example, the dispenser station may include a pump sensor 822 that measures changes in the position of the rack-and-pinion mechanism corresponding to movement of the pump plunger. Accordingly, pump sensor 822 may be, for example, a position sensor, such as a potentiometer, an encoder, and/or the like. The pump sensor may be in communication with a controller 824 to forms a feedback mechanism 826 for measuring and documenting operation of the dispenser station. In particular, the feedback mechanism may record the volume dispensed from the dispenser into a particular receiver vessel. In some embodiments, the controller may include data about the particular fluids (and thus dispenser stations) and volumes of these fluids that should be dispensed into a receiver vessel to form a predefined mixture of biological fluids. Accordingly, the controller may be configured to notify the operator of an error during dispensing, if the error in volume dispensed is too great and/or if the wrong dispenser station was operated to dispense a fluid into the receiver vessel. Each dispenser station of a dispensing system thus may include a pump sensor in communication with a system controller.

Example 6

Dispenser Station with Automated Operation

Figure 30:
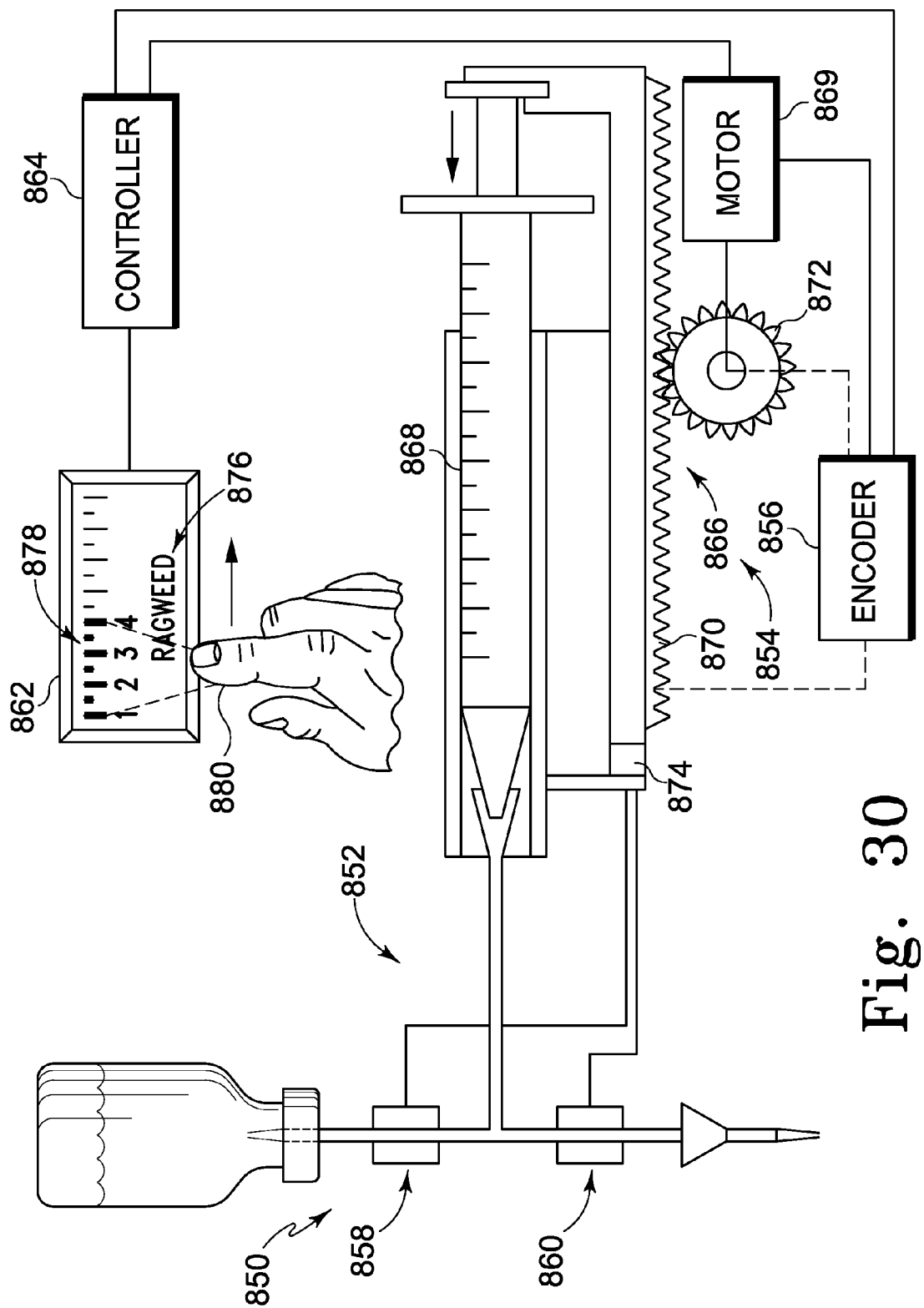
FIG. 30 is a somewhat schematic side view of an exemplary dispenser station configured to be operated automatically, in accordance with aspects of the present teachings.

This example describes an exemplary dispenser station 850 operated automatically; see FIG. 30.

Dispenser station 850 may include any suitable structure and mechanisms that drive, monitor, and/or control automated operation of a dispenser 852. For example, dispenser station may include a motor-driven pump assembly 854 that moves fluid, an encoder or other pump sensor 856 that measures operation of the pump (see Example 5), electrically actuated pinch valves 858, 860 to direct fluid flow, a touch display 862 to input and/or output data, and/or a controller 864 to control operation of the various dispenser mechanisms.

Pump assembly 854 may include a rack-and-pinion mechanism 866 coupled to a syringe pump 868, generally as described above in relation to Example 5, and a motor 869 to drive mechanism 866 (and thus operation of the syringe pump). Motor may be any suitable type of motor including a rotary or linear motor. In exemplary embodiments, the motor is a stepper motor.

Encoder (and/or a potentiometer) 856 may measure position and/or movement of the pump assembly. For example, the encoder may be a linear encoder that measures the position of a rack structure 870, and/or a rotary encoder that measures the rotational position of the motor or of a pinion gear 872, among others.

Pinch valves may be actuated by a switch 874 and/or controller 864. The switch may be disposed in a first configuration by outward movement of rack structure 870, such that valve 858 is open(ed) and valve 860 is closed when the plunger of the syringe pump begins loading fluid. The switch further may be disposed in a second configuration by inward movement of the rack structure, such that valve 858 is closed and valve 860 is open(ed). Alternatively, operation of the valves may be controlled via data from the controller to coordinate operation of the valves with operation of the motor.

Display 862 may be configured to input and/or output any suitable data. For example, the display may present (continuously, periodically, or upon demand) data about a biological fluid dispensed by a dispenser station (e.g., "ragweed" to identify the extract disposed in the supply vessel), shown at 876, and/or data about a volume selected to be dispensed, shown at 878. The display also may include touch-sensitive switches through which a user may select a volume to be dispensed by touching the display. For example, the user may slide a digit 880 along a volume scale or may touch buttons presented by the display, among others.

Example 7

System with Multi-Tiered Dispenser Stations

Figure 31:
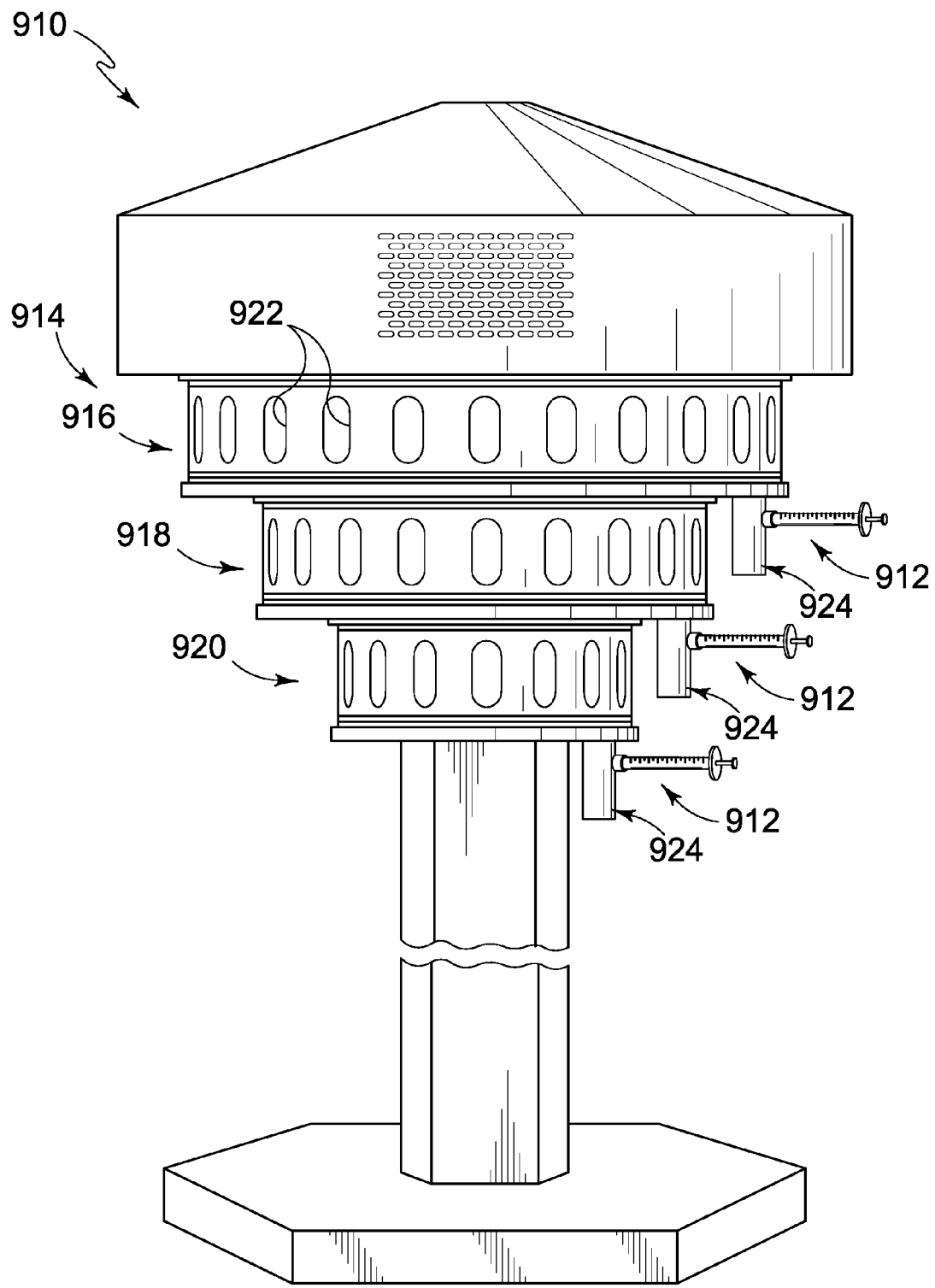
FIG. 31 is a side view of yet another exemplary system for dispensing biological fluids and including a multi-tiered arrangement of dispenser stations, in accordance with aspects of the present teachings.

This example describes an exemplary dispensing system 910 including a multi-tiered arrangement of dispenser stations 912, see FIG. 31.

System 910 may be configured to arrange dispenser stations both horizontally and vertically (in a three-dimensional array). The system may include a housing 914 with a plurality of sub-housings 916, 918, 920 arranged vertically. Each sub-housing may be configured to receive a plurality of supply vessels, which may be visible through windows 922. Dispensers 924 may be coupled to the supply vessels of each sub-housing (only one dispenser per level is shown here to simplify the presentation). The sub-housings may be pivotable relative to one another, such that each dispenser station can be accessed from the same side of the system by pivoting the appropriate sub-housing. The sub-housings may have the same diameter or may decrease in diameter towards the base of the system. Successively smaller diameters for the sub-housings may be suitable to provide space for dispensers below each sub-housing. In alternative embodiments, the dispensers may be mounted adjacent their corresponding sub-housings and/or the sub-housings may be spaced vertically from one another, to accommodate the dispensers without a decrease in sub-housing diameter.

System 910 may be configured to arrange biological fluids in any suitable configuration. For example, different tiers of the system may hold different types of biological fluids (such as different allergen extracts), biological fluids of distinct function (such as extracts on a first tier, drugs on a second tier, other additives on a third tier, etc.), and/or different dilutions of the same biological fluids (such as serial or progressive dilutions of the same extract proceeding downward (or upward) through the tiers).

Example 8

Dispenser Station with Stock Fluid Return Mechanism

Figure 32A:
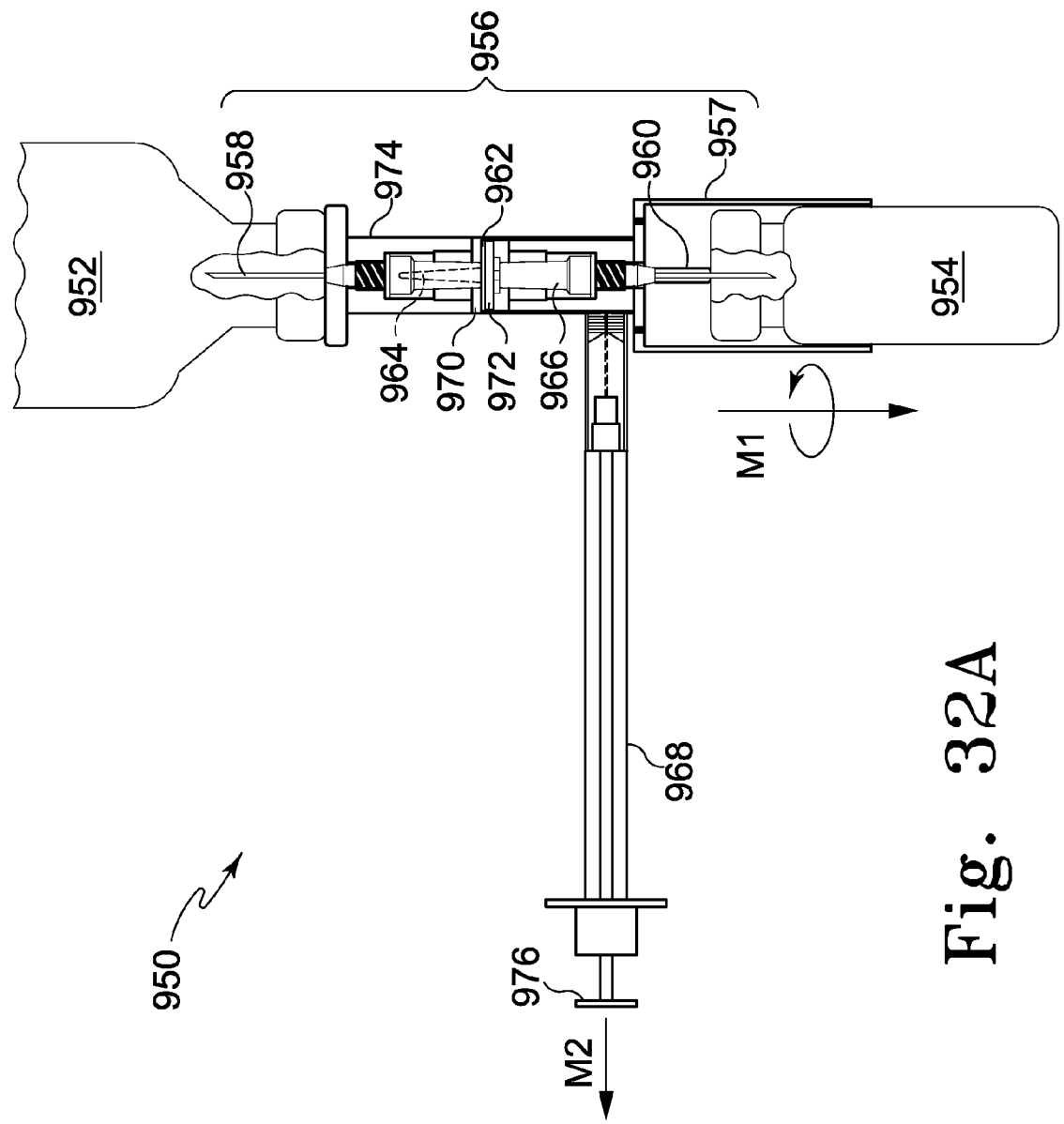
FIG. 32 is a three-panel somewhat schematic view of an exemplary dispenser station with a stock fluid return mechanism, in accordance with aspects of the present teachings. The figure shows an initial, predispense configuration (Panel A), an intermediate configuration (Panel B), and a final, postdispense configuration (Panel C).

This example describes an exemplary dispenser station 950 with a stock fluid return mechanism for returning unused stock fluid to a supply or stock vessel; see FIG. 32ABC. This dispenser station may be used, if at all, instead of, or in combination with, other dispenser stations, including but not limited to dispenser stations described elsewhere herein. The accompanying drawings show an initial, predispense configuration (Panel A), an intermediate configuration (Panel B), and a final, postdispense configuration (Panel C).

Dispenser station 950 may include a supply vessel (or stock bottle) 952, a receiver vessel (or patient bottle) 954, and a fluid transfer mechanism 956.

The supply and receiver vessels may have any suitable size and form, for example, as described elsewhere herein. The supply vessel may be used to hold and supply a supply fluid, such as an antigen stock solution, for dispensing. The receiver vessel may be used to receive and hold a portion of the supply fluid, for example, to form a patient solution, after dispensing. In some embodiments, the supply vessel may be larger than the receiver vessel; for example, the supply vessel may be about 50 mL, and the receiver vessel may be about 5 mL, among others.

The fluid transfer mechanism similarly may have any suitable size and form. Here, the transfer mechanism is configured to transfer fluid from the supply vessel to the receiver vessel, and then to return any unused fluid to the supply vessel after transfer to the receiver vessel has been completed. The transfer mechanism, in this embodiment, is based on pressure differentials that bias fluid flow in the desired direction(s). These pressure differentials may be at least about a few psi (pounds per square inch), a few tens of psi (e.g., 30, 40, or 50 psi), a hundred psi, or two hundred psi, among others. The usable pressure differential may be limited by the system's ability to maintain the differential without leaking, particularly from the upper seal around the top vessel. The system may be designed to work without exposure to, or input of, atmospheric air, reducing the likelihood of contamination.

FIG. 32A shows dispenser station 950 in an initial, predispense configuration. Supply vessel 952 contains a fluid (e.g., an allergen stock solution) to be dispensed. Receiver vessel 954 includes a volume capable of receiving the dispensed fluid, for example, into a buffer solution intended to dilute the dispensed fluid and/or mix it with other dispensed fluids from other dispenser stations.

The supply and receiver vessels are attached to transfer system 956; however, there is no direct communication between the two bottles. The supply vessel typically will be in place, and cooled, from dispense operation to dispense operation. The receiver vessel, in contrast, typically will be inserted into the system for one dispense operation (although it may previously or subsequently be used at other dispensing stations). The receiver vessel (at least) may be held in place and/or inhibited from moving at least in part by an overfitting sleeve structure 957. The supply and/or receiver vessels further may be guided onto the respective needles and/or held in place by any suitable mechanism(s), such as threaded and/or Luer lock mechanisms.

The transfer system may include (1) a supply needle 958, in fluid communication with the supply vessel, (2) a receiver needle 960, in fluid communication (although not necessary liquid contact) with the receiver vessel, (3) an intervening holding reservoir 962, shown here in a low-volume configuration, capable of receiving fluid from the supply vessel, and holding the fluid for dispensing into the receiver vessel, (4) a supply conduit 964 and a receiver conduit 966 capable of routing fluid from the supply needle to the holding reservoir, and from the holding reservoir to the receiver needle, respectively, and/or (5) a pump 968 such as a syringe pump selectively capable of interaction with fluid in the holding reservoir. The holding reservoir may be defined and bounded by a supply piston 970 and a receiver piston 972, positioned within a transfer housing 974.

The dispenser station may be prepared for transfer in two steps. First, the receiver vessel and supply vessel may be moved apart, typically by moving the receiver vessel while keeping the supply vessel fixed. For example, the receiver vessel may be moved down, or it may simultaneously be moved down and rotated, as shown at M1 in the drawing. This relative movement of supply and receiver vessels increases the volume of the intervening holding reservoir, for example, to about a few mL, to about one to three mL, or to about two mL, among others, while drawing fluid out of the supply vessel into the holding reservoir. Second, following the first step, the pump may be actuated to remove air from the receiver vessel, creating a partial vacuum that later may be used to move fluid from the holding reservoir to the receiver vessel. Here, where the pump is a syringe pump, the pump may be actuated by pulling out a plunger 976, as shown at M2 in the drawing, to withdraw air into the syringe volume. The volume of air withdrawn may be at least about the volume of fluid to be dispensed into the receiver vessel, or at least about a few times the volume of fluid to be dispensed, among others. For example, in some embodiments, the volume of air withdrawn may be about one or two mL, among others, and the volume of fluid to be dispensed may be about 0.25 or 0.5 mL, among others.

Figure 32B:
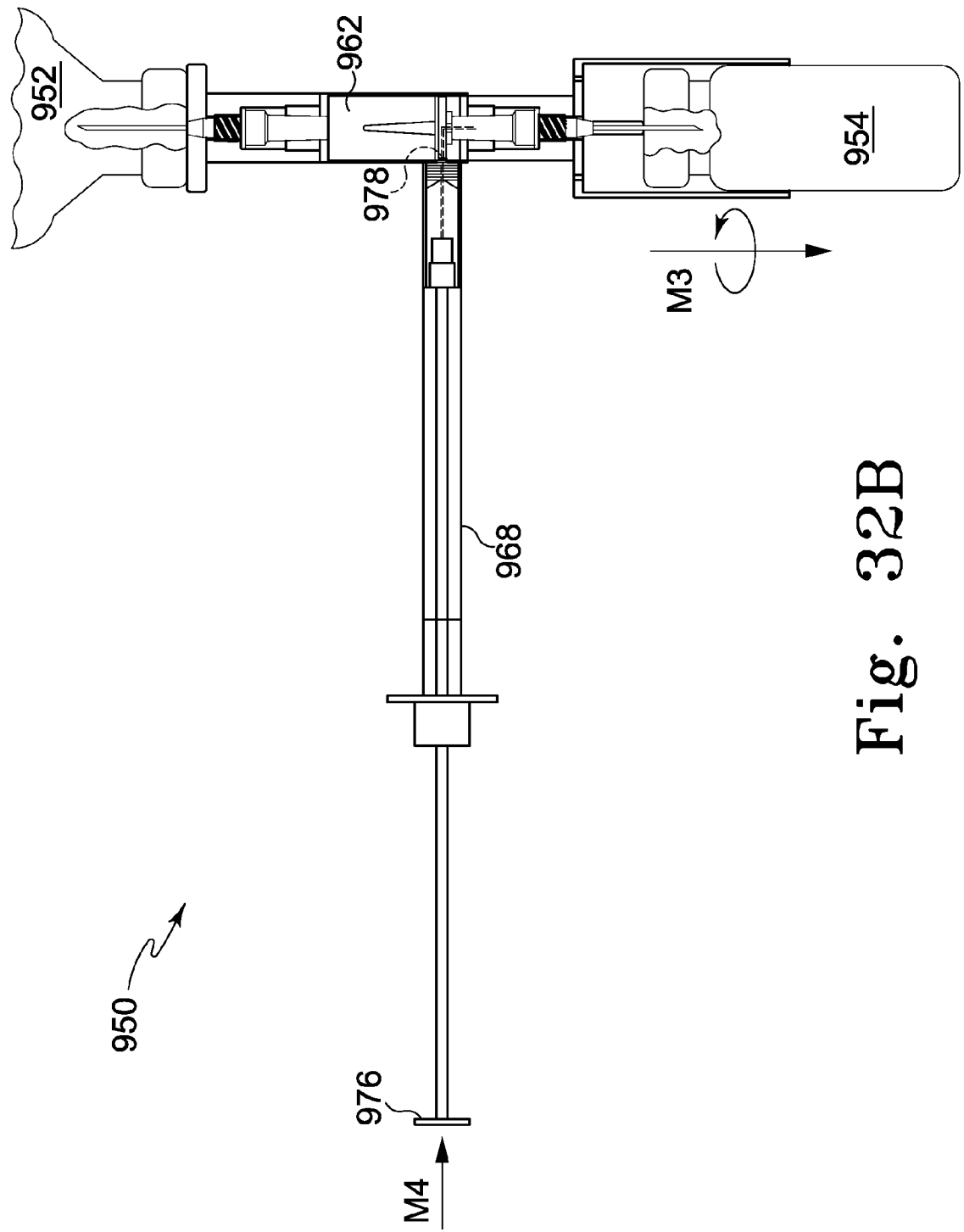

FIG. 32B shows dispenser station 950 in an intermediate configuration. Here, receiver vessel 954 has been moved down, holding reservoir 962 has been expanded to a high-volume configuration in which it has received and holds fluid from supply vessel 952, and plunger 976 has been pulled out to pull air into syringe pump 968. In the pictured embodiment, receiver conduit 966 has been positioned, via translational and/or rotational movement of receiver vessel 954, to form an air path 978 between the syringe pump and receiver vessel.

The dispenser station may effectuate transfer in two steps. First, the receiver vessel and supply vessel may again be moved relative to one another, to break the air path between the syringe pump and receiver vessel, and to create an air path between the syringe pump and the holding reservoir. Typically, this is accomplished by moving the receiver vessel slightly down (and/or around), as shown at M3 in the drawing, while keeping the supply vessel fixed. Second, following the first step, the pump is actuated to pump air into the holding reservoir. This air will move up (under the influence of the buoyant force), and push fluid down into the receiver vessel. Here, where the pump is a syringe pump, the pump may be actuated by pushing in the plunger. The amount of air pushed back into the reservoir in this configuration (e.g., about 0.25 or 0.5 mL) may be less than or about equal to the amount of air withdrawn in the previous configuration (e.g., about 1 or 2 mL).

Figure 32C:
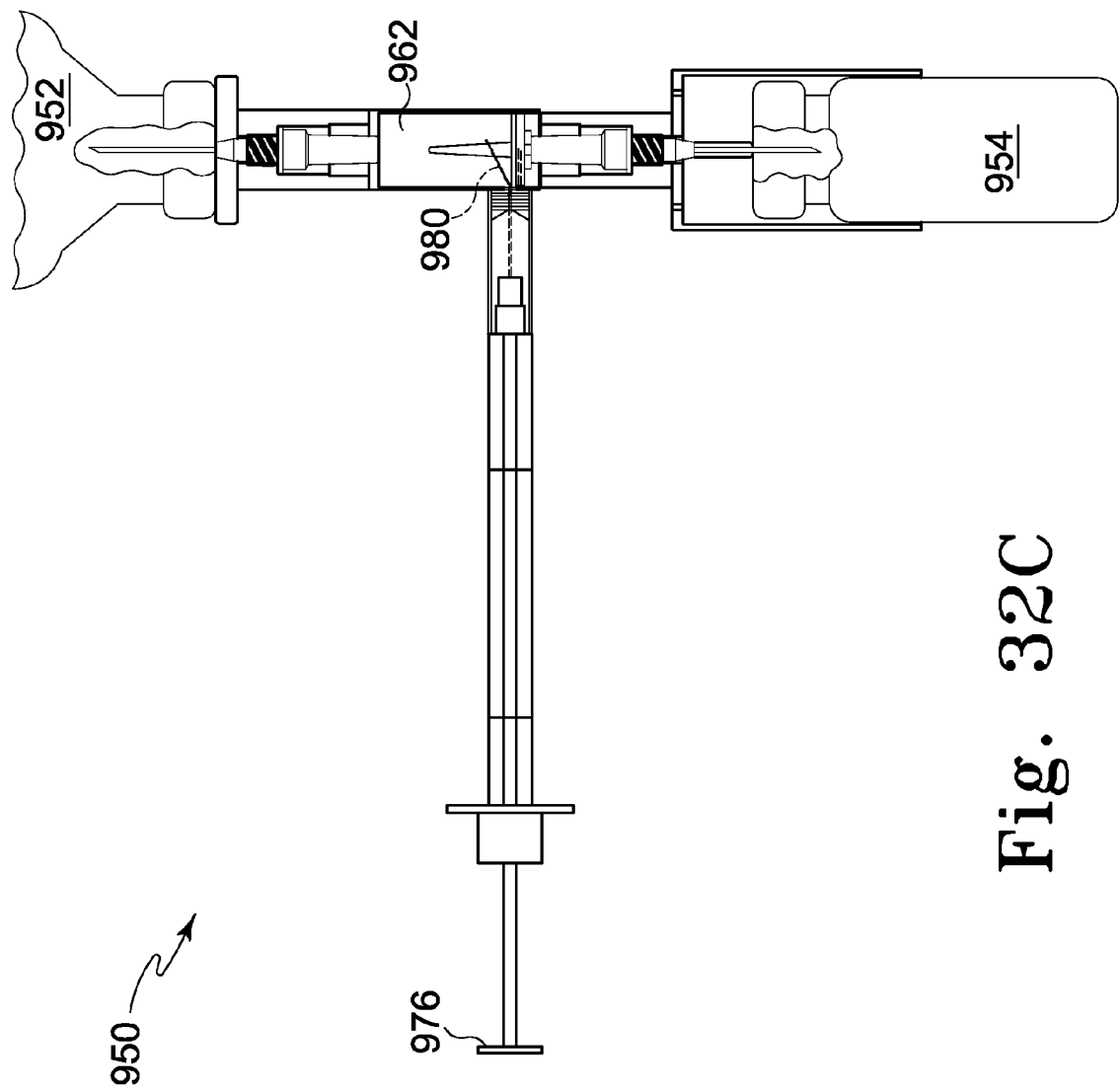

FIG. 32C shows dispenser station 950 in a final, postdispense configuration. Here, plunger 976 has been pushed partially or fully in, air 980 concomitantly has been injected into holding reservoir 962, and fluid concomitantly (or shortly thereafter) has been dispensed into receiver vessel 954.

The preceding configurations and steps may be repeated, for example, to dispense into different receiving vessels. In some cases, it may be possible to perform multiple dispense operations by shuttling between the configurations shown in FIGS. 32B and 32C, without returning to the configuration shown in FIG. 32A, until the fluid in the holding reservoir is depleted.

The dispenser station may be returned to its initial configuration following use, with or without an attached receiver vessel. Significantly, moving the receiver vessel and supply vessel toward one another will reduce the volume of the holding reservoir, from a high-volume to low-volume configuration, and push any remaining undispensed fluid back into the supply vessel, without ever having exposed the fluid to the contents of the receiver vessel.

Example 9

Dispenser Station with Automated Dispense Verification and/or Inventory Control

This example describes an exemplary dispenser station with automated dispense verification and/or inventory control. This station, and/or components thereof, may be used, if at all, instead of, or in combination with, other dispenser stations, including but not limited to dispenser stations described elsewhere herein. In these embodiments, the station includes a mechanism for verifying the presence and, in some cases, accuracy of fluid dispensing. Specifically, the station includes a sensor that monitors fluid dispensing from the supply vessel into the receiver vessel, either by sensing the fluid as it is dispensed, and/or by sensing the decreased fluid in the supply vessel and/or increased fluid in the receiver vessel after it has been dispensed. The mechanism may be used to verify the accuracy of the dispense, for example, as a quality control mechanism, and/or the quantity of fluid in the supply vessel, for example, as an inventory control mechanism. The results may be used alone and/or in combination with other results (e.g., from other sensors). In an exemplary embodiment, an inertial sensor is attached to a vessel, such as a supply vessel and/or receiver vessel. Suitable inertial sensors include silicon or piezoelectric devices, which are very sensitive. Before, during, and/or after each dispense cycle, a force and/or jerk may be delivered to the vessel, for example, by "tapping" the vessel sharply with an actuator, such as a voice coil actuator. The response from the inertial sensor may be recorded, for example, before and after dispensing. The difference in the mass of the vessel, due to the removal or addition of fluid, can be related to the dispensed fluid volume using well-known relationships. For example, the total mass of dispensed fluid will be equal to the density of the dispensed fluid times the volume of dispensed fluid. Thus, inverting this relationship, the volume of dispensed fluid will be equal to the total mass of dispensed fluid divided by the density of the dispensed fluid. In most cases, the density of fluid may be adequately approximated using the density of water or physiological buffer.

Example 10

Selected Embodiments

This example describes selected embodiments of the present teachings, presented as a series of indexed paragraphs.

1. A system for dispensing biological fluids, comprising: (A) a housing configured to hold a plurality of supply vessels containing biological fluids; and (B) a plurality of dispensers, each dispenser being configured to couple a supply vessel to a receiver vessel by engagement with a closure of the supply vessel and with a closure of the receiver vessel and being operable to transfer a measured volume of fluid from the supply vessel to the receiver vessel without disengagement from the supply vessel.

2. The system of paragraph 1, wherein the housing defines a plurality of apertures, and wherein the housing is configured to receive the supply vessels through the apertures.

3. The system of paragraph 1, the housing defining an interior compartment, further comprising a cooling device operable to cool the interior compartment.

4. The system of paragraph 3, wherein the cooling device includes a peltier device.

5. The system of paragraph 1, further comprising a base, wherein the housing is connected pivotably to the base.

6. The system of paragraph 5, wherein the housing has a plurality of discrete sides, and wherein the dispensers are configured to be arranged generally along each side.

7. The system of paragraph 1, wherein the housing includes a bottom wall defining a plurality of apertures, and wherein the supply vessels are configured to be received through the apertures such that the dispensers are disposed at least substantially below the apertures adjacent closures of the supply vessels.

8. The system of paragraph 1, wherein each dispenser includes a pump and at least one valve, and wherein the at least one valve is adjustable to provide fluid communication selectively between the pump and the supply vessel or selectively between the pump and the receiver vessel, so that adjustment of the at least one valve permits the pump to load fluid selectively from the supply vessel and then deliver the fluid selectively to the receiver vessel.

9. The system of paragraph 8, wherein the at least one valve is adjustable via movement of at least a portion of the pump.

10. The system of paragraph 1, wherein each dispenser includes a pair of conduits configured to penetrate the closure of the supply vessel and the closure of the receiver vessel, such that each conduit is disposed in sealed engagement with its respective closure.

11. The system of paragraph 1, wherein the dispenser includes a check valve that restricts reverse flow from the receiver vessel to the supply vessel.

12. The system of paragraph 1, wherein the dispenser includes a pinch valve.

13. The system of paragraph 12, wherein the pinch valve is configured to be actuated manually.

14. The system of paragraph 13, wherein the dispenser includes a pump, and wherein movement of the pump actuates the pinch valve.

15. The system of paragraph 12, wherein the pinch valve is configured to be actuated electrically.

16. The system of paragraph 1, wherein the dispenser includes at least one valve and a syringe pump having a plunger, and wherein the at least one valve is configured to be operated by translational motion of the plunger.

17. The system of paragraph 1, wherein the dispenser includes a pump and a motor configured to drive operation of the pump.

18. The system of paragraph 1, wherein the dispenser includes a decontamination mechanism configured to kill and/or inactivate microorganisms.

19. The system of paragraph 18, wherein the decontamination mechanism includes an ultraviolet light source.

20. The system of paragraph 1, wherein the dispenser includes a pump and a sensor configured to detect operation of the pump.

21. The system of paragraph 20, wherein the pump includes a piston, and wherein the sensor is configured to output a signal related to a position of the piston.

22. The system of paragraph 20, further comprising a controller in communication with the sensor and configured such that the controller uses data from the sensor to record information about operation of the pump.

23. The system of paragraph 22, wherein the information relates to a volume of fluid dispensed by the pump.

24. The system of paragraph 22, wherein the information relates to which dispenser was operated to dispense fluid.

25. The system of paragraph 20, wherein the sensor is a potentiometer or an encoder.

26. The system of paragraph 20, wherein the pump is coupled to a rack-and-pinion mechanism, and wherein the sensor is configured to sense position and/or movement of the rack and pinion mechanism.

27. The system of paragraph 22, wherein the controller is configured to store data predefining a mixture of biological fluids to be created, and wherein the controller is configured to actuate generation of a signal if the mixture is not created correctly by a person operating the dispensers.

28. The system of paragraph 27, wherein the signal is audible.

29. The system of paragraph 27, wherein the controller is configured to actuate generation of the signal if a volume dispensed by the dispenser is outside a predefined range.

30. The system of paragraph 27, wherein the controller is configured to actuate generation of the signal if a biological fluid not included in the mixture is dispensed.

31. The system of paragraph 1, further comprising a temperature control system and a controller, wherein the controller is configured to monitor operation of the temperature control system by recording temperatures sensed by the temperature control system over a time period.

32. The system of paragraph 1, wherein the housing includes a plurality of sub-housings each configured to hold a plurality of supply vessels, and wherein the sub-housings are movable relative to one another.

33. The system of paragraph 32, wherein the sub-housings are pivotable relative to one another about the same pivot axis.

34. The system of paragraph 1, wherein the dispenser includes a housing, further comprising a blower mechanism configured to provide a net positive pressure in the housing.

35. The system of paragraph 34, wherein the blower mechanism generates a stream of filtered air, further comprising a cooling device that cools the air stream.

36. The system of paragraph 1, wherein the housing is configured to hold sets of supply vessels, further comprising a thermal control system that individually regulates the temperature of each set.

37. A system for dispensing biological fluids, comprising: (A) a housing configured to hold a plurality of supply vessels containing biological fluids; and (B) a plurality of dispensers configured to be connected to the supply vessels, each dispenser including a syringe pump and at least one valve operated by the syringe pump and configured such that the at least one valve is adjustable via the syringe pump to permit (1) selective fluid communication between the syringe pump and a supply vessel and (2) selective fluid communication between the pump and a receiver vessel, so that the syringe pump can draw fluid selectively from the supply vessel and then deliver the fluid selectively to the receiver vessel.

38. The system of paragraph 37, wherein the at least one valve is a stop cock valve.

39. The system of paragraph 37, wherein the syringe pump is movable between a loading position in which fluid can be drawn selectively from the supply vessel and a delivery position in which the fluid can be delivered selectively to the receiver vessel.

40. The system of paragraph 39, wherein each dispenser includes an outlet structure from which fluid can be delivered to receiver vessels, and wherein the outlet structure moves to a more accessible position when the pump is moved into a delivery position for delivering the fluid to the receiver vessel.

41. The system of paragraph 39, wherein each dispenser includes an outlet structure including a sheathed, hollow needle.

42. A device for dispensing a biological fluid, comprising:
a conduit structure configured to couple a supply vessel to a receiver vessel by penetrating a closure of each vessel; and
a pump configured to move a measured volume of fluid through the conduit structure from the supply vessel to the receiver vessel.

43. The device of paragraph 42, further comprising at least one valve configured to restrict flow of the fluid in the conduit structure.

44. The device of paragraph 43, wherein the at least one valve is adjustable to permit (1) selective fluid communication between the syringe pump and the supply vessel and (2) selective fluid communication between the syringe pump and the receiver vessel, so that the syringe pump can draw fluid selectively from the supply vessel and then deliver the fluid selectively to the receiver vessel.

45. The device of paragraph 42, wherein the device is disposed in a package in a sterile condition.

46. The device of paragraph 42, wherein the pump is a syringe pump.

47. The device of paragraph 42, further comprising a housing configured to at least substantially enclose the conduit structure.

48. A method of dispensing a biological fluid, comprising: (A) coupling a supply vessel holding a biological fluid to a receiver vessel using a dispenser engaged with a closure of each vessel; and (B) operating the dispenser to transfer a portion of the biological fluid through the closures from the supply vessel to the receiver vessel.

49. The method of paragraph 48, wherein the steps of coupling and operating are performed a plurality of times with the same receiver vessel and distinct supply vessels, to form a mixture in the receiver vessel.

50. The method of paragraph 49, wherein the distinct supply vessel hold different allergen extracts such that the steps of coupling and operating form an allergen mixture in the receiver vessel.

51. The method of paragraph 48, wherein the steps of coupling and operating are performed a plurality of times with the same supply vessel and distinct receiver vessels to dispense portions of the biological fluid to the distinct receiver vessels.

52. The method of paragraph 48, wherein the step of operating the dispenser includes (1) a step of loading a pump with the biological fluid and (2) a step of delivering the biological fluid from the pump to the receiver vessel.

53. The method of paragraph 48, further comprising a step of injecting a person with the biological fluid from the receiver vessel.

54. The method of paragraph 48, wherein the step of operating is performed with the supply vessel disposed in a cooled compartment.

55. A method of dispensing a biological fluid, comprising: (A) coupling a dispenser to a supply vessel holding a biological fluid and sealed by a closure; (B) loading a portion of the biological fluid into the dispenser from the supply vessel through the closure; and (C) delivering the biological fluid from the dispenser to a receiver vessel, through a closure of the receiver vessel, while the dispenser remains coupled to the supply vessel.

56. The method of paragraph 55, wherein the step of coupling includes a step of penetrating the closure of the supply vessel with a conduit, and wherein the step of loading includes a step of moving the biological fluid through the conduit.

57. The method of paragraph 55, wherein the steps of loading and delivering include a step of operating a pump manually.

58. The method of paragraph 57, wherein the step of operating a pump manually includes a step of operating a syringe pump.

59. The method of paragraph 55, further comprising a step of placing the receiver vessel into engagement with the dispenser, wherein the step of placing is performed after the step of loading.

60. The method of paragraph 59, wherein the step of placing includes a step of penetrating the closure of the receiver vessel with a conduit.

61. The method of paragraph 55, wherein the step of delivering includes a step of delivering a measured volume of the biological fluid to the receiver vessel.

62. The method of paragraph 55, wherein the steps of coupling, loading, and delivering are performed a plurality of times so that different biological fluids are combined in the receiver vessel to form a mixture of the different biological fluids.

63. The method of paragraph 62, wherein the step of delivering is repeated a plurality of times with different allergen extracts so that the different allergen extracts are mixed in the receiver vessel.

64. A method of dispensing a biological fluid, comprising: (A) drawing a portion of a biological fluid into a pump from a supply vessel; (B) operating at least one valve by movement of the pump to create fluid communication between the pump and a receiver vessel and to break fluid communication between the pump and the supply vessel; and (C) delivering a measured volume of the biological fluid from the pump to the receiver vessel.

65. The method of paragraph 64, wherein the steps of drawing, operating, and delivering are performed a plurality of times with different biological fluids to form a mixture of the biological fluids in the receiver vessel.

66. The method of paragraph 64, further comprising a step of disposing the supply vessel in a housing that pivots on a base before the step of drawing.

67. A method of forming an allergen mixture, comprising: (A) coupling supply vessels to a plurality of dispensers, the supply vessels holding different allergens in fluid; and (B) operating the dispensers to deliver a portion of each allergen to a receiver vessel while the dispensers remain coupled to the supply vessels, to form an allergen mixture suitable for injection into a human recipient.

68. The method of paragraph 67, wherein the step of coupling disposes the supply vessels in an array at least substantially inside a housing in which the supply vessels are refrigerated.

69. The method of paragraph 68, the housing being coupled movably to a base, further comprising a step of moving the housing relative to the base between operation of at least two of the dispensers.

70. The method of paragraph 69, wherein the step of moving includes a step of pivoting the housing.

71. The method of paragraph 67, wherein the step of operating includes (1) a step of loading a pump with an allergen, and (2) a step of delivering a measured volume of the allergen to the receiver vessel.

72. The method of paragraph 67, wherein the step of operating includes a step of adjusting at least one valve for each dispenser.

73. The method of paragraph 72, wherein the step of adjusting the valve is performed by movement of at least a portion of a pump of the dispenser.

74. The method of paragraph 67, wherein the step of operating the dispensers includes a step of penetrating a closure of the receiver vessel with a conduit of each dispenser.

75. The method of paragraph 67, wherein the step of operating includes a step of delivering the different allergens sequentially to the receiver vessel.

76. A method of forming a mixture of biological fluids, comprising: (A) operating a plurality of pumps manually to transfer a plurality of biological fluids from distinct supply vessels to the same receiver vessel to create a mixture; and (B) monitoring the step of operating automatically with a controller in communication with sensors coupled to each of the pumps.

77. The method of paragraph 76, further comprising a step of inputting to the controller data corresponding to fluid types and volumes to be included in the mixture before the step of operating.

78. The method of paragraph 77, wherein the step of monitoring produces dispensing data, further comprising a step of comparing the data corresponding to the fluid types and volume with the dispensing data to determine whether or not the step of operating was performed correctly.

79. The method of paragraph 76, further comprising a step of storing data produced by the step of monitoring.

80. A system for dispensing a biological fluid, comprising: (A) means for dispensing a biological fluid; (B) means for coupling a supply vessel holding a biological fluid to a receiver vessel by engagement with a closure of each vessel; and (C) means for operating the means for dispensing to transfer a portion of the biological fluid through the closures from the supply vessel to the receiver vessel.

81. The system of paragraph 80, further comprising means for housing a plurality of supply vessels containing biological fluids, wherein the means for housing is configured to be connected to the means for coupling.

82. A system for dispensing a biological fluid, comprising: (A) means for dispensing a biological fluid; (B) means for coupling the means for dispensing to a supply vessel holding a biological fluid and sealed by a closure; (C) means for loading a portion of the biological fluid into the means for dispensing from the supply vessel through the closure; and (D) means for delivering the biological fluid from the means for dispensing to a receiver vessel through a closure of the receiver vessel while the means for dispensing remains coupled to the supply vessel.

83. A system for dispensing allergens, comprising: (A) a plurality of means for dispensing biological fluids; (B) means for coupling supply vessels to the plurality of means for dispensing, the supply vessels holding different allergens in fluid; and (C) means for operating the dispensers to deliver a portion of each allergen to a receiver vessel while the dispensers remain coupled to the supply vessels, to form an allergen mixture suitable for injection into a human recipient.

84. An apparatus for dispensing biological fluids, comprising: (A) a housing; and (B) a plurality of dispensers connected to the housing and configured to dispense measured volumes of biological fluids, under substantially sterile conditions, from supply vessels to receiver vessels that can be selectively engaged with the dispensers while the supply vessels remain connected to the dispensers.

85. The apparatus of paragraph 84, wherein the housing defines an interior compartment and a plurality of apertures, and wherein the housing is configured to receive the supply vessels in the apertures, with the supply vessels connected to the dispensers, so that the supply vessels are disposed at least substantially in the interior compartment.

86. The apparatus of paragraph 85, further comprising a cooling device operable to cool the interior compartment.

87. The apparatus of paragraph 86, wherein the cooling device is a Peltier device.

88. The apparatus of paragraph 84, further comprising a base, wherein the housing is connected pivotably to the base.

89. The apparatus of paragraph 88, wherein the housing defines a pivot axis, and wherein the dispensers are configured to be mounted to the housing at a plurality of positions around the pivot axis, so that pivotal movement of the housing can select a subset of the dispensers that are more accessible to a person adjacent the housing.

90. The apparatus of paragraph 84, wherein the dispensers are configured to support the supply vessels in an inverted configuration.

91. The apparatus of paragraph 84, wherein the housing includes a bottom wall defining a plurality of apertures, and wherein the dispensers are configured to be secured to the bottom wall with the supply vessels received in the apertures.

92. The apparatus of paragraph 84, wherein each dispenser includes a pump and a valve, and wherein the valve is operable manually to provide fluid communication selectively between the pump and a supply vessel or between the pump and the receiver vessel, so that operation of the valve permits the pump to load a measured volume of biological fluid from the supply vessel and then deliver the measured volume to the receiver vessel.

93. The apparatus of paragraph 92, wherein the supply vessels and the receiver vessels include closures, and wherein the dispensers are configured to transfer portions of the biological fluids between the supply vessels and the receiver vessels through the closures.

94. The apparatus of paragraph 93, wherein the dispensers include hollow needles to penetrate the closures.

95. An apparatus for dispensing biological fluids, comprising: (A) a housing; and (B) a plurality of dispensers connected to the housing, each dispenser including a pump and a valve operated by movement of the pump, the pump having a loading position in which the valve permits fluid communication between the pump and a supply vessel holding a biological fluid, and a delivery position in which the valve permits fluid communication between the pump and a receiver vessel, so that the pump can draw a volume of the biological fluid from the supply vessel in the loading position and then deliver the volume to the receiver vessel in the delivery position.

96. The apparatus of paragraph 95, wherein the pump includes a syringe, and wherein the syringe is configured to be detachable from the dispenser.

97. The apparatus of paragraph 95, wherein the valve includes an outer member and an inner member each including one or more channels, the outer member being coupled pivotably to the inner member to permit adjustable fluid communication between the one or more channels of the outer and inner members, and wherein movement of the pump between the loading position and the delivery position pivots the outer member while the inner member remains at least substantially stationary.

98. The apparatus of paragraph 95, wherein the dispenser includes a housing structure, and wherein the housing structure includes stops that restrict movement of the pump substantially outside a range of motion from the loading position to the delivery position.

99. The apparatus of paragraph 95, wherein each dispenser includes an outlet structure from which the biological fluid is delivered into the receiver vessel, and wherein the outlet structure moves to a more accessible position when the pump is moved from the loading position to the delivery position.

100. The apparatus of paragraph 99, wherein the more accessible position is configured to permit engagement of the outlet structure with the receiver vessel by generally upward movement of the receiver structure from underneath the dispenser.

101. The apparatus of paragraph 99, wherein the outlet structure includes a sheathed, hollow needle.

102. The apparatus of paragraph 95, wherein the dispensers are configured to transfer the biological fluids to the receiver vessel under at least substantially sterile conditions.

103. A system for dispensing biological fluids, comprising: (A) a housing defining an interior compartment configured to receive supply vessels of biological fluids; (B) a cooling device configured to maintain the temperature of the interior compartment below ambient temperature; and (C) a plurality of dispensers configured to transfer manually, under substantially sterile conditions, measured volumes of the biological fluids from the supply vessels to receiver vessels selectively engaged with the dispensers.

104. A method of dispensing a biological fluid, comprising: (A) coupling a dispenser to a supply vessel holding a biological fluid; (B) passing a portion of the biological fluid through a closure of the supply vessel and into the dispenser so that the dispenser is loaded; and (C) delivering a volume of the biological fluid, after the step of passing, from the dispenser to a receiver vessel disposed in fluid communication with the dispenser, the volume flowing through a closure of the receiver vessel and into the receiver vessel while the dispenser remains coupled to the supply vessel.

105. The method of paragraph 104, wherein the step of coupling includes a step of penetrating the closure of the supply vessel with a conduit, and wherein the step of passing includes a step of moving the portion of the biological fluid through the conduit.

106. The method of paragraph 105, the closure being a resilient septum, wherein the step of penetrating is performed with a needle.

107. The method of paragraph 104, wherein the step of passing includes a step of operating a pump manually.

108. The method of paragraph 107, the pump being a syringe having a plunger, wherein the step of passing includes a step of moving the plunger of the syringe.

109. The method of paragraph 104, the volume being a delivered volume, wherein the step of passing includes a step of loading a loaded volume of the biological fluid into the dispenser, and wherein the loaded volume corresponds substantially to the delivered volume.

110. The method of paragraph 104, further comprising a step of placing the receiver vessel into engagement with the dispenser, wherein the step of placing is performed after the step of passing.

111. The method of paragraph 110, wherein the step of placing includes a step of penetrating the closure of the receiver vessel with a delivery conduit.

112. The method of paragraph 111, further comprising a step of moving the delivery conduit after the step of passing and before the step of penetrating.

113. The method of paragraph 112, the dispenser including a pump, wherein the step of moving is performed by moving the pump.

114. The method of paragraph 104, wherein the step of delivering includes a step of delivering a measured volume of the biological fluid to the receiver vessel.

115. The method of paragraph 104, wherein the steps of coupling, passing, and delivering are performed a plurality of times so that different biological fluids are combined in the receiver vessel to form a mixture.

116. The method of paragraph 114, wherein the steps of passing and delivering are performed with biological fluids including allergens so that an allergen mixture is formed.

117. A method of dispensing a biological fluid, comprising: (A) drawing a portion of a biological fluid into a pump from a supply vessel; (B) operating a valve by movement of the pump to create fluid communication between the pump and a receiver vessel and to break fluid communication between the pump and the supply vessel; and (C) delivering a measured volume of the biological fluid from the pump to the receiver vessel.

118. The method of paragraph 117, wherein the steps of drawing, operating, and delivering are performed a plurality of times with different biological fluids to form a mixture of the biological fluids in the receiver vessel.

119. The method of paragraph 117, further comprising a step of disposing the supply vessel in a housing that pivots on a base.

120. A method of forming an allergen mixture, comprising: (A) coupling supply vessels to a plurality of dispensers, the supply vessels holding different allergens in fluid; and (B) operating the dispensers to deliver a portion of each allergen to a receiver vial, under sterile conditions, while the dispensers remain coupled to the supply vessels.

121. The method of paragraph 120, wherein the step of coupling disposes the supply vessels in an array at least substantially inside a refrigerated housing.

122. The method of paragraph 121, the housing being coupled movably to a base, further comprising a step of moving the housing relative to the base between operation of at least two of the dispensers.

123. The method of paragraph 120, wherein the step of moving includes a step of pivoting the housing.

124. The method of paragraph 120, wherein the step of operating includes (1) a step of loading a pump with a portion of an allergen, and (2) a step of delivering a measured volume of the allergen to the receiver vessel, and wherein the measured volume corresponds substantially to the portion.

125. The method of paragraph 120, wherein the step of operating includes a step of adjusting a valve for each dispenser.

126. The method of paragraph 125, wherein the step of adjusting the valve is performed by movement of a pump of the dispenser.

127. The method of paragraph 120, wherein the step of operating the dispensers includes a step of penetrating a closure of the receiver vessel with conduit of each dispenser.

128. The method of paragraph 120, wherein the step of operating includes a step of delivering the portions sequentially to the receiver vial.

129. An apparatus for dispensing a biological fluid, comprising: (A) means for coupling a dispenser to a supply vessel holding a biological fluid; (B) means for passing a portion of the biological fluid through a closure of the supply vessel and into the dispenser so that the dispenser is loaded; and (C) means for delivering a volume of the biological fluid, after the step of passing, from the dispenser to a receiver vessel disposed in fluid communication with the dispenser, the volume flowing through a closure of the receiver vessel and into the receiver vessel while the dispenser remains coupled to the supply vessel.

130. An apparatus for dispensing allergens, comprising: (A) means for coupling supply vessels to a plurality of dispensers, the supply vessels holding different allergens in fluid; and (B) means for operating the dispensers to deliver a portion of each allergen to a receiver vial, under sterile conditions, while the dispensers remains coupled to the supply vessels.

The disclosure set forth above may encompass one or more distinct inventions, with independent utility. Each of these inventions has been disclosed in its preferred form(s). These preferred forms, including the specific embodiments thereof as disclosed and illustrated herein, are not intended to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method of dispensing biological fluid, comprising:

operating at least one cooling device to refrigerate a plurality of sealed stock vials disposed in an array in a housing, the stock vials holding biological fluids;

blowing filtered air into a compartment disposed below a stock vial disposed in the housing; and transferring an aliquot of a biological fluid held by the stock vial, out through a resilient closure of the stock vial and into a syringe pump disposed in the compartment, wherein the step of transferring includes a step of transferring at least a portion of the aliquot from the syringe pump to a receiver vial, through a resilient closure of the receiver vial, and wherein the step of transferring is performed a plurality of times with aliquots of different biological fluids to form a mixture of the different biological fluids in the receiver vial.

2. The method of claim 1, wherein the step of blowing filtered air includes a step of filtering air to remove microorganisms.

3. The method of claim 2, where the step of filtering air includes a step of filtering air with a HEPA filter.

4. The method of claim 1, where the step of blowing filtered air includes a step of creating a positive pressure in the compartment with the filtered air to reduce entry of unfiltered air into the compartment.

5. The method of claim 1, wherein the stock vial is disposed in a vessel storage compartment in the housing, further comprising a step of blowing filtered air into the vessel storage compartment.

6. The method of claim 1, further comprising a step of disposing at least one stock vial in the housing such that a label and/or a fluid level of the at least one stock vial is visible from outside the housing.

7. The method of claim 6, wherein the step of disposing includes a step of disposing the at least one stock vial behind a transparent wall of the housing such that at least a portion of the at least one stock vial is visible through the transparent wall.

8. The method of claim 1, further comprising a step of disposing the stock vials in the array, with each stock vial in an inverted configuration.

9. The method of claim 1, wherein the step of transferring performed a plurality of times includes a step of transferring allergens to make an allergen mixture for an allergy patient.

10. The method of claim 1, wherein the housing is connected to a base, further comprising a step of rotating the array of stock vials relative to the base in order to select the stock vial from which the aliquot is to be transferred.

11. The method of claim 1, wherein the step of transferring includes a step of automatically operating a power-driven syringe pump.

12. The method of claim 1, further comprising a step of inputting instructions for the step of transferring to a controller that controls operation of the syringe pump.

13. The method of claim 12, wherein the step of inputting instructions includes a step of inputting instructions to the controller via a touchscreen.

14. The method of claim 1, wherein the syringe pump is a manually driven syringe.

15. The method of claim 1, wherein a distinct syringe pump is used each time the step of transferring is performed.

* * * * *